US007074983B2

(12) United States Patent
Robl et al.

(10) Patent No.: US 7,074,983 B2
(45) Date of Patent: Jul. 11, 2006

(54) TRANSGENIC BOVINE COMPRISING HUMAN IMMUNOGLOBULIN LOCI AND PRODUCING HUMAN IMMUNOGLOBULIN

(75) Inventors: James M. Robl, Brandon, SD (US); Richard A. Goldsby, Leverett, MA (US); Stacy E. Ferguson, Dallas, TX (US); Yoshimi Kuroiwa, Takasaki (JP); Kazuma Tomizuka, Takasaki (JP); Isao Ishida, Isehara (JP); Barbara A. Osborne, Leverett, MA (US)

(73) Assignees: Kirin Beer Kabushiki Kaisha, Tokyo (JP); Hematech, LLC, Westport, CT (US)

( * ) Notice: Subject to any disclaimer, the term of this patent is extended or adjusted under 35 U.S.C. 154(b) by 68 days.

(21) Appl. No.: 09/988,115

(22) Filed: Nov. 16, 2001

(65) Prior Publication Data
US 2003/0037347 A1 Feb. 20, 2003

Related U.S. Application Data

(63) Continuation-in-part of application No. 09/714,185, filed on Nov. 17, 2000, now abandoned.

(60) Provisional application No. 60/311,625, filed on Aug. 9, 2001, provisional application No. 60/256,458, filed on Dec. 20, 2000, provisional application No. 60/166,410, filed on Nov. 19, 1999.

(51) Int. Cl.
A01K 67/27 (2006.01)
C12P 21/00 (2006.01)
A61K 38/00 (2006.01)

(52) U.S. Cl. .................... 800/15; 800/4; 800/6; 514/12
(58) Field of Classification Search ............ 800/14–18, 800/24, 4–7; 435/325, 326; 514/12
See application file for complete search history.

(56) References Cited

U.S. PATENT DOCUMENTS

| | | | |
|---|---|---|---|
| 4,797,356 A | 1/1989 | Brandt et al. ................... 435/7 |
| 4,847,081 A | 7/1989 | Rice ........................ 424/186.1 |
| 4,873,316 A | 10/1989 | Meade et al. ................ 530/412 |
| 4,959,317 A | 9/1990 | Sauer ...................... 435/172.3 |
| 4,994,384 A | 2/1991 | Prather et al. ............ 435/172.3 |
| 5,021,244 A | 6/1991 | Spaulding ................... 424/561 |
| 5,057,420 A | 10/1991 | Massey .................... 435/172.2 |
| 5,096,822 A | 3/1992 | Rosenkrans, Jr. et al. .. 435/388 |
| 5,160,312 A | 11/1992 | Voelkel ........................ 600/34 |
| 5,175,384 A | 12/1992 | Krimpenfort et al. .......... 800/2 |
| 5,213,979 A | 5/1993 | First et al. ................ 435/240.2 |
| 5,320,952 A | 6/1994 | Deutch et al. ............. 435/69.1 |
| 5,346,990 A | 9/1994 | Spaulding ................... 530/350 |
| 5,374,544 A | 12/1994 | Schwartz et al. .......... 435/69.1 |
| 5,434,066 A | 7/1995 | Bebee et al. ............. 435/172.3 |
| 5,434,340 A | 7/1995 | Krimpenfort et al. .......... 800/2 |
| 5,453,366 A | 9/1995 | Sims et al. ............... 435/172.3 |
| 5,464,764 A | 11/1995 | Capecchi et al. ............... 435/6 |
| 5,470,560 A | 11/1995 | Martin, Jr. .................... 424/9.2 |
| 5,482,856 A | 1/1996 | Fell, Jr. et al. .......... 435/320.1 |
| 5,487,992 A | 1/1996 | Capecchi et al. ........ 435/172.3 |
| 5,496,720 A | 3/1996 | Susko-Parrish et al. .. 435/240.2 |
| 5,527,674 A | 6/1996 | Guerra et al. ................... 435/6 |
| 5,545,806 A | 8/1996 | Lonberg et al. ................ 800/2 |
| 5,545,807 A | 8/1996 | Surani et al. .................. 800/2 |
| 5,565,350 A | 10/1996 | Kmiec ...................... 435/172.3 |
| 5,565,362 A | 10/1996 | Rosen ..................... 435/320.1 |
| 5,569,825 A * | 10/1996 | Lonberg et al. ............... 800/18 |
| 5,583,016 A | 12/1996 | Villeponteau et al. ..... 435/91.3 |
| 5,591,669 A | 1/1997 | Krimpenfort et al. .......... 800/2 |
| 5,612,205 A | 3/1997 | Kay et al. ................. 435/172.3 |
| 5,614,396 A | 3/1997 | Bradley et al. .......... 435/172.3 |
| 5,618,686 A | 4/1997 | Kojima et al. ................. 435/26 |
| 5,625,126 A | 4/1997 | Lonberg et al. ................ 800/2 |
| 5,627,059 A | 5/1997 | Capecchi et al. ............. 800/21 |
| 5,631,153 A | 5/1997 | Capecchi et al. ........ 435/172.3 |
| 5,633,076 A | 5/1997 | DeBoer et al. .......... 435/172.3 |
| 5,633,425 A | 5/1997 | Lonberg et al. ................ 800/2 |
| 5,639,457 A | 6/1997 | Brem et al. ............... 424/184.1 |
| 5,652,373 A | 7/1997 | Reisner ....................... 800/11 |
| 5,654,182 A | 8/1997 | Wahl et al. ............... 435/172.1 |
| 5,660,997 A | 8/1997 | Spaulding ................. 435/7.21 |
| 5,661,016 A | 8/1997 | Lonberg et al. .......... 435/172.3 |
| 5,677,177 A | 10/1997 | Wahl et al. .................. 435/325 |
| 5,679,523 A | 10/1997 | Li et al. ......................... 435/6 |
| 5,695,977 A | 12/1997 | Jurka ....................... 435/172.3 |
| 5,698,763 A | 12/1997 | Weissmann et al. ........... 800/2 |

(Continued)

FOREIGN PATENT DOCUMENTS

EP 0773288 5/1997

(Continued)

OTHER PUBLICATIONS

Kaushik, A. et al. Novel Insight Antibody Diversification From Cattle. Veterinary Immunology and Immunopathology. 2000, vol. 87, pp. 347-350.*

Parng, Chuen-Lei et al. Gene Conversion Contributes to Ig Light Chain Diversity in Cattle. J. Immunology. 1996, vol. 157, 5478-5486.*

(Continued)

Primary Examiner—Deborah Crouch
(74) Attorney, Agent, or Firm—Clark & Elbing LLP

(57) ABSTRACT

The present invention relates to the production of a transgenic bovine which comprises a genetic modification that results in inactivation and loss of expression of its endogenous antibodies, and the expression of xenogenous antibodies, preferably human antibodies. This is effected by inactivation of the IgM heavy chain expression and, optionally, by inactivation of the Ig light chain expression, and by the further introduction of an artificial chromosome which results in the expression of non-bovine antibodies, preferably human antibodies.

19 Claims, 38 Drawing Sheets

U.S. PATENT DOCUMENTS

| | | | |
|---|---|---|---|
| 5,721,367 A | 2/1998 | Kay et al. | 800/2 |
| 5,733,730 A | 3/1998 | De Lange | 435/6 |
| 5,741,957 A * | 4/1998 | Deboer et al. | 800/7 |
| 5,750,172 A | 5/1998 | Meade et al. | 426/580 |
| 5,756,325 A | 5/1998 | Kmiec | 435/172.3 |
| 5,763,240 A | 6/1998 | Zarling et al. | 435/172.3 |
| 5,770,422 A | 6/1998 | Collins | 435/194 |
| 5,770,429 A | 6/1998 | Lonberg et al. | 435/240.2 |
| 5,776,744 A | 7/1998 | Glazer et al. | 435/172.3 |
| 5,780,009 A | 7/1998 | Karatzas et al. | 424/9.1 |
| 5,780,296 A | 7/1998 | Holloman et al. | 435/320.1 |
| 5,789,215 A | 8/1998 | Berns et al. | 435/172.3 |
| 5,789,650 A | 8/1998 | Lonberg et al. | 800/2 |
| 5,789,655 A | 8/1998 | Prusiner et al. | 800/2 |
| 5,801,030 A | 9/1998 | McVey et al. | 435/172.3 |
| 5,814,318 A | 9/1998 | Lonberg et al. | 424/184.1 |
| 5,821,117 A | 10/1998 | Sandrin et al. | 435/320.1 |
| 5,827,690 A | 10/1998 | Meade et al. | 435/69.6 |
| 5,830,698 A | 11/1998 | Reff et al. | 435/69.1 |
| 5,837,857 A | 11/1998 | Villeponteau et al. | 536/24.31 |
| 5,843,643 A | 12/1998 | Ratner | 435/6 |
| 5,843,754 A | 12/1998 | Susko-Parrish et al. | 435/240 |
| 5,849,991 A | 12/1998 | d'Apice et al. | 800/2 |
| 5,849,992 A | 12/1998 | Meade et al. | 800/2 |
| 5,874,299 A | 2/1999 | Lonberg et al. | 435/320.1 |
| 5,876,979 A | 3/1999 | Andrews et al. | 435/91.3 |
| 5,877,397 A | 3/1999 | Lonberg et al. | 800/2 |
| 5,891,698 A | 4/1999 | Prieto et al. | 435/67.1 |
| 5,945,577 A | 8/1999 | Stice et al. | 800/24 |
| 5,952,222 A | 9/1999 | Rosenkrans, Jr. et al. | 435/325 |
| 6,011,197 A | 1/2000 | Strelchenko et al. | 800/24 |
| 6,023,010 A | 2/2000 | Krimpenfort et al. | 800/2 |
| 6,030,833 A | 2/2000 | Seebach et al. | 435/325 |
| 6,054,632 A | 4/2000 | Reid | 800/6 |
| 6,066,719 A | 5/2000 | Zapata | 530/387.3 |
| 6,074,853 A | 6/2000 | Pati et al. | 435/91.1 |
| 6,077,710 A | 6/2000 | Susko-Parrish et al. | 435/375 |
| 6,091,001 A | 7/2000 | Jakobovits et al. | 800/18 |
| 6,133,503 A | 10/2000 | Scheffler | |
| 6,147,276 A | 11/2000 | Campbell et al. | 800/24 |
| 6,153,428 A | 11/2000 | Gustafsson et al. | 435/325 |
| 6,166,288 A | 12/2000 | Diamond et al. | 800/17 |
| 6,183,993 B1 | 2/2001 | Boyce et al. | 435/69.7 |
| 6,194,202 B1 | 2/2001 | Susko-Parrish et al. | 435/325 |
| 6,204,061 B1 | 3/2001 | Capecchi et al. | 435/463 |
| 6,204,431 B1 | 3/2001 | Prieto et al. | 800/14 |
| 6,252,133 B1 | 6/2001 | Campbell et al. | 800/24 |
| 6,258,998 B1 | 7/2001 | Damiani et al. | 800/24 |
| 6,271,436 B1 | 8/2001 | Piedrahita et al. | 800/21 |
| 6,300,129 B1 | 10/2001 | Lonberg et al. | 435/326 |
| 6,395,958 B1 | 5/2002 | Strelchenko et al. | 800/7 |
| 2002/0001842 A1 | 1/2002 | Chapman | 435/449 |
| 2002/0012660 A1 | 1/2002 | Coleman et al. | 424/93.21 |
| 2002/0108132 A1 | 8/2002 | Rapp | 800/6 |

FOREIGN PATENT DOCUMENTS

| | | |
|---|---|---|
| EP | 0546073 | 9/1997 |
| EP | 0843961 | 5/1998 |
| EP | 1106061 | 6/2001 |
| WO | WO 92/03918 | 3/1992 |
| WO | WO 93/10227 | 5/1993 |
| WO | WO 94/02602 | 2/1994 |
| WO | WO 95/33828 | 12/1995 |
| WO | WO 96/33735 | 10/1996 |
| WO | WO 97/07668 | 3/1997 |
| WO | WO 97/07669 | 3/1997 |
| WO | WO 97/07671 | 3/1997 |
| WO | WO 97/13852 | 4/1997 |
| WO | WO 98/14593 | 4/1998 |
| WO | WO 98/24884 | 6/1998 |
| WO | WO 98/24893 | 6/1998 |
| WO | WO 98/30683 | 7/1998 |
| WO | WO 98/37183 | 8/1998 |
| WO | WO 98/39416 | 9/1998 |
| WO | WO 99/21415 | 6/1999 |
| WO | WO 99/60108 | 11/1999 |
| WO | WO 00/10383 | 3/2000 |
| WO | WO 00/42174 | 7/2000 |
| WO | WO 00/46251 | 8/2000 |
| WO | WO 00/51424 | 9/2000 |
| WO | WO 00/67568 | 11/2000 |
| WO | WO 00/67569 | 11/2000 |
| WO | WO 00/74477 | 12/2000 |
| WO | WO 01/23541 | 4/2001 |
| WO | WO 01/30992 | 5/2001 |
| WO | WO 01/35735 | 5/2001 |
| WO | WO 01/73107 | 10/2001 |

OTHER PUBLICATIONS

Aheam et al., "Disruption of the *Cr2* Locus Results in a Reduction in B-1a Cells and in an Impaired B Cell Response to T-Dependent Antigen," *Immunity* 4:251-262 (1996).

Burke et al., "A Cell Free System to Study Reassembly of the Nuclear Envelope at the End of Mitosis," *Cell* 44:639-652 (1986).

Cibelli et al., "Bovine Chimeric Offspring Produced By Transgenic Embryonic Stem Cells Generated From Somatic Cell Nuclear Transfer Embryos," *Theriogenology* p. 236.

Cibelli et al., "Cloned Transgenic Calves Produced from Nonquiescent Fetal Fibroblasts," *Science* 280:1256-1258 (1998).

Collas et al., "Lipophilic Organizing Structures of Sperm Nuclei Target Membrane Vesicle Binding and Are Incorporated into the Nuclear Envelope," *Dev. Biol.* 169:123-135 (1995).

Collas, "Sequential PKC- and Cdc2-Mediated Phosphorylation Events Elicit Zebrafish Nuclear Envelope Disassembly," *J. Cell. Sci.* 112:977-987 (1999).

Collas et al., "The A-Kinase Anchoring Protein, AKAP95, Is A Multivalent Protein With A Key Role in Chromatin Condensation At Mitosis," *J. Cell Biol.* 147:1167-1179 (1999).

Cubizolles et al., "pEg7, A New Xenopus Protein Required For Mitotic Chromosome Condensation in Egg Extracts," *J. Cell Biol.* 143:1437-1446 (1998).

Denning et al., "Deletion of the $\alpha(1,3)$Galactosyl Transferase (GTTA1) Gene and the Prion Protein (PrP) Gene in Sheep," *Nat. Biotechnol.* 19:559-562 (2001).

Ehrenstein et al., "Targeted Gene Disruption reveals a Role for Natural Secretory IgM in the Maturation of the Primary Immune Response," *Proc. Natl. Acad. Sci.*, USA 95:10089-10093 (1998).

Erlandsson et al., "Mice with an Inactivated joining chain Locus Have Perturbed IgM Secretion," *Eur. J. Immunol.* 28:2355-2365 (1998).

Goldman et al., "Enhanced Human Cell Engraftment in Mice Deficient in RAG2 and the Common Cytokine Receptor Gamma Chain," *Br. J. Haematol.* 103:335-342 (1998).

Guidos et al., "Development of CD4+CD8+ Thymocytes in RAG-Deficient Mice Through a T Cell Receptor β Chain-Independent Pathway," *J. Exp. Med.* 181:1187-1195 (1995).

Ishida et al., "Production of a Diverse Repertoire of Human Antibodies in Genetically Engineered Mice," *Microbiol. Immunol.* 42:143-150 (1998).

Jonak et al., "Manipulation of Human B Cells to Confer Immortality," *Hum. Antibodies Hybridomonas* 3:177-185 (1992).

Joziasse et al., "Bovine Alpha 1 3-Galactosyltransferase: Isolation and Characterization of a cDNA Clone. Identification of Homologous Sequences in Human Genomic DNA," *J. Biol. Chem.* 264:14290-14297 (1989).

Joziasse et al., "Characterization of an α1-β-Galactosyltransferase Homologue on Human Chromosome 12 That is organized As A Processed Pseudogene," *J. Biol. Chem.* 266:6991-6998 (1991).

Kitamura et al., "A B Cell-Deficient Mouse by Targeted Disruption of the Membrane Exon of the Immunoglobulin Mu Chain Gene," *Nature* 350:423-426 (1991).

Knight et al., "Genetic Engineering of Bovine Ig. Construction and Characterization of Hapten-Binding Bovine/Murine Chimeric IgE, IgA, IgG1, IgG2, and IgG3 Molecules," *J. Immunol.* 140:3654-3659 (1988).

Kuroiwa et al., "Manipulation of Human Minichromosomes to Carry Greater Than Megabase-Sized Chromosome Inserts," *Nat. Biotechnol.* 18:1086-1090 (2000).

Lansford et al., "Ig Heavy Chain Class Switching in Rag-Deficient Mice," *Int. Immunol.* 10:325-332 (1998).

Lohka et al., "Formation In Vitro of Sperm Pronuclei and Mitotic Chromosomes Induced By Amphibian Ooplasmic Components," *Science* 220:719-721 (1983).

Lokha et al., "Induction of Nuclear Envelope Breakdown, Chromosome Condensation And Spindle Formation In Cell-Free Extracts," *J. Cell Biol.* 101:518-523 (1985).

Loupart et al., "Differential Stability of a Human Mini-Chromosome in Mouse Cell Lines," *Chromosoma* 107:255-259 (1998).

Martin et al., "Engraftment of Human Lymphocytes and Thyroid Tissue into Scid and Rag2-Deficient Mice: Absent Progression of Lymphocytic Infiltration," *J. Clin. Endocrinol. Metab.* 79:716-723 (1994).

Mazurler et al., "A Novel Immunodeficient Mouse Model—Rag2 x Common Cytokine Receptor Gamma Chain Double Mutants—Requiring Exogenous Cytokine Administration for Human Hematopoietic Stern Cell Engraftment," *J. Interferon cytokine Res.* 19:533-541 (1999).

Miake-Lye et al., "Induction of Early Mitotic Events in a Cell-Free System," *Cell* 41:165-175 (1985).

Mocikat, "Improving the Expression of Chimeric Antibodies Following Homologous Recombination in Hybridoma Cells," *J. Immunol. Methods* 225:185-189 (1999).

Newport, "Nuclear Reconstitution In Vitro: Stages of Assembly Around Protein-Free DNA," *Cell* 48:205-217 (1987).

Polejaeva et al., "New Advances in Somatic Cell Nuclear Transfer: Application in Transgenesis," *Theriogenology* 53:117-126 (2000).

Rideout et al., "Nuclear Cloning and Epigenetic Reprogramming of the Genome," *Science* 293:1093-1098 (2001).

Schnieke et al., "Human Factor IX Transgenic Sheep Produced By Transfer of Nuclei From Transfected Fetal Fibroblasts," *Science* 278:2130-2133 (1997).

Shen et al., "Human Mini-Chromosomes in Mouse Embryonal Stem Cells," *Hum. Mol. Genet.* 6:1375-1382 (1997).

Srikumaran et al., "Bovine X Mouse Hybridomas that Secrete Bovine Immunoglobulin G1," *Science* 220:522-524 (1983).

Steen et al., "A-Kinase Anchoring Protein (AKAP)95 Recruits Human Chromosome-Associated Protein (hCAP)-D2/Eg7 For Chromosome Condensation in Milotic Extract," *J. Cell Biol.* 149:531-536 (2000).

Steen et al., "Recruitment of Protein Phosphate 1 to the Nuclear Envelope By A-Kinase Anchoring Protein AKAP149 Is A Pre-Requisite For Nuclear Lamina Assembly," *J. Cell Biol.* 150:1251-1261 (2000).

Suprynowicz et al., "A Fractionated Cell-Free System for Analysis of Prophase Nuclear Disassembly," *J. Cell Biol.* 103:2073-2081 (1986).

Tomizuka et al., "Double Trans-Chromosomic Mice: Maintenance of Two Individual Human Chromosome Fragments Containing Ig Heavy and Kappa Loci and Expression of Fully Human antibodies," *Proc. Natl. Acad. Sci. USA* 97:722-727 (2000).

Wilson et al., "A Trypsin-Sensitive Receptor On Membrane Vesicles Is Required For Nuclear Envelope Formation in Vitro," *J. Cell Biol.* 107:57-68 (1988).

Yahata et al., "Reconstitution of Immune Systems in RAG2 / Mice by Transfer with Interleukin-12-Induced Splenic Hematopoietic Progenitor Cells," *Immunol. Lett.* 62:165-170 (1998).

Baguisi et al., "Production of Goats by Somatic Cell Nuclear Transfer," *Nature Biotechnology* 17:456-461 (1999).

Co et al., "Generation of Transgenic Mice and Germline Transmission of a Mammalian Artificial Chromosome Introduced into Embryos by Pronuclear Microinjection," *Chromosome Research* 8:183-191 (2000).

Eyestone et al., "Nuclear Transfer from Somatic Cells: Applications in Farm Animal Species," *Journal of Reproduction and Fertility* 54:489-497 (1999).

Grimes et al., "Engineering Mammalian Chromosomes," *Human Molecular Genetics* 7:1635-1640 (1998).

Langford et al., "Production of Pigs Transgenic Human Regulators of Complement Activation Using YAC Technology," *Transplantation Proceedings* 28:862-863 (1996).

Niemann et al., "Transgenic Livestock: Premises and Promises," *Animal Reproduction Science* 60-61:277-293 (2000).

Prather et al., "Development of the Techniques for Nuclear Transfer in Pigs," *Theriogenology* 51:487-198 (1999).

Sun et al., "Expressed Swine $V_H$ Genes Belong to a Small $V_H$ Gene Family Homologous to Human $V_H III$," *The Journal of Immumnology* 153:5618-5627 (1994).

Zhao et al., "Artiodactyl IgD: The Missing Link," *The Journal of Immunology* 169:4408-4416 (2002).

Zuelke, "Transgenic Modification of Cows Milk for Value-Added Processing," *Reproduction, Fertility, Development* 10:671-676 (1998).

Echelard et al., Cloned cattle engineered to carry an artificial chromosome encoding human Immunoglobulin genes are a significant leap toward the production of safer and more potent therapeutic antibodies, *Nat. Biotechnol.* 20:881-882, 2002.

Farrugia et al., Intravenous Immunoglobulin: regulatory perspectives on use and supply, *Trans. Med.* 11:63-74, 2001.

Fishwild et al., Highavidity human igGk monoclonal antibodies from a novel strain of minilocus transgenic mice, *Nat. Biotech.* 14:845-851, 1996.

Ishida et al., Production of human monoclonal and polyclonal antibodies in transchromo animals, *Clon. Stem Cells* 4:91-102, 2002.

Joziasse et al., Xenotransplantation: the importance of the Galα1,3Gal epitope in hyperacute vascular rejection, *Biochim. et BioPhys.* 1455:403-418, 1999.

Kuroiwa et al., Cloned transchromosomic calves producing human immunoglobulin, *Nat. Biotech.* 20:889-894, 2002.

Lonberg et al., Human antibodies from transgenic mice, *Intern. Rev. Immun.* 13:65-93, 1995.

Lucier et al., Multiple sites of Vγ diversification in cattle, *J. Immun.* 161:5438-5444, 1998.

Mendez et al., Functional transplant of megabase human immunoglobulin toci recapitulates human antibody response in mice, *Nat. Genet.* 15:146-156, 1997.

Raeber et al., Ectopic expression of prion protein (PrP) in T lymphocytes or hepatocytes of PrP knockout mice is insufficient to sustain prion replication, *Proc. Natl. Acad. Sci.* 96:3987-3992, 1999.

Sandrin et al., Recent advances in xenotransplantation, *Curr. Opin. in Immun.* 11:527-531, 1999.

Stiehm et al., Appropriate therapeutic use of immunoglobulin, *Trans. Med. Rev.* X:203-221, 1996.

Tomizuke et al., Functional expression and germline transmission of a human chromosome fragment in chimaeric mice, *Nat. Genet.* 16:133-143, 1997.

* cited by examiner

FIG. 3D

SEQ ID NO:47 ggtaccgaaaggcggccctgaacattctgcagtgagggagccgcactgagaaagctgcttcatcgccgggagggagccagc
cagctacgattgtgagcacgctcacagtgcacacggcatgtgcacggtctcagcttaaccaccttgaaggagtaactcattaaag
agcgtacgaatgcattgataaaatgcacctgagacaaattaatttcttaaacatcgactttgaaaatgaatataagtgagcagttgat
aggctctgaatgaaataccttccaacaggtgctgagaaccgccaggagcagggaacggactccccgtggagccccagaagg
agccagccctgatgatacctcggccctgggccctcctcacgctgggagagagccagctcctgttgttcatgcctggcctgtggtt
ctttgtcgtcatggccctcaaacaagcccacaggtcctggcctgagtccctcggcctgcgtgcagccgcccctcccctgctgg
aggcaccctgcctgccgtggagcccctcacccaacgttcccccgcctgatgggttgggccgcaaaggacaccgtttaaccaga
actgccttccaggagcctactgctgggaggcggccttctctgggaccaggtccactccactcccttggatagtcactgtcaggcc
cctggtggccccacaagaggcgtcctgggaagcccccagtctccttccagcccctgaaattgcctccctggagagccagatcac
cctcacccagctccctcccctggcccccagggtctcctctcccatcccaccgcccaccctaccctggcgttgccgtcacagctaa
cctgacctccctgggttcgagcgtgccgccgcccctgtcggcccccacctggaccccgcagcctatctctgagggctaatgc
ccctgtccctgccccgctgccagctgcccccctctttccaggcctttcctccgtgcctctccagtcctgcacctccctgcagcttca
cctgagacttcctttcaccctccaggcaccgtcttctggcctgcaggtgaggtctcgcgctccctcagggcacgatgtggctgca
cacacaccggccctcctcccgagtccctcctgcacacaccacgcgcacccgaggttgacaagccctgccgtggttgggattcc
gggaatggcggcagagaggggcggggtgtccttgggctggtggcagggtcctcatggatgcacacagcggccccggctc
aggccaccttgggaaaccagtcctgggatctgcaactcggccatgttcctgcatctggaccagccccaagacaccaccccggc
gtggcgccactggcctggggaggagacacatgtcccttcccatcagcaatgggttcagcactaggatatgcagcacacaggag
tgtggcttgggggtaaaaaaaccttcacgaggaagcggtttcacaaaataaagta

FIG. 3E

SEQ ID NO: 48 tctagacccaccagcctcagttgaggttaaatggacccaaagcatctcaacaatttgcccaagtcaagccagctcaatgggttcc
cttctgttcacccagtctcagcccaccatggtaacccagcataccccggttaagcccaggctagcccagcccagctgagcccag
ctcagctcagttcagcccagttcaatccagatcagcccaatccaggccagctcatcgagctcagttcagctcagctcaaccctctc
agcccagctcacctgctcagccaagctaagcccagttcagcccagctcagcttaacccagctcacccactctgcccagctcagc
ccagcccctgctcaactcagcccagcacagcccaacttggctcagctcagcttagcccagctcagcccagcttacccactccgcc
cagctcaaacagcccaggtcagcccaacctagctcagttcagcccagctcagcccagcccagctcagcccagctcacccactc
tgcccagctcaacacagcccagctcaacccagctcagctcagttcagcccagctcacccactctgcccagctcaggccagctc
aacccagcccagcccagctcactcattctgccaagctcagcccagctcaaccaggctcagctcagctcagccctgctga
ccnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnngctcagctcagcccagctcagcccagcccagcccagctcacacacttggcccacctcagccact
ccattcagctcagcccagctcaacccagctcagctcagctcaacctagctcagccaagctaacccactccacccagctcagccc
agctcgcccactctgcccagctcaacccagctcagctcagcccagcccagyccagcccagctcacccactccatccagccca
gcccagcccagctgagcccagctcaactcagcctaacccagctcagcccagcctaacccagctcagcccagcccaaccagct
agctgagcccagctcagtgcagctcaacccagctcagctcagctagcccagcccagctcaacctggctcaacccggctcagc
ccagctcacctgctgtaggtggcctgaaccgcgaacacagacatgaaagcccagtggttctgacgagaaagggtcagatcctg
gaccatggccacggctaaaggccctggtctgtggacactgcccagctgggctcatccctcccagcctcttcccgcttctcctcct
gggagcccgctcgcccccttcccctggtgcctgacacctccatcccgacaccaggcccagctggcccttctcccagctgtcagtc
accactaccctccactctgggtgaaaagcttgttggagactttagcttccctagagcatctcacaggctgagacacacttgccacc
ctcagagagaggccctgtctctgctgagcaggcagcgctgcttctctgggagaggagagcctgggcacacgtccctgggtcct
ggcctcctgggcacgtgccatgggcctgagatcccgccccgagtctaaaagagtcctggtgactaactgctctctggcaaatgt
cctcattaaaaaccacaggaaatgcatcttatctgaacctgctcccaattctgtctttatcacaaagttctgctgagaaagaggatac
tctctagcacagagaccatctgaacccaaagctgcattgaacacctaagtgtggacgcaggaagtggtccctgtgggtgtgaa
gcaccccggcatcgcaggcagtaggtaaagacagattcccttcaagtagaaacaaaaacaactcatacaaacatccctgggc
agtgagtctggctgcaccggctcctggtccctggcatgtccctgggctctctgacctgggcggattcctccgaatcccttcgctg
tgttaactcgtgacctgcctactggcctgggggcagaggccaggcccacacgtccccaggtgtgggcagtcccaggagaccc
cccagccttggcgagcctggggactcagagcagagactgtccctccagacggtcccaggccccgctgactgccgccccacc
gggcatcctctcaatcccccagctagtagtgtagcagagtaactcacgacgaatgccccgtttcacccaagtctgtcctgagat
gggtacc

FIG. 3G

SEQ ID NO: 60

```
  1 atgagattcc ctgctcagct cctggggctc ctcctgctct gggtcccagg
 51 atccagtggg gatgttgtgc tgacccagac tcccctctcc ctgtctatca
101 tccctggaga gacggtctcc atctcctgca gtctactca gagtctgaaa
151 tatagtgatg gaaaaaccta tttgtactgg cttcaacata aaccaggcca
201 atcaccacag cttttgatct atgctgtttc cagccgttac actggggtcc
251 cagacaggtt cactggcagt gggtcagaaa cagatttcac acttacgatc
301 aacagtgtgc aggctgagga tgttggagtc tattactgtc ttcaaacaac
351 atatgtccca aatactttcg gccaaggaac caaggtagag atcaaaaggt
401 ctgatgctga ccatccgtc ttcctcttca accatctga tgagcagctg
451 aagaccggaa ctgtctctgt cgtgtgcttg gtgaatgatt tctaccccaa
501 agatatcaat gtcaagtgga agtggatgg ggttactcag agcagcagca
551 acttccaaaa cagtttcaca gaccaggaca gcaagaaaag cacctacagc
601 ctcagcagca tcctgacact gcccagctca gagtaccaaa gccatgacgc
651 ctatacgtgt gaggtcagcc acaagagcct gactaccacc ctcgtcaaga
701 gcttcagtaa gaacgagtgt tag
```

1. Bovine genomic DNA (negative
2. Fetus 5968 genomic DNA at 56 days
3. Fetus 5983 genomic DNA at 56 days
4. Fetus 6032 genomic DNA at 58 days
5. Fetus 6045 genomic DNA at 56 days
6. Fetus 5846 genomic DNA at 79 days
7. Fetus 5996 genomic DNA at 77 days

| Fetus | Clone | IgH | Ig λ |
|-------|-------|-----|------|
| 5968  | B4-2  | Pos | Pos  |
| 5983  | B2-13 | Neg | Neg  |
| 6032  | B4-8  | Pos | Pos  |
| 6045  | B2-22 | Pos | Pos  |
| 5846  | B4-8  | Neg | Neg  |
| 5996  | B4-2  | Pos | Neg  |

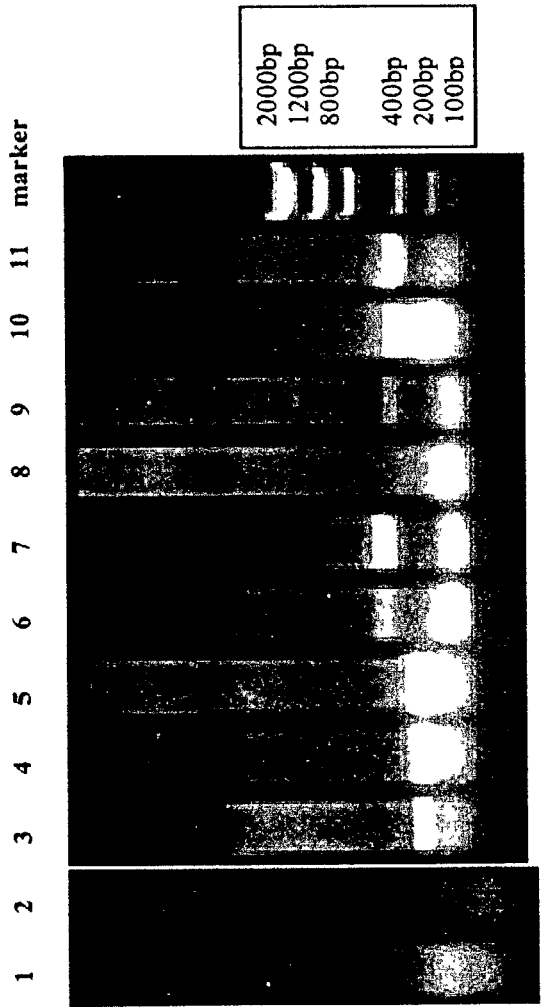

FIG. 6

1. Human mu constant region in bovine liver cDNA from fetus 5996.
2. Human mu constant region in bovine brain cDNA from fetus 5996.
3. Human mu constant region in bovine spleen cDNA from fetus 5996.
4. Human mu constant region in human spleen cDNA.
5. Human mu constant region in mouse spleen cDNA with HAC.
6. Bovine rearranged Cmu heavy chain in bovine spleen cDNA from fetus 5996.
7. Bovine rearranged Cmu heavy chain in human spleen cDNA.
8. Bovine rearranged Cmu heavy chain in mouse spleen cDNA with HAC.
9. GAPDH primers in bovine spleen cDNA from fetus 5996.
10. GAPDH primers in bovine liver cDNA
11. GAPDH primers in mouse spleen cDNA with HAC.

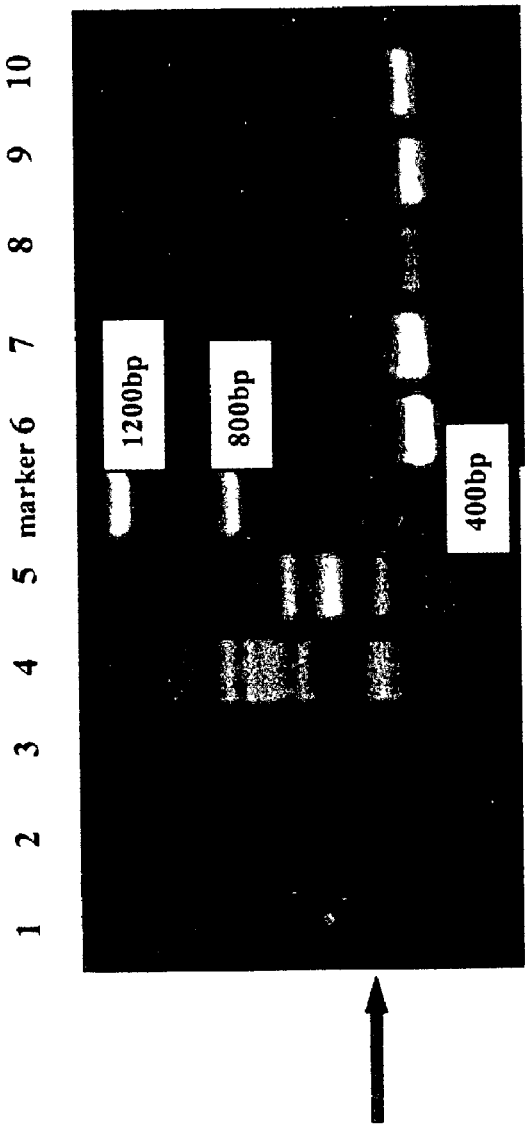

FIG. 8

1. Human rearranged Cmu heavy chain in mouse spleen cDNA with HAC (+ control).
2. Human rearranged Cmu heavy chain in bovine liver cDNA from fetus.
3. Human rearranged Cmu heavy chain in bovine brain cDNA from fetus 5996.
4. Human rearranged Cmu heavy chain in human spleen cDNA (+ control).
5. Human rearranged Cmu heavy chain in bovine spleen cDNA from fetus 5996.
6. GAPDH primers in bovine spleen cDNA from fetus 5996.
7. GAPDH primers in mouse spleen cDNA with HAC
8. GAPDH primers in bovine brain cDNA from fetus 5996.
9. GAPDH primers in bovine liver cDNA from fetus 5996.
10. GAPDH primers positive control.

1. Mouse spleen (negative control)
2. Bovine spleen (negative control)
3. Fetus 5996 brain
4. Fetus 5996 liver
5. Fetus 5996 liver
6. Fetus 5996 spleen
7. Fetus 5996 spleen
8. Δ HAC-chimeric mouse spleen (positive control)
9. Human spleen (positive control).

← Unspliced genomic fragment
← Spliced transcript

1. Mouse spleen (negative control)
2. Bovine spleen (negative control)
3. Fetus 5996 brain
4. Fetus 5996 liver
5. Fetus 5996 liver
6. Fetus 5996 spleen
7. Fetus 5996 spleen
8. ΔHAC-chimeric mouse spleen (positive control)
9. Human spleen (positive control)

FIG. 11A

SEQ ID NO: 49
5'
GGGAAGGAAGTCCTGTGCGACCANCCAACGGCCACGCTGCTCGTATCCGACG
GGGAATTCTCACAGGAGACGAGGGGGAAAAGGGTTGGGGCGGATGCACTCC
CTGAGGAGACGGTGACCAGGGTTCCNTGGCCCCAGNNGTCAAA3'

FIG. 11B

SEQ ID NOs: 50 and 51

V-D-J region          |→ constant mu region

Subject: 5'
tttgactactggggccagggaaccctggtcaccgtctcctcagggagtgcatccgcccca
------nn---------n----------------------------------
Query Subject:
acccttttcccectcgtctcctgtgagaattccccgtcggatacgagcagcgtggccgtt
----------------------------------------------------
Query Subject: 5'
ggctgcctcgcacaggacttccttcccgactccatcactttctcctg 3'
--n---g------------------ Cmu1 primer

FIG. 12A

SEQ ID NOs: 52 and 53

```
                    10              19              28              37              46              55
5' GGA GGC TTG GTC GTC AAG CCT GGA GGG TCC CTG AGA CTC TCC TGT GCA GCC TCT GGA
    G   G   L   V   V   K   P   G   G   S   L   R   L   S   C   A   A   S   G 64              73              82              91              100             109
TTC ACC TTC AGT GAC TAC TAC ATG AGC TGG ATC CGC CAG GCT CCA GGG AAG GGG
  F   T   F   S   D   Y   Y   M   S   W   I   R   Q   A   P   G   K   G 118             127             136             145             154             163
CTG GAG TGG GTT TCA TAC ATT AGT AGT GGT AGT ACC ATA TAC TAC GCA GAC
  L   E   W   V   S   Y   I   S   S   G   S   T   I   Y   Y   A   D
                          VH3-11
                                        190                     208             217
TCT GTG AAG GGC CGA TTC ACC ATC TCC AGG GAC AAC GCC AAG AAC TCA CTG TAT
  S   V   K   G   R   F   T   I   S   R   D   N   A   K   N   S   L   Y 226             235             244             253             262             271
CTG CAA ATG AAC AGC CTG AGA GCC GAG GAC ACG GCT GTG TAT TAC TGT GCG AGA
  L   Q   M   N   S   L   R   A   E   D   T   A   V   Y   Y   C   A   R 280             289             298             307             316             325
ATA ACT GGG GAT GCT TTT GAT ATC TGG GGC CAA GGG ACA ATG GTC ACC GTC TCT
  I   T   G   D   A   F   D   I   W   G   Q   G   T   M   V   T   V   S
        D7-27                              JH3
    334             343             352             361             370             379
TCA GGG AGT GCA TCC GCC CCA ACC CTT TTC CCC CTC GTC TCC TGT GAG AAT TCC
  S   G   S   A   S   A   P   T   L   F   P   L   V   S   C   E   N   S
                                                            Cμ
    388
CCG TCG GAT ACG AGC 3'
  P   S   D   T   S
```

FIG. 12B

SEQ ID NOs: 54 and 55

5' GTG GAG TCT GGG GGA GGC TTG GTA CAG CCT GGG AGG TCC CTG AGA CTC TCC TGT
     V   E   S   G   G   G   L   V   Q   P   G   R   S   L   R   L   S   C

GCA GCG TCA GGA TTC ACC TTC AGG AAC TTT GGC ATG CAC TGG GTC CGC CAG GCT
 A   A   S   G   F   T   F   R   N   F   G   M   H   W   V   R   Q   A
                           VH3-33

CCA GGC AAG GGG CTG GAG TGG GTG GTG ACA GTT ATA TGG TAT GAC GGA AGT AAT CAA
 P   G   K   G   L   E   W   V   V   T   V   I   W   Y   D   G   S   N   Q

TAC TAT ATA GAC TCC GTG AAG GGC CGA TTC ACC ATC TCC AGA GAC AAT TCC AAG
 Y   Y   I   D   S   V   K   G   R   F   T   I   S   R   D   N   S   K

AAC ATG TTG TAT CTG CAA ATG AAC AGC CTG AGA GCC GAG GAT ACG GCT GTC TAT
 N   M   L   Y   L   Q   M   N   S   L   R   A   E   D   T   A   V   Y

TAC TGT GCG AGA GAT CGC AAT GGC CTG AAG TAC TTC GAT CTC TGG GGC CGT GGC
 Y   C   A   R   D   R   N   G   L   K   Y   F   D   L   W   G   R   G
              D6-39 ? N addition            JH2

ACC CTG GTC ACT GTC TCA TCA GGG AGT GCA TCC GCC TCC AGC AGC CCT TCC CCT
 T   L   V   T   V   S   S   G   S   A   S   A   P   T   L   F   P L

GTC TCC TGT GAG AAT TCC CCG TCG GAT ACG AGC 3'
 V   S   C   E   N   S   P   S   D   T   S
                                            Cμ

| Fetus | Clone | IgH | Igλ |
|-------|-------|-----|-----|
| 5580  | 412   | Pos | Pos |
| 5848  | 214   | Neg | Neg |

1. Bovine genomic DNA (negative control)
2. Fetus 5580 genomic DNA (Igλ)
3. Fetus 5580 genomic DNA (Igλ)
4. Fetus 5848 genomic DNA (Igλ)
5. Fetus 5848 genomic DNA (Igλ)
6. Positive control (Human genomic DNA)
7. Bovine genomic DNA (negative control)
8. Fetus 5580 genomic DNA (IgH)
9. Fetus 5580 genomic DNA (IgH)
10. Fetus 5848 genomic DNA (IgH)
11. Fetus 5848 genomic DNA (IgH)
12. Positive control (Human genomic DNA)

1. Bovine genomic DNA (negative control)
2. Fetus 5442A genomic DNA (91 day)
3. Fetus 5442A genomic DNA (91 day)
4. Fetus 5442B genomic DNA (91 day)
5. Fetus 5442B genomic DNA (91 day)
6. Fetus 5968 genomic DNA (56 day; positive control)
7. Human genomic DNA (positive control)

1. Low Mass Ladder: 2.0, 1.2, 0.8, 0.4, 0.2 0.1kb
2. Normal Bovine spleen cDNA negative
3. ΔΔHAC 5868A spleen
4. empty
5. Hi Lo 0.2, 0.1kb
6. Tc Mouse HAC spleen cDNA positive
7. GAPDH product from 5868A spleen cDNA
8. GAPDH product from normal bovine cDNA 1. Bovine spleen (negative control)
2. Fetus 5442A brain
3. Fetus 5442A liver
4. Fetus 5442A spleen
5. Fetus 5442A spleen
6. ΔHAC-chimeric mouse spleen (positive control)

1. Hi-Lo MW:2.0,1.5,1.4,1.0,0.7,0.5 kb
2. ΔΔHAC 5868A fetal brain cDNA
3. ΔΔHAC 5868A fetal liver cDNA
4. ΔΔHAC 5868A fetal spleen cDNA
5. Low Mass Ladder
6. Tc Mouse HAC spleen cDNA positive control (530bp)
7. Low Mass Ladder
8. GAPDH ΔΔHAC 5868A brain cDNA
9. Low Mass Ladder
10. GAPDH ΔΔHAC 5868A liver cDNA

FIG. 20

SEQ ID NOs: 56 and 57

```
5' ACC CTC CTC ACT CAC TGT GCA GGG TCC TGG GCC CAG TCT GTG CTG ACT CAG CCA
     T   L   L   T   H   C   A   G   S   W   A   Q   S   V   L   T   Q   P

CCC TCA GCG TCT GGG ACC CCC GGG CAG AGG GTC ACC ATC TCT TGT TCT GGA AGC
    P   S   A   S   G   T   P   G   Q   R   V   T   I   S   C   S   G   S

AGC TCC AAC ATC GGA AGT AAT TAT GTA TAC TGG TAC CAG CAG CTC CCA GGA ACG    V1-17
    S   S   N   I   G   S   N   Y   V   Y   W   Y   Q   Q   L   P   G   T

GCC CCC AAA CTC CTC ATC TAT AGG AAT AAT CAG CGG CCC TCA GGG GTC CCT GAC
    A   P   K   L   L   I   Y   R   N   N   Q   R   P   S   G   V   P   D

CGA TTC TCT GGC TCC AAG TCT GGC ACC TCA GCC TCC CTG GCC ATC AGT GGG CTC
    R   F   S   G   S   K   S   G   T   S   A   S   L   A   I   S   G   L

CGG TCC GAG GAT GAG GCT GAT TAT TAC TGT GCA GCA TGG GAT GAC AGC CTG AGT
    R   S   E   D   E   A   D   Y   Y   C   A   A   W   D   D   S   L   S

GGT CTT TTC GGC GGA GGG ACC AAG CTG ACC GTC CTA GGT CAG CCC AAG GCT GCC
    G   L   F   G   G   G   T   K   L   T   V   L   G   Q   P   K   A   A
                                         JL3

CCC TCG GTC ACT CTG TTC CCA CCC TCC TCT GAG GAG CTT CAA GCC AAC AAG GCC
    P   S   V   T   L   F   P   P   S   S   E   E   L   Q   A   N   K   A
                                                           Cλ

ACA CTG GTG 3'
    T   L   V
```

FIG. 21

SEQ ID NOs: 58 and 59

```
5' AGT TGG ACC CCT CTC TGG CTC ACT CTC TTC ACT CTT TGC ATA GGT TCT
    S   W   T   P   L   W   L   T   L   F   T   L   C   I   G   S

GTG GTT TCT TCT GAG CTG ACT CAG GAC CCT GCT GTG TCT GTG GCC TTG GGA CAG
 V   V   S   S   E   L   T   Q   D   P   A   V   S   V   A   L   G   Q

ACA GTC AGG ATC ACA TGC CAA GGA CAG AGC CTC AGA AGC TAT TAT GCA AGC TGG    V2-13
 T   V   R   I   T   C   Q   G   D   S   L   R   S   Y   Y   A   S   W

TAC CAG CAG AAG CCA GGA CAG GCC CCT GTA CTT GTC ATC TAT GGT AAA AAC AAC
 Y   Q   Q   K   P   G   Q   A   P   V   L   V   I   Y   G   K   N   N

CGG CCC TCA GGG ATC CCA GAC CGA TTC TCT GGC TCC AGC TCA GGA AAC ACA GCT
 R   P   S   G   I   P   D   R   F   S   G   S   S   S   G   N   T   A

TCC TTG ACC ATC ACT GGG GCT CAG GCG GAA GAT GAG GCT GAC TAT TAC TGT AAC
 S   L   T   I   T   G   A   Q   A   E   D   E   A   D   Y   Y   C   N

TCC CGG GAC AGC AGT GGT AAC CAT CTG GTA TTC GGC GGA GGG ACC AAG CTG ACC    JL2
 S   R   D   S   S   G   N   H   L   V   F   G   G   G   T   K   L   T

GTC CTA GGT CAG CCC AAG GCT GCC CCC TCG GTC ACT CTG TTC CCA CCC TCC TCT
 V   L   G   Q   P   K   A   A   P   S   V   T   L   F   P   P   S   S
                                                                       Cλ

GAG GAG CTT CAA GCC AAC AAG GCC ACA CTG GTG 3'
 E   E   L   Q   A   N   K   A   T   L   V
```

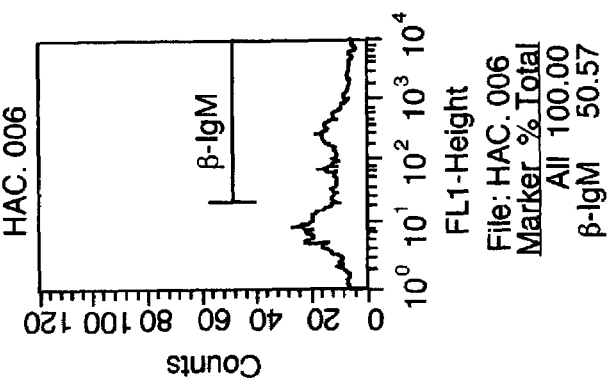
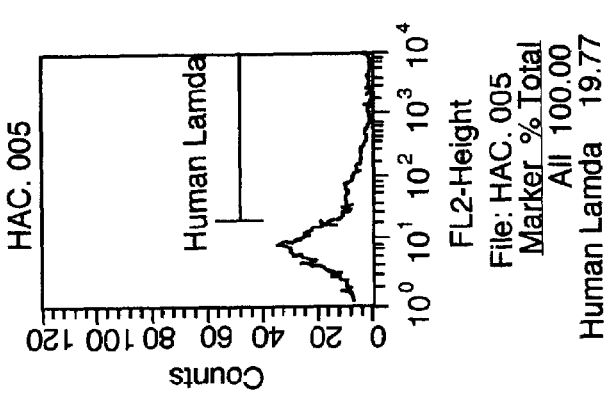
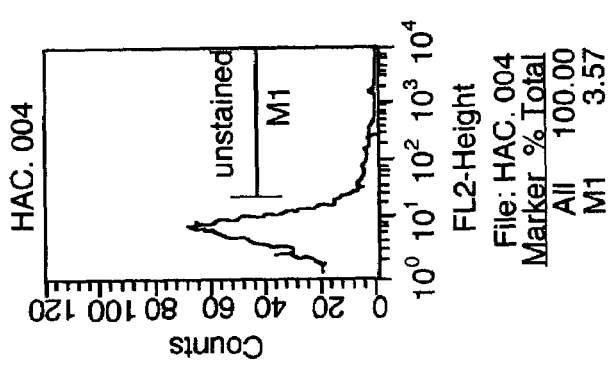
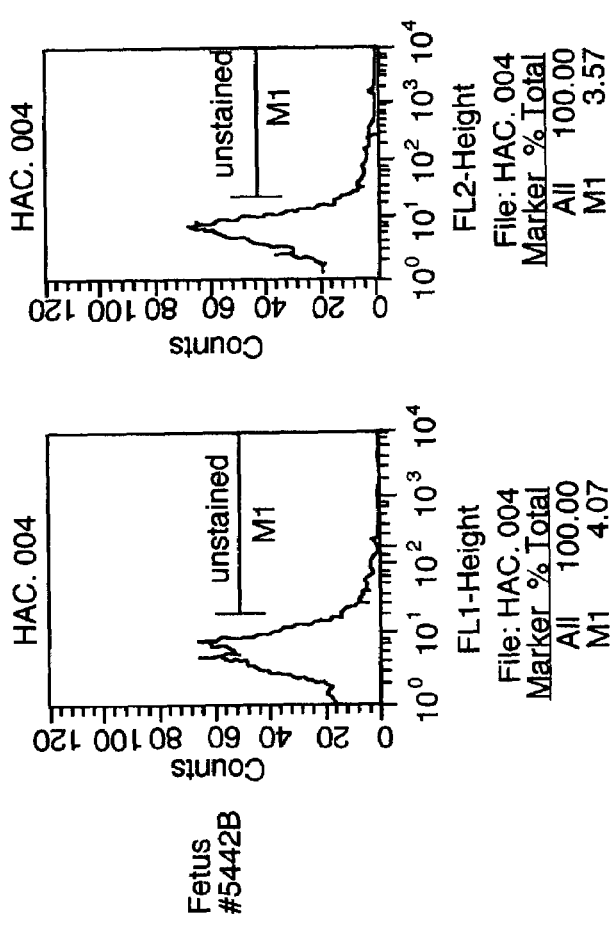

FIG. 27

NT, ET and pregnancies :Delta HAC regenerated fibroblasts

| Cell line ID | Total NTs in culture | No of Blast (%) | No of Blast Transferred | No Recips | Pregnancy status 40 d | 60 d | 90 d | 120 d | 150 d | 180 d | 210 d |
|---|---|---|---|---|---|---|---|---|---|---|---|
| D5968 | 174 | 34 (28) | 27 | 17 | 3 | 3 | 3 | 3 | 3 | 3 | 3 |
| D6045 | 215 | 10 (7) | 8 | 4 | 1 | 1 | 1 | 1 | 1 | 1 | |
| D6045 | 122 | 20 (23) | 12 | 9 | 1 | 0 | 0 | 0 | 0 | 0 | |
| D6032 | 161 | 18 (16) | 14 | 7 | 3 | 3 | 3 | 2 | 2 | 2 | |
| D6032 | 188 | 15 (11) | 11 | 11 | 3 | 0 | 0 | 0 | 0 | 0 | |
| D6032 | 198 | 20 (14) | 16 | 10 | 1 | 1 | 1 | 1 | | | |
| D6032 | 200 | 17 (12) | 12 | 8 | 2 | 2 | 2 | 2 | | | |
| D6032 | 180 | 11 (9) | 10 | 5 | 3 | 1 | 1 | 0 | | | |
| D6032 | 135 | 22 (23) | 22 | 11 | 2 | 1 | 1 | 1 | | | |
| D5968 | 140 | 35 (36) | 25 | 13 | 2 | 2 | 1 | | | | |
| D5968 | 180 | 30 (24) | 26 | 13 | 2 | 2 | 1 | | | | |
| D6045 | 170 | 46 (39) | 32 | 16 | 4 | | | | | | |
| D6045 | 80 | 7 (13) | 1 | 1 | 0 | | | | | | |
| D6045 SLOT | 108 | 9 (12) | 3 | 2 | 1 | | | | | | |
| D6045 | 76 | 8 (15) | 2 | 1 | 0 | | | | | | |
| D6045 SLOT | 128 | 12 (13) | 7 | 5 | 0 | | | | | | |
| D6045 | 47 | 6 (18) | 5 | 3 | 2 | | | | | | |
| D6045 SLOT | 112 | 3 (4) | 3 | 2 | 2 | | | | | | |
| D6045 | 120 | 28 (33) | 18 | 9 | | | | | | | |
| D6045 SLOT | 100 | 11 (16) | 2 | 1 | | | | | | | |
| D6045 | 76 | 15 (27) | 16 | 8 | | | | | | | |
| D6045 SLOT | 91 | 0 | 2 | 1 | | | | | | | |
| D6045 | 96 | 16 (23) | 10 | 5 | | | | | | | |
| D6045 SLOT | 104 | 16 (22) | 10 | 5 | | | | | | | |
| D5968 | 128 | 24 (27) | 8 | 4 | | | | | | | |
| D5968 SLOT | 65 | 10 (22) | 6 | 4 | | | | | | | |
| D5968 | 120 | 28 (33) | 14 | 7 | | | | | | | |
| D5968 SLOT | 95 | 13 (19) | 6 | 3 | | | | | | | |
| D5968 | 96 | 17 (25) | 20 | 10 | | | | | | | |
| D5968 SLOT | 93 | 14 (22) | 12 | 6 | | | | | | | |
| D | 13 | 1 (11) | 1 | 3 | | | | | | | |
| SLOT | 63 | 8 (18) | 8 | 3 | | | | | | | |
| D | 108 | 4 (5) | 4 | 3 | | | | | | | |
| SLOT | 100 | 1 (1) | 1 | 3 | | | | | | | |
| D | 90 | 10 (16) | 10 | 6 | | | | | | | |
| SLOT | 110 | 13 (17) | 13 | 6 | | | | | | | |
| D | 90 | 10 (16) | 10 | 1 | | | | | | | |
| SLOT | 83 | 5 (9) | 5 | 1 | | | | | | | |
| D | 105 | 20 (27) | 20 | 9 | | | | | | | |
| SLOT | 76 | 7 (13) | 7 | 2 | | | | | | | |
| D | 88 | 7 (11) | 7 | 4 | | | | | | | |
| SLOT | 93 | 9 (14) | 9 | 4 | | | | | | | |
| D | 85 | 20 (33) | 20 | 10 | | | | | | | |
| SLOT | 77 | 4 (7) | 4 | 2 | | | | | | | |
| | 4987 | 515 (19) | 481 | 258 | | | | | | | |

Summary

| Preg Status | No of Pregnancies |
|---|---|
| > 40 d | 9 |
| > 90 d | 2 |
| > 120 d | 4 |
| > 180 d | 3 |
| > 210 d | 3 |
| Total | 21 |

TRANSGENIC BOVINE COMPRISING HUMAN IMMUNOGLOBULIN LOCI AND PRODUCING HUMAN IMMUNOGLOBULIN

CROSS-REFERENCE TO RELATED APPLICATIONS

This application claims the benefit of the filing date of U.S. provisional patent application 60/311,625, filed Aug. 9, 2001 and U.S. provisional patent application 60/256,458, filed Dec. 20, 2000, and is a continuation-in-part of U.S. utility application Ser. No. 09/714,185, filed Nov. 17, 2000, now abandoned which claims priority to U.S. provisional patent application 60/166,410, filed Nov. 19, 1999.

FIELD OF THE INVENTION

The present invention is a genetically modified ungulate that contains either part or all of a xenogenous antibody gene locus, which undergoes rearrangement and expresses a diverse population of antibody molecules. In particular, the xenogenous antibody gene may be of human origin. In addition, the present invention provides for an ungulate in which expression of the endogenous antibody genes is either reduced or eliminated. The genetic modifications in the ungulate (for example, bovine) are made using a combination of nuclear transfer and molecular techniques. These cloned, transgenic ungulates provide a replenishable, theoretically infinite supply of xenogenous polyclonal antibodies, particularly human antibodies, which have use, e.g. as therapeutics, diagnostics and for purification purposes.

BACKGROUND OF THE INVENTION

In 1890, Shibasaburo Kitazato and Emil Behring reported an experiment with extraordinary results; particularly, they demonstrated that immunity can be transferred from one animal to another by taking serum from an immune animal and injecting it into a non-immune one. This landmark experiment laid the foundation for the introduction of passive immunization into clinical practice. Today, the preparation and use of human immunoglobulin (Ig) for passive immunization is standard medical practice. In the United States alone, there is a $1,400,000,000 per annum market for human Ig, and each year more than 16 metric tons of human antibody is used for intravenous antibody therapy. Comparable levels of consumption exist in the economies of most highly industrialized countries, and the demand can be expected to grow rapidly in developing countries. Currently, human antibody for passive immunization is obtained from the pooled serum of human donors. This means that there is an inherent limitation in the amount of human antibody available for therapeutic and prophylactic usage. Already, the demand exceeds the supply and severe shortfalls in availability have been routine.

In an effort to overcome some of the problems associated with the inadequate supply of human Ig, various technologies have been developed. For example, the production of human Ig by recombinant methods in tissue culture is routine. Particularly, the recombinant expression of human Ig in CHO expression systems is well known, and is currently utilized for the production of several human immunoglobulins (Igs) and chimeric antibodies now in therapeutic use.

Mice retaining an unrearranged human immunoglobulin gene have been developed for the production of human antibodies (e.g., monoclonal antibodies) (see, for example, WO98/24893; WO96/33735; WO 97/13852; WO98/24884; WO97/07671(EP 0843961); U.S. Pat. No. 5,877,397; U.S. Pat. No. 5,874,299; U.S. Pat. No. 5,814,318; U.S. Pat. No. 5,789,650; U.S. Pat. No. 5,770,429; U.S. Pat. No. 5,661,016; U.S. Pat. No. 5,633,425; U.S. Pat. No. 5,625,126; U.S. Pat. No. 5,569,825; and U.S. Pat. No. 5,545,806).

Additionally, WO00/10383 (EP 1106061) describes modifying a human chromosome fragment and transferring the fragment into certain cells via microcell fusion.

Further, WO01/35735 describes a bovine IgM heavy chain knockout.

U.S. Pat. No. 5,849,992 issued Dec. 15, 1998 to Meade et al., as well as U.S. Pat. No. 5,827,690 issued Oct. 27, 1998 to Meade et al., describe the production of monoclonal antibodies in the milk of transgenic animals including mice, sheep, pigs, cows, and goats wherein the transgenic animals expressed human Ig genes under the control of promoters that provide for the expression of the antibodies in mammary epithelial cells. Essentially, this results in the expression of the antibodies in the milk of such animals, for example a cow.

However, notwithstanding what has been previously reported, improved methods and enhanced transgenic animals, especially cows, that produce antibodies (particularly, polyclonal antibodies) of desired species, particularly human Igs, in the bloodstream and which produce an array of different antibodies which are specific to a desired antigen would be highly desirable. Most especially, the production of human Igs in ungulates, such as cows, would be particularly beneficial given that (1) cows could produce large quantities of antibody, (2) cows could be immunized with human or other pathogens and (3) cows could be used to make human antibodies against human antigens. The availability of large quantities of polyclonal antibodies would be advantageous for treatment and prophylaxis for infectious disease, modulation of the immune system, removal of human cells, such as cancer cells, and modulation of specific human molecules. While human Ig has been expressed in mice, it is unpredictable whether human Ig will be fractionally rearranged and expressed in bovines, or other ungulates, because of differences in antibody gene structure, antibody production mechanism, and B cell function. In particular, unlike mice, cattle and sheep differ from humans in their immunophysiology (Lucier et al., J. Immunol. 161: 5438, 1998; Pamg et al., J. Immunol. 157:5478, 1996; and Butler, Rev. Sci. Tech. 17:43, 2000). For example antibody gene diversification in bovines and ovines relies much more on gene conversion than gene rearrangement as in humans and mice. Also, the primary location of B cells in humans and mice is in the bone marrow, whereas in bovines and ovines B cells are located in the illeal Peyer's patch. Consequently, it would have been difficult, if not impossible, prior to the present invention, to predict whether immunoglobulin rearrangement and diversification of a human immunoglobulin loci would take place within the bovine (or other ungulate) B cell lineage. In addition, it would also have been unpredictable whether a bovine would be able to survive, i.e., elicit its normal immune functions, in the absence of its endogenous Ig or with interference from human antibodies. For example, it is not certain if bovine B cells expressing human Ig would correctly migrate to the illeal Peyer's Patch in bovines because this does not happen in humans. Also, it is not clear if human Fc receptor function; which mediates complement activation, induction of cytokine release, and antigen removal; would be normal in a bovine system.

BRIEF DESCRIPTION OF THE INVENTION

It is an object of the invention to produce a transgenic ungulate (for example, a transgenic bovine) that rearranges and expresses a human, or other species Ig gene locus. Preferably, this is accomplished by stably introducing a human chromosome fragment containing human Ig genes, in order to produce a transgenic ungulate (for example, bovine) having B cells that produce human or another species Ig, in addition to or in lieu of endogenous Igs. This may also be accomplished by integrating a nucleic acid encoding a xenogenous immunoglobulin chain or xenogenous antibody into a chromosome of an ungulate. It is a further object of the present invention to produce transgenic ungulates (for example, transgenic bovines) wherein the expression of endogenous Ig has been reduced or knocked out. For example, a nonsense or deletion mutation may be introduced into a nucleic acid encoding an endogenous immunoglobulin chain or antibody.

It is a more specific object of the invention to produce a transgenic ungulate (for example, a transgenic bovine) wherein the constant region exon of the light chain loci and/or the mu constant regions exons have been knocked out, and an artificial chromosome containing a gene locus encoding another species' immunoglobulin, preferably human, has been stably incorporated.

It is a more specific object of the invention to produce a cloned ungulate (for example, a cloned bovine) by the use of nuclear transfer and homologous recombination procedures wherein the endogenous constant region exon of the light chain loci and/or the mu constant region exons of the heavy chain locus have been knocked out, and an artificial chromosome(s) comprising xenogenous heavy and light chain Ig genes, preferably a human artificial chromosome(s) containing human heavy and light chain Ig loci, has been stably introduced, resulting in a transgenic ungulate which produces Ig of another species, preferably human, and which does not produce its endogenous Ig.

It is another object of the invention to produce an ungulate (for example, a bovine) somatic or embryonic stem (ES) cell, preferably a fibroblast or B cell, and more preferably a male somatic cell, wherein one or both alleles of the endogenous IgM heavy chain gene has been mutated, for example, disrupted by homologous recombination. It is a related object of the invention to produce a cloned ungulate (for example, bovine) fetus and offspring wherein one or both alleles of the IgM heavy chain gene locus has been mutated, for example, disrupted by homologous recombination.

It is still another object of the invention to produce an ungulate (for example, a bovine) somatic or ES cell, preferably a fibroblast or B cell, e.g., a female or male somatic cell, wherein one allele of the IgM heavy chain gene has been mutated, for example, disrupted by homologous recombination.

It is a related object of the invention to produce a cloned (ungulate, for example, bovine) fetus or offspring wherein one allele of the endogenous heavy chain IgM gene has been mutated, for example, disrupted by homologous recombination.

It is still another object of the invention to produce male and female heavy and light chain hemizygous knockout (M and F Hemi H/L) fetuses and ungulate calves by mating male and female ungulates (for example, bovines) which respectively contain a mutation, for example, a disruption of one allele of the endogenous IgM or a disruption of one allele of an Ig light chain or by sequential homologous recombination.

It is still another object of the invention to produce a homozygous knockout (Homo H/L) fetus wherein both heavy chain alleles of the IgM gene have been disrupted and both alleles of the Ig light chain have been disrupted by sequential homologous recombination or by mating of the aforementioned male and female heavy and light chain hemizygous knockouts (M and F Hemi H/L).

It is another specific object of the invention to insert a nucleic acid (for example, an artificial chromosome) that contains genes necessary for the functional expression of non-ungulate Igs or their heavy or light chains. Preferably, these Igs are human Igs produced by introduction of nucleic acid encoding these Igs or Ig chains into a Homo or a Hemi H/L ungulate (for example, bovine) somatic cell, preferably a fibroblast, and producing cloned ungulates (for example, cloned bovines) wherein the nucleic acid (for example, human artificial chromosome DNA) is transmitted into the germ line.

It is still another object of the invention to introduce an artificial chromosome, preferably a human artificial chromosome (HAC), that contains genes that provide for Ig expression into the aforementioned homozygous knockout (Homo H/L) cells and generate ungulates (for example, cattle) by nuclear transfer which express non-ungulate Igs, preferably human Igs, in response to immunization and which undergo affinity maturation.

As used herein, by "artificial chromosome" is meant a mammalian chromosome or fragment thereof which has an artificial modification such as the addition of a selectable marker, the addition of a cloning site, the deletion of one or more nucleotides, the substitution of one or more nucleotides, and the like. By "human artificial chromosome (HAC)" is meant an artificial chromosome generated from one or more human chromosome(s). An artificial chromosome can be maintained in the host cell independently from the endogenous chromosomes of the host cell. In this case, the HAC can stably replicate and segregate along side endogenous chromosomes. Alternatively, it may be translocated to, or inserted into, an endogenous chromosome of the host cell. Two or more artificial chromosomes can be introduced to the host cell simultaneously or sequentially. For example, artificial chromosomes derived from human chromosome #14 (comprising the Ig heavy chain gene), human chromosome #2 (comprising the Ig kappa chain gene), and human chromosome #22 (comprising the Ig lambda chain gene) can be introduced. Alternatively, an artificial chromosome(s) comprising both a xenogenous Ig heavy chain gene and Ig light chain gene, such as ΔHAC or ΔΔHAC, may be introduced. Preferably, the heavy chain loci and the light chain loci are on different chromosome arms (i.e., on different side of the centromere). In still other preferred embodiments, the total size of the HAC is less than or equal to approximately 10, 9, 8, or 7 megabases.

It is still another object of the invention to provide a source of human or other Ig for passive immunization derived from a transgenic ungulate (for example, a transgenic bovine) that contains and expresses Ig genes carried on an introduced nucleic acid (for example, an artificial chromosome, and preferably a human artificial chromosome (HAC)) containing human Ig heavy and light chain genes. In the present invention, these nucleic acids (for example, HACs) include naturally arranged segments of human chromosomes (human chromosomal fragments) or artificial chromosomes that comprise artificially engineered human chromosome fragments, i.e., they may be rearranged relative to the human genome.

It is yet another object of the invention to produce hybridomas and monoclonal antibodies using B cells derived from the above-described transgenic ungulates (for example, transgenic bovines).

It is still another object of the invention to produce ungulate antiserum or milk that includes polyclonal human Ig. Such human Ig, preferably human IgG, may be used as intravenenous immunoglobulin (IVIG) for the treatment or prevention of disease in humans. The polyclonal human Ig are preferably reactive against an antigen of interest.

It is yet another object of the invention to produce a transgenic ungulate with one or more mutations in an endogenous gene or genes. The transgenic ungulate is produced by inserting a cell, a chromatin mass from a cell, or a nucleus from a cell into an oocyte. The cell has a first mutation in an endogenous gene that is not naturally expressed by the cell. The oocyte or an embryo formed from the oocyte is transferred into the uterus of a host ungulate under conditions that allow the oocyte or the embryo to develop into a fetus. Preferably, the fetus develops into a viable offspring. In other preferred embodiments, the first mutation is introduced into the cell by inserting a nucleic acid comprising a cassette which includes a promoter operably linked to a nucleic acid encoding a selectable marker and operably linked to one or more nucleic acids having substantial sequence identity to the endogenous gene to be mutated, whereby the cassette is integrated into one endogenous allele of the gene. In other preferred embodiments, the mutation is introduced in the cell by inserting into the cell a nucleic acid comprising a first cassette which includes a first promoter operably linked to a nucleic acid encoding a first selectable marker and operably linked to a first nucleic acid having substantial sequence identity to the endogenous gene to be mutated, whereby the first cassette is integrated into a first endogenous allele of the gene producing a first transgenic cell. Into the first transgenic cell is inserted a nucleic acid comprising a second cassette which includes a second promoter operably linked to a nucleic acid encoding a second selectable marker and operably linked to a second nucleic acid having substantial sequence identity to the gene. The second selectable marker differs from the first selectable marker, and the second cassette is integrated into a second endogenous allele of the gene producing a second transgenic cell. In still other preferred embodiments, a cell is isolated from the embryo, the fetus, or an offspring produced from the fetus, and another mutation is introduced into a gene of the cell. A second round of nuclear transfer is then performed using the resulting cell, a chromatin mass from the cell, or a nucleus from the cell to produce a transgenic ungulate with two or more mutations. The mutations are in the same or different alleles of a gene or are in different genes. In preferred embodiments, the cell that is mutated is a fibroblast (e.g., a fetal fibroblast). Preferably, the endogenous gene that is mutated is operably linked to an endogenous promoter that is not active in a fibroblast. In other preferred embodiments, the endogenous promoter operably linked to the endogenous gene that is mutated is less than 80, 70, 60, 50, 40, 30, 20, 10% as active as an endogenous promoter operably linked to a endogenous housekeeping gene such as GAPDH. Promoter activity may be measured using any standard assay, such as assays that measure the level of mRNA or protein encoded by the gene (see, for example, Ausubel et al. Current Protocols in Molecular Biology, volume 2, p. 11.13.1–11.13.3, John Wiley & Sons, 1995). This method for generating a transgenic ungulate has the advantage of allowing a gene that is not expressed in the donor cell (i.e., the cell that is the source of the genetic material used for nuclear transfer) to be mutated.

Accordingly, the invention as claimed features a transgenic ungulate having one or more nucleic acids encoding all or part of a xenogenous immunoglobulin (Ig) gene which undergoes rearrangement and expresses more than one xenogenous Ig molecule. In a preferred embodiment, the nucleic acid encoding all or part of a xenogenous Ig gene is substantially human. Preferably, the nucleic acid encodes an xenogenous antibody, such as a human antibody or a polyclonal antibody. In various embodiments, the Ig chain or antibody is expressed in serum and/or milk. In other embodiments, the nucleic acid is contained within a chromosome fragment, such as a ΔHAC or a ΔΔHAC. In yet other embodiments, the nucleic acid is maintained in an ungulate cell independently from the host chromosome.

In still other embodiments, the nucleic acid is integrated into a chromosome of the ungulate. In yet other embodiments, the nucleic acid includes unrearranged antibody light chain nucleic acid segments in which all of the nucleic acid segments encoding a V gene segment are separated from all of the nucleic acid segments encoding a J gene segment by one or more nucleotides. In yet other embodiments, the nucleic acid includes unrearranged antibody heavy chain nucleic acid segments in which either (i) all of the nucleic acid segments encoding a V gene segment are separated from all of the nucleic acid segments encoding a D gene segment by one or more nucleotides and/or (ii) all of the nucleic acid segments encoding a D gene segment are separated from all of the nucleic acid segments encoding a J gene segment by one or more nucleotides. In yet another preferred embodiment, the ungulate has a mutation in one or both alleles of an endogenous Ig gene, alpha-(1,3)-galactosyltransferase gene, prion gene, and/or J chain gene. In other preferred embodiments, the ungulate has a nucleic acid encoding an exogenous J chain, such as a human J chain. Preferably, the ungulate is a bovine, ovine, porcine, or caprine.

In another aspect, the invention features a transgenic ungulate having a mutation that reduces the expression of an endogenous antibody. Preferably, the mutation reduces the expression of functional IgM heavy chain or substantially eliminates the expression of functional IgM heavy chain. In other preferred embodiments, the mutation reduces the expression of functional Ig light chain or substantially eliminates the expression of functional Ig light chain. In yet other preferred embodiments, the mutation reduces the expression of functional IgM heavy chain and functional Ig light chain, or the mutation substantially eliminates the expression of functional IgM heavy chain and functional Ig light chain. Preferably, the ungulate also has a mutation in one or both alleles of an endogenous nucleic acid encoding alpha-(1,3)-galactosyltransferase, prion protein, and/or J chain. In other preferred embodiments, the ungulate has a nucleic acid encoding an exogenous J chain, such as a human J chain. In another preferred embodiment, the ungulate has one or more nucleic acids encoding all or part of a xenogenous Ig gene which undergoes rearrangement and expresses more than one xenogenous Ig molecule. Preferably, the nucleic acid encoding all or part of a xenogenous Ig gene is substantially human. In other preferred embodiments, the nucleic acid encodes a xenogenous antibody, such as a an antibody from another genus (e.g., a human antibody) or a polyclonal antibody. In various embodiments, the Ig chain or antibody is expressed in serum. In other embodiments, the nucleic acid is contained within a chromosome fragment, such as a ΔHAC or a ΔΔHAC. In yet other embodiments, the nucleic acid is maintained in an ungulate cell independently from the host chromosome. In still other embodiments, the nucleic acid is integrated into a chromosome of the ungulate. Preferably, the ungulate is a bovine, ovine, porcine, or caprine.

The invention also provides cells obtained from any of the ungulates of the invention or cells that are useful in the production of any of the ungulates of the invention.

Accordingly, in another aspect, the invention features an ungulate somatic cell having one or more nucleic acids encoding all or part of a xenogenous Ig gene that is capable of undergoing rearrangement and expressing one or more xenogenous Ig molecules in B cells. Preferably, the nucleic acid encoding all or part of a xenogenous Ig gene encodes a xenogenous antibody. In various embodiments, the nucleic acid is contained in a chromosome fragment, such as a ΔHAC or a ΔΔHAC. In yet other embodiments, the nucleic acid is maintained in an ungulate cell independently from the host chromosome. In still other embodiments, the nucleic acid is integrated into a chromosome of the cell. In another embodiment, the nucleic acid is substantially human. Preferably, the xenogenous antibody is an antibody from another genus, such as a human antibody. Preferably, the cell has a mutation in one or both alleles of an endogenous nucleic acid encoding alpha-(1,3)-galactosyltransferase, prion protein, and/or J chain. In other preferred embodiments, the cell has a nucleic acid encoding an exogenous J chain, such as a human J chain. Exemplary ungulate cells include fetal fibroblasts and B-cells. Preferably, the ungulate is a bovine, ovine, porcine, or caprine.

In another aspect, the invention features an ungulate somatic cell having a mutation in a nucleic acid encoding an Ig heavy and/or light chain. In preferred embodiments, the cell has a mutation in one or both alleles of the IgM heavy chain or the Ig light chain. Exemplary mutations include nonsense and deletion mutations. Preferably, the cell has a mutation in one or both alleles of an endogenous nucleic acid encoding alpha-(1,3)-galactosyltransferase, prion protein, and/or J chain. In other preferred embodiments, the cell has a nucleic acid encoding an exogenous J chain, such as a human J chain. In preferred embodiments, the cell also has one or more nucleic acids encoding all or part of a xenogenous Ig gene that is capable of undergoing rearrangement and expressing one or more xenogenous Ig molecules in B cells. Preferably, the nucleic acids encoding all or part of a xenogenous Ig gene is substantially human and/or encodes a xenogenous antibody, such as an antibody from another genus (e.g., a human antibody). In various embodiments, the nucleic acid is contained in a chromosome fragment, whereby the nucleic acid is maintained in the ungulate cell independently from the host chromosome. Preferred chromosome fragments include ΔHAC and ΔΔHAC. In yet other embodiments, the nucleic acid is maintained in an ungulate cell independently from the host chromosome. In still other embodiments, the nucleic acid is integrated into a chromosome of the cell. Exemplary ungulate cells include fetal fibroblasts and B-cells. Preferably, the ungulate is a bovine, ovine, porcine, or caprine.

In another aspect, the invention features a hybridoma formed from the fusion of an ungulate B-cell of the invention with a myeloma cell. Preferably, the hybridoma secretes an exogenous antibody, such as a human antibody.

The invention also provides methods for producing antibodies using an ungulate of the invention. One such method involves administering one or more antigens of interest to an ungulate having one or more nucleic acids encoding a xenogenous antibody gene locus. The nucleic acid segments in the gene locus undergo rearrangement resulting in the production of antibodies specific for the antigen, and the antibodies are recovered from the ungulate. In various embodiments, the nucleic acid encoding the xenogenous antibody gene locus is contained in a chromosome fragment, such as a ΔHAC or a ΔΔHAC. Preferably, the chromosome fragment is maintained in an ungulate cell independently from the host chromosome. In other embodiments, the nucleic acid is integrated into a chromosome of the ungulate. Preferably, the nucleic acid is substantially human. In other preferred embodiments, the light chain of the antibodies and/or the heavy chain of the antibodies is encoded by a human nucleic acid. The antibodies may be monoclonal or polyclonal. Monoclonal and polyclonal antibodies against particular antigen have a variety of uses; for example, they may be used as ingredients in prophylactic or therapeutic compositions for infection of pathogenic microorganisms such as bacteria or viruses. In various embodiments, the antibodies are recovered from the serum or milk of the ungulate. In preferred embodiments, the ungulate has a mutation that reduces the expression of an endogenous antibody, that reduces the expression of functional IgM heavy chain, or that reduces the expression of functional Ig light chain. Preferably, the ungulate has a mutation in one or both alleles of an endogenous nucleic acid encoding alpha-(1,3)-galactosyltransferase, prion protein, and/or J chain. In other preferred embodiments, the ungulate has a nucleic acid encoding an exogenous J chain, such as a human J chain. Preferably, the ungulate is a bovine, ovine, porcine, or caprine.

In a related aspect, the invention features another method of producing antibodies. This method involves recovering xenogenous antibodies from an ungulate having nucleic acid encoding a xenogenous antibody gene locus. The nucleic acid segments in the gene locus undergo rearrangement resulting in the production of xenogenous antibodies. In various embodiments, the nucleic acid encoding a xenogenous antibody gene locus is contained in a chromosome fragment, such as a ΔHAC or a ΔΔHAC. In particular embodiments, the nucleic acid is maintained in an ungulate cell independently from the host chromosome. In still other embodiments, the nucleic acid is integrated into a chromosome of the ungulate. Preferably, the nucleic acid is substantially human. In particular embodiments, the light chain of the antibodies and/or the heavy chain of the antibodies is encoded by a human nucleic acid. The antibodies may be monoclonal or polyclonal. In particular embodiments, polyclonal antibodies, such as IgG antibodies generated without immunization of the ungulate with a specific antigen, are used as a therapeutic substitute for IVIG (intraveneous immunoglobulin) produced from human serum. In various embodiments, the antibodies are recovered from the serum or milk of the ungulate. Preferably, the ungulate has a mutation that reduces the expression of an endogenous antibody, reduces the expression of functional IgM heavy chain, or reduces the expression of functional Ig light chain. Preferably, the ungulate has a mutation in one or both alleles of an endogenous nucleic acid encoding alpha-(1,3)-galactosyltransferase, prion protein, and/or J chain. In other preferred embodiments, the ungulate has a nucleic acid encoding an exogenous J chain, such as a human J chain. Preferably, the ungulate is a bovine, ovine, porcine, or caprine.

The invention also provides methods for producing transgenic ungulates. These methods may be used to produce transgenic ungulates having a desired mutation or having a desired xenogenous nucleic acid.

In one such aspect, the invention features a method of producing a transgenic ungulate that involves inserting a cell, a chromatin mass from a cell, or a nucleus from a cell into an oocyte. The cell includes a first mutation in an endogenous antibody heavy chain and/or light chain nucleic acid. The oocyte or an embryo formed from the oocyte is transferred into the uterus of a host ungulate under conditions that allow the oocyte or the embryo to develop into a fetus. Preferably, the fetus develops into a viable offspring. Preferably, the cell used in the production of the transgenic ungulate has a mutation in one or both alleles of an endogenous nucleic acid encoding alpha-(1,3)-galactosyltransferase, prion protein, and/or J chain. In other preferred embodiments, the cell has a nucleic acid encoding an exogenous J chain, such as a human J chain. In other embodiments, the cell includes one or more nucleic acids encoding all or part of a xenogenous Ig gene that is capable of undergoing rearrangement and expressing one or more xenogenous Ig molecules in B cells. Preferably, the nucleic acid encoding all or part of a xenogenous Ig gene encodes a xenogenous antibody. In yet other embodiments, the nucleic acid is integrated into a chromosome of the cell. Preferably, the xenogenous antibody is an antibody from another genus, such as a human antibody. In particular embodiments, the nucleic acid is contained in a chromosome fragment, such as a ΔHAC or a ΔΔHAC. In other particular embodiments, the chromosome fragment is maintained in an ungulate cell independently from the host chromosome. Preferably, the ungulate is a bovine, ovine, porcine, or caprine.

In various embodiments of the above aspect, the method also includes isolating a cell from the embryo, the fetus, or an offspring produced from the fetus and introducing a second mutation in an endogenous antibody heavy chain and/or light chain nucleic acid in the cell. The cell, a chromatin mass from the cell, or a nucleus from the cell is inserted into an oocyte, and the oocyte or an embryo formed from the oocyte is transferred into the uterus of a host ungulate under conditions that allow the oocyte or the embryo to develop into a fetus.

In other embodiments of the above aspect, the cell used for generation of the transgenic ungulate is prepared by a method that includes inserting into the cell a nucleic acid having a cassette which includes a promoter operably linked to a nucleic acid encoding a selectable marker and operably linked to one or more nucleic acids having substantial sequence identity to the antibody heavy chain or light chain nucleic acid. The cassette is integrated into one endogenous allele of the antibody heavy chain or light chain nucleic acid.

In other embodiments, the cell is produced by inserting into the cell a nucleic acid having a first cassette which includes a first promoter operably linked to a nucleic acid encoding a first selectable marker and operably linked to a first nucleic acid having substantial sequence identity to the antibody heavy chain or light chain nucleic acid. The first cassette is integrated into a first endogenous allele of the antibody heavy chain or light chain nucleic acid producing a first transgenic cell.

Into the first transgenic cell is inserted a nucleic acid having a second cassette which includes a second promoter operably linked to a nucleic acid encoding a second selectable marker and operably linked to a second nucleic acid having substantial sequence identity to the antibody heavy chain or light chain nucleic acid. The second selectable marker differs from the first selectable marker. The second cassette is integrated into a second endogenous allele of the antibody heavy chain or light chain nucleic acid producing a second transgenic cell.

In yet another aspect, the invention features another method of producing a transgenic ungulate. This method involves inserting a cell having one or more xenogenous nucleic acids into an oocyte. The xenogenous nucleic acid encodes all or part of a xenogenous Ig gene, and the gene is capable of undergoing rearrangement and expressing more than one xenogenous Ig molecule in B cells. The oocyte or an embryo formed from the oocyte is transferred into the uterus of a host ungulate under conditions that allow the oocyte or the embryo to develop into a fetus. Preferably, the fetus develops into a viable offspring. Preferably, the nucleic acid encoding all or part of a xenogenous Ig gene encodes a xenogenous antibody. In other preferred embodiments, the antibody is a polyclonal antibody. In yet other preferred embodiments, the immunogloblulin chain or antibody is expressed in serum and/or milk. In various embodiments, the nucleic acid is contained in a chromosome fragment, such as a ΔHAC or a ΔΔHAC. The nucleic acid can be maintained in an ungulate cell independently from the host chromosome or integrated into a chromosome of the cell. Preferably, the nucleic acid is substantially human. In other embodiments, the xenogenous antibody is an antibody from another genus, such as a human antibody. Preferably, the ungulate is a bovine, ovine, porcine, or caprine.

In yet another related aspect, the invention features another method of producing a transgenic ungulate. This method involves inserting a cell, a chromatin mass from a cell, or a nucleus from a cell into an oocyte. The cell includes a first mutation in an endogenous gene that is not naturally expressed by the cell. The oocyte or an embryo formed from the oocyte is transferred into the uterus of a host ungulate under conditions that allow the oocyte or the embryo to develop into a fetus. Preferably, the fetus develops into a viable offspring. Preferably, the gene that is mutated encodes an antibody, alpha-(1,3)-galactosyltransferase, prion protein, or J chain. In another preferred embodiment, the cell used in the production of the transgenic ungulate is a fibroblast, such as a fetal fibroblast.

In various embodiments of the above method, the cell is prepared by inserting into the cell a nucleic acid having a cassette which includes a promoter operably linked to a nucleic acid encoding a selectable marker and operably linked to one or more nucleic acids having substantial sequence identity to the gene; whereby the cassette is integrated into one endogenous allele of the gene. In other embodiments, the cell is produced by inserting into the cell a nucleic acid having a first cassette which includes a first promoter operably linked to a nucleic acid encoding a first selectable marker and operably linked to a first nucleic acid having substantial sequence identity to the gene. The first cassette is integrated into a first endogenous allele of the gene producing a first transgenic cell. Into the first transgenic cell is inserted a nucleic acid having a second cassette which includes a second promoter operably linked to a nucleic acid encoding a second selectable marker and operably linked to a second nucleic acid having substantial sequence identity to the gene. The second selectable marker differs from the first selectable marker. The second cassette is integrated into a second endogenous allele of the gene producing a second transgenic cell.

In other embodiments of the above aspect, the method also includes introducing a second mutation into the transgenic ungulate. In these embodiments, a cell is isolated from the embryo, the fetus, or an offspring produced from the fetus, and a second mutation is introduced in an endogenous gene in the cell. The cell, a chromatin mass from the cell, or a nucleus from the cell is inserted into an oocyte, and the oocyte or an embryo formed from the oocyte is transferred into the uterus of a host ungulate under conditions that allow the oocyte or the embryo to develop into a fetus.

The ungulates of the invention can be used to produce antiserum or milk containing an antibody of interest. In one such aspect, the invention features ungulate antiserum having polyclonal human immunoglobulins. Preferably, the antiserum is from a bovine, ovine, porcine, or caprine. In another preferred embodiment, the Igs are directed against a desired antigen.

In yet another aspect, the invention features ungulate milk having polyclonal human Igs. Preferably, the milk is from a bovine, ovine, porcine, or caprine. In another preferred embodiment, the Igs are directed against a desired antigen.

In preferred embodiments of various aspects of the invention, the heavy chain is a mu heavy chain, and the light chain is a lambda or kappa light chain. In other preferred embodiments, the nucleic acid encoding the xenogenous immunoglobulin chain or antibody is in its unrearranged form. Preferably, an antigen of interest is administered to a transgenic ungulate having the xenogenous immunoglobulin gene locus and antibodies reactive with the antigen of interest are produced. In other preferred embodiments, more than one class of xenogenous antibody is produced by the ungulate. In various embodiments, more than one different xenogenous Ig or antibody is produced by the ungulate. Preferred nuclear transfer methods include inserting a cell of the invention, a chromatin mass from the cell, or a nucleus from the cell into an enucleated or nucleated oocyte, and transferring the oocyte or an embryo formed from the oocyte into the uterus of a host ungulate under conditions that allow the oocyte or the embryo to develop into a fetus.

In other preferred embodiments of various aspects of the invention, the ungulate has a mutation in one or both alleles of the endogenous alpha-(1,3)-galactosyltransferase, prion, and/or J chain nucleic acid. Preferably, the mutation reduces or eliminates the expression of the endogenous alpha-(1,3)-galactosyltransferase enzyme, galactosyl($\alpha$1,3)galactose epitope, prion protein, and/or J chain. In still other preferred embodiments, the ungulate contains a xenogenous J chain nucleic acid, such as a human J chain nucleic acid. Preferably, the ungulate produces human IgA or IgM molecules containing human J chain. In various embodiments of the invention, the nucleic acid used to mutate an endogenous ungulate nucleic acid (e.g., a knockout cassette which includes a promoter operably linked to a nucleic acid encoding a selectable marker and operably linked to a nucleic acid having substantial sequence identity to the gene to be mutated) is not contained in a viral vector, such as an adenoviral vector or an adeno-associated viral vector. For example, the nucleic acid may be contained in a plasmid or artificial chromosome that is inserted into an ungulate cell, using a standard method such as transfection or lipofection that does not involve viral infection of the cell. In yet another embodiment, the nucleic acid used to mutate an endogenous ungulate nucleic acid (e.g., a knockout cassette which includes a promoter operably linked to a nucleic acid encoding a selectable marker and operably linked to a nucleic acid having substantial sequence identity to the gene to be mutated) is contained in a viral vector, such as an adenoviral vector or an adeno-associated viral vector. According to this embodiment, a virus containing the viral vector is used to infect an ungulate cell, resulting in the insertion of a portion or the entire viral vector into the ungulate cell.

Exemplary ungulates include members of the orders Perissodactyla and Artiodactyla, such as any member of the genus Bos. Other preferred ungulates include sheep, bighorn sheep, goats, buffalos, antelopes, oxen, horses, donkeys, mule, deer, elk, caribou, water buffalo, camels, llama, alpaca, pigs, and elephants. Preferably, the transgenic ungulate expresses an immunoglobulin chain or antibody from another genus, such as an antibody from any other mammal.

As used herein, by "a nucleic acid in its pre-arranged or unrearranged form" is meant a nucleic acid that has not undergone V(D)J recombination. In preferred embodiments, all of the nucleic acid segments encoding a V gene segment of an antibody light chain are separated from all of the nucleic acid segments encoding a J gene segment by one or more nucleotides. Preferably, all of the nucleic acid segments encoding a V gene segment of an antibody heavy chain are separated from all of the nucleic acid segments encoding a D gene segment by one or more nucleotides, and/or all of the nucleic acid segments encoding a D gene segment of an antibody heavy chain are separated from all of the nucleic acid segments encoding a J gene segment by one or more nucleotides. Preferably, a nucleic acid in its unrearranged form is substantially human. In other preferred embodiments, the nucleic acid is at least 70, 80, 90, 95, or 99% identical to the corresponding region of a naturally-occurring nucleic acid from a human.

BRIEF DESCRIPTION OF THE FIGURES

In FIGS. 1A and 1B, "Homo" denotes homozygous; "Hemi" denotes hemizygous; "H" denotes heavy chain; "L" denotes light chain; "HAC" denotes human artificial chromosome; "HAC 1" denotes either HAC; and "HAC2" denotes a second HAC.

FIG. 6 is a picture of an agarose gel showing the expression of human Cmu exons 3 and 4 in a ΔHAC fetus at 77 gestational days (fetus #5996).

FIG. 8 is a picture of an agarose gel showing the expression of rearranged human heavy chain in ΔHAC fetus #5996.

FIG. 11A is the polynucleotide sequence of a rearranged human heavy chain transcript from ΔHAC fetus #5996 (SEQ ID NO: 49). FIG. 11B is a sequence alignment of a region of this sequence ("Query") with a human anti-pneumococcal antibody ("Sbjct") (SEQ ID NOs: 50 and 51, respectively). For the query sequence from ΔHAC fetus #5996, only those nucleotides that differ from the corresponding nucleotides of the human anti-pneumococcal antibody sequence are shown.

FIGS. 12A and 12B are two additional polynucleotide sequences (SEQ ID NOs: 52 and 54) and their deduced amino acid sequences (SEQ ID NOs: 53 and 55, respectively) of rearranged human heavy chain transcripts from ΔHAC fetus #5996.

FIG. 20 is a polynucleotide sequence and the corresponded deduced amino acid sequence of a rearranged human light chain transcript from ΔΔHAC fetus #5442A (SEQ ID NOs: 56 and 57, respectively).

FIG. 21 is another polynucleotide sequence and the corresponding deduced amino acid sequence of a rearranged human light chain transcript from ΔΔHAC fetus #5442A (SEQ ID NOs: 58 and 59, respectively).

FIGS. 22A–22H are graphs of a FACS analysis of expression of human lambda light chain and bovine heavy chain proteins by ΔΔHAC fetuses #5442A (FIGS. 22A–22D) and 5442B (FIGS. 22E–22H). Lymphocytes from the spleens of these fetuses were reacted with a phycoerytherin labeled anti-human lambda antibody (FIGS. 22C and 22D), a FITC labeled anti-bovine IgM antibody (FIGS. 22D and 22H), or no antibody (FIGS. 22A, 22B, (22E, and 22F) and then analyzed on a FASCalibur cell sorter. The percent of cells that were labeled with one of the antibodies is displayed beneath each histogram.

FIG. 27 is table listing pregnancy rates for HAC carrying embryos.

DETAILED DESCRIPTION OF THE INVENTION

Figure 1A:
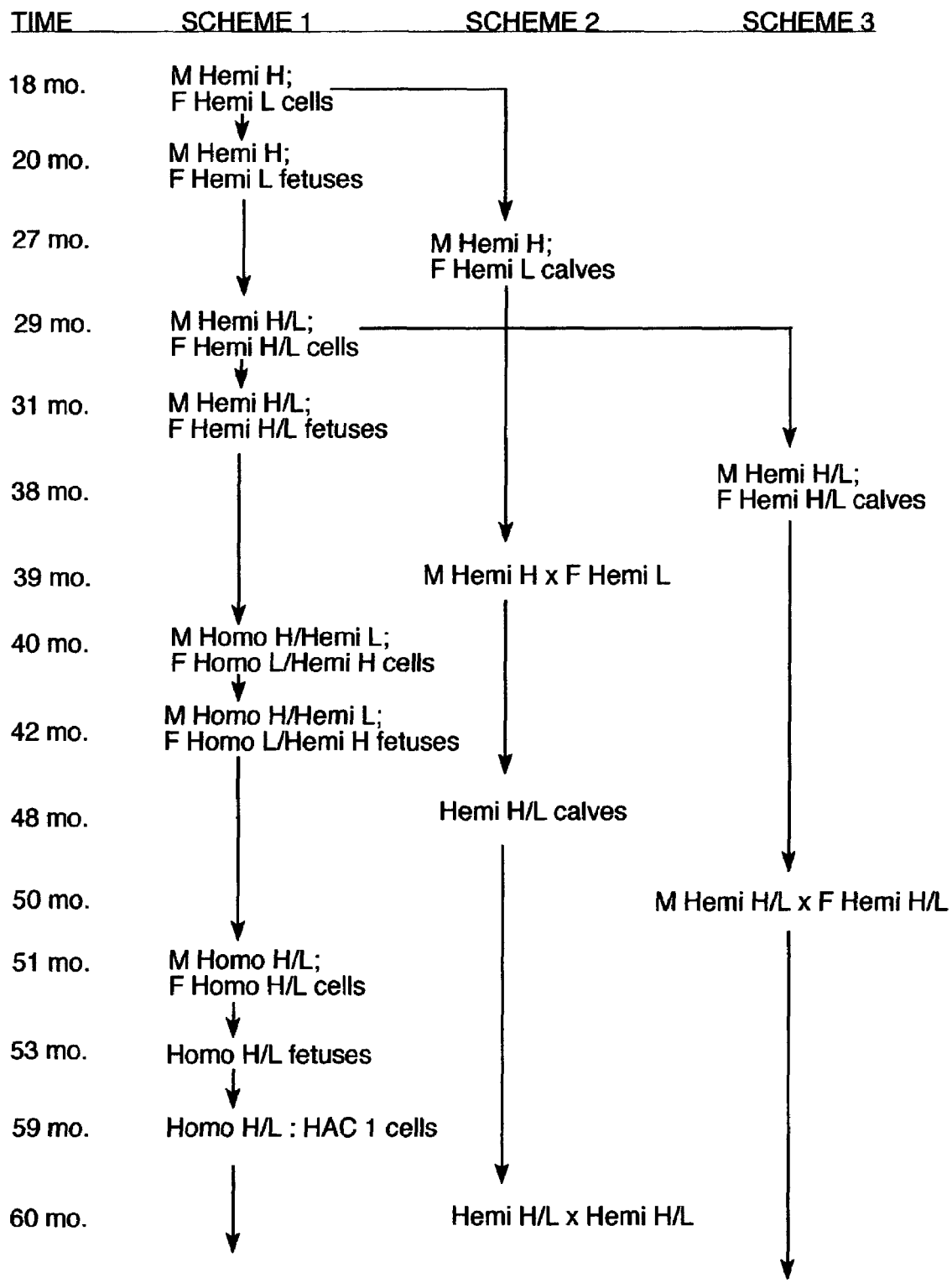
FIG. 1A contains an overview of the procedures used to produce a cow that contains an Ig knockout and human artificial chromosome. The time line in FIG. 1A is based on an estimated 18 months to prepare the Ig knockout vector and generate knockout cells, 2 months to generate fetuses from the knockout cells, 9 months to perform subsequent knockouts, 9 months of gestation for calves to be born, 12 months before embryos can be produced from calves, and 6 months to perform the HAC transfers.
Figure 1A:
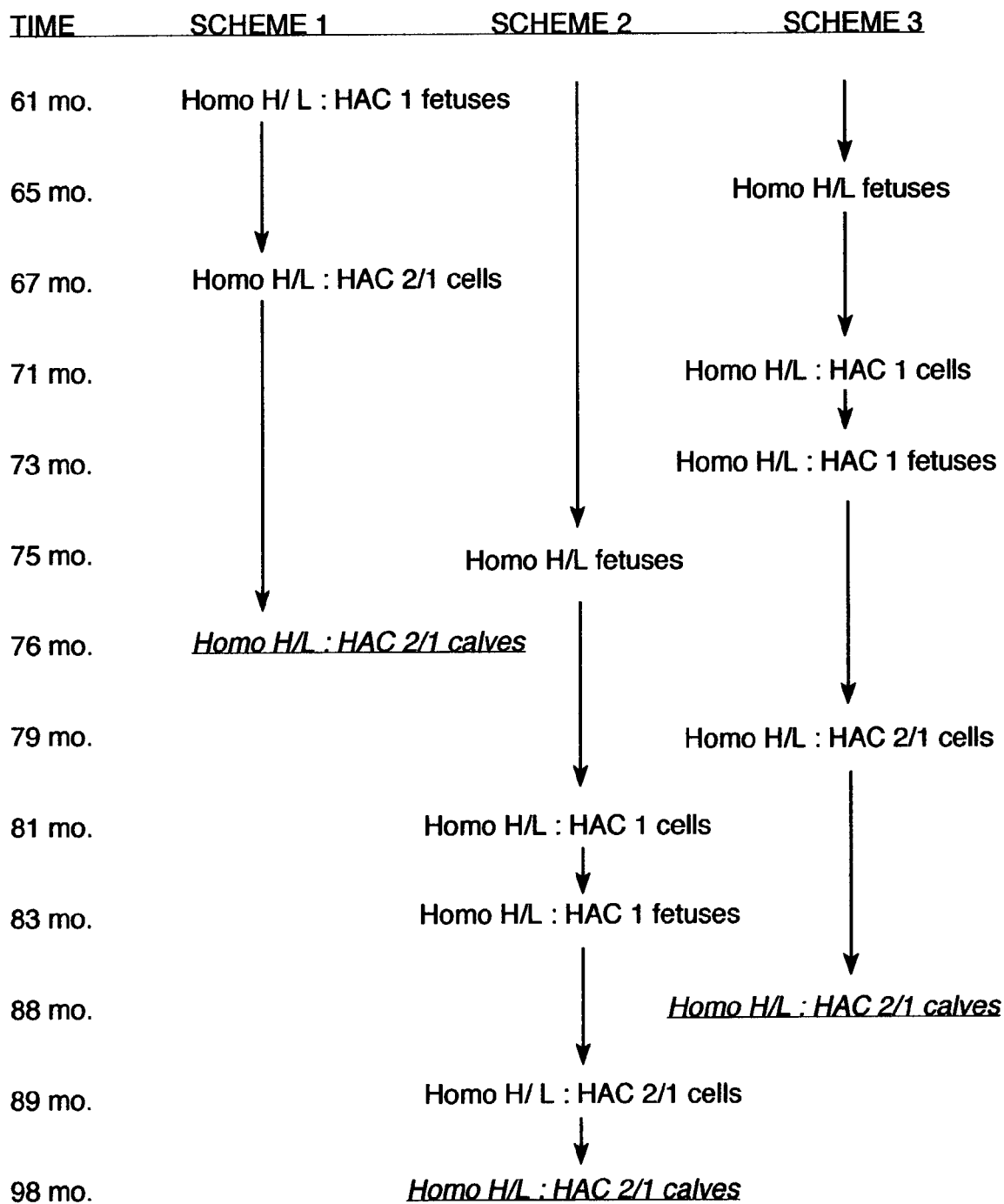
Figure 1B:
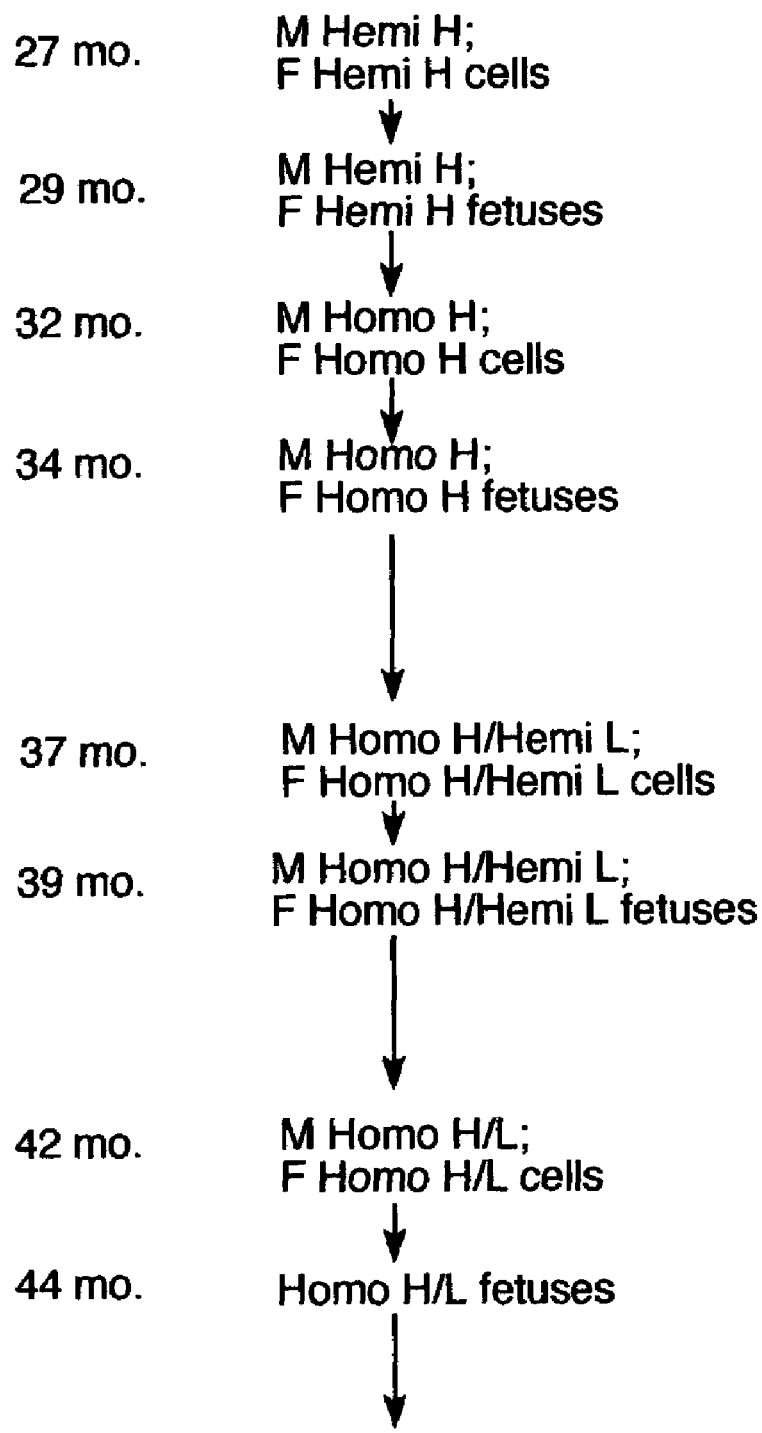
FIG. 1B contains an overview of the methods used to produce a cow that contains a mutation in an endogenous Ig gene and contains ΔHAC or ΔΔHAC. For the time line in FIG. 1B, it is estimated that 250 colonies are screened per week for a total of 3,000 colonies in 3 months to isolate male and female knockout cells. It is assumed that one or more knockout colonies are produced per 1,500 colonies. Homozygous knockout ungulates may be produced by (1) introducing a second Ig mutation in an isolated knockout cell before nuclear transfer, (2) introducing a second Ig mutation in a cell obtained from a embryo, fetus (e.g., fetus at ~60 gestation days), or offspring produced from a first round of nuclear transfer and using the resulting homozygous cell as the donor cell in a second round of nuclear transfer, or (3) mating hemizygous ungulates.
Figure 1B:
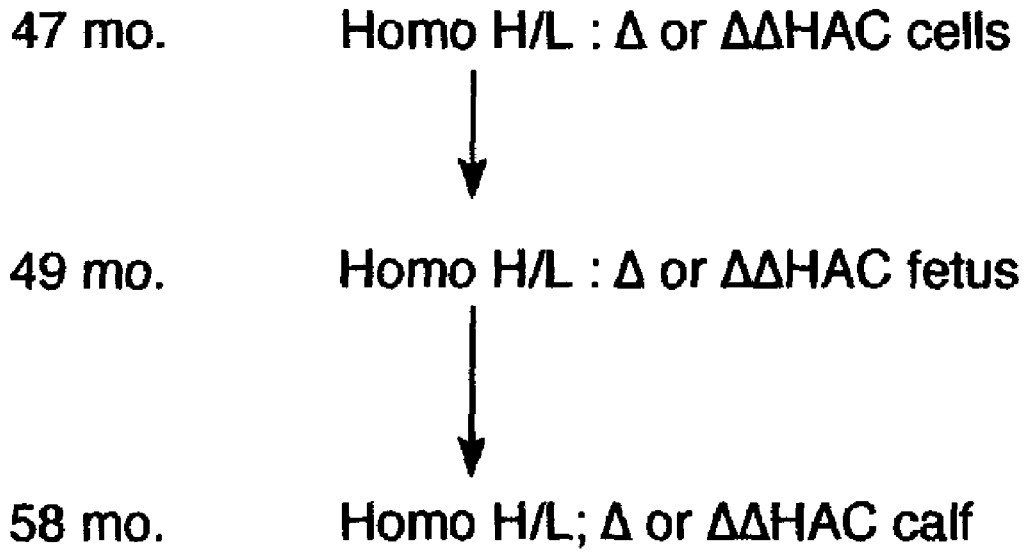

As discussed above, the present invention relates to the production of a transgenic ungulate, preferably a transgenic cow, wherein endogenous Ig expression has optionally been knocked out and a nucleic acid (preferably, an artificial chromosome) has been stably introduced that comprises genes which are necessary for the production of functional antibodies of another species, preferably human. Thereby, a transgenic animal may be obtained that does not produce its endogenous antibodies, but which instead produces antibodies of another species. Any non-endogenous antibodies may be produced including, without limitation, human, non-human primate, dog, cat, mouse, rat, or guinea pig antibodies. While the production of human monoclonal antibodies in goats has been previously reported, this has not been effected in cows, in serum or in any ungulate that do not express its endogenous antibodies. Furthermore, the insertion of germline (unrearragned) heavy or light chain genes, the rearrangement of these genes and the expression of diversified antibody have not been performed in a transgenic ungulate. It is unpredictable whether such ungulates would survive because it is uncertain whether human Igs will be functionally expressed, or expressed in sufficient amounts to provide for adequate immune responses. Also, it is uncertain whether human chromosomes will be stably maintained in transgenic ungulates. Still further, it is uncertain whether that ungulate (for example, bovine) B cells will be able to express or properly rearrange human or other non-endogenous Igs.

In a preferred embodiment of the present approach, xenogenous immunoglobulin production is accomplished essentially by the combined use of nuclear transfer, homologous recombination techniques, and the introduction of artificial chromosomes carrying entire xenogenous Ig loci. More specifically, the process preferably involves the targeted disruption of one or both alleles of the IgM heavy chain gene, and optionally one or both alleles of the Ig light chain gene, although xenogenous antibody production can also be accomplished in wild-type animals (i.e., animals without Ig knock outs). Gene knock outs may be effected by sequential homologous recombination, then another mating procedure. In a preferred embodiment, this is effected by initially effecting targeted disruption of one allele of the IgM heavy chain gene of a male or female ungulate (for example, bovine) fetal fibroblast in tissue culture using a suitable homologous recombination vector. The use of fetal fibroblasts is preferred over some other somatic cells as these cells are readily propagated and genetically manipulated in tissue culture. However, the use of fetal fibroblasts is not essential to the invention, and indeed other cell lines may be substituted therefor with equivalent results.

This process, of course, entails constructing a DNA construct having regions of homology to the targeted IgM heavy chain allele such that the construct upon integration into an IgM heavy chain allele in the ungulate genome disrupts the expression thereof. An exemplary vector for carrying out such targeted disruption of an IgM allele is described in the example which follows. In this regard, methods for constructing vectors that provide for homologous recombination at a targeted site are well known to those skilled in the art. Moreover, in the present instance, the construction of a suitable vector is within the level of skill in the art, given especially that the sequence of the bovine IgM heavy chain and Ig lambda light chain genes are known, as are the sequences of immunoglobulon genes from other ungulates (see below) In order to facilitate homologous recombination, the vectors used to effect homologous recombination and inactivation of the IgM gene, respectively, comprise portions of DNA that exhibit substantial sequence identity to the ungulate IgM heavy and Ig light chain genes. Preferably, these sequences possessing at least 98% sequence identity, more preferably, at least 99% sequence identity, and still more preferably will be isogenic with the targeted gene loci to facilitate homologous recombination and targeted deletion or inactivation.

Figure 2A:
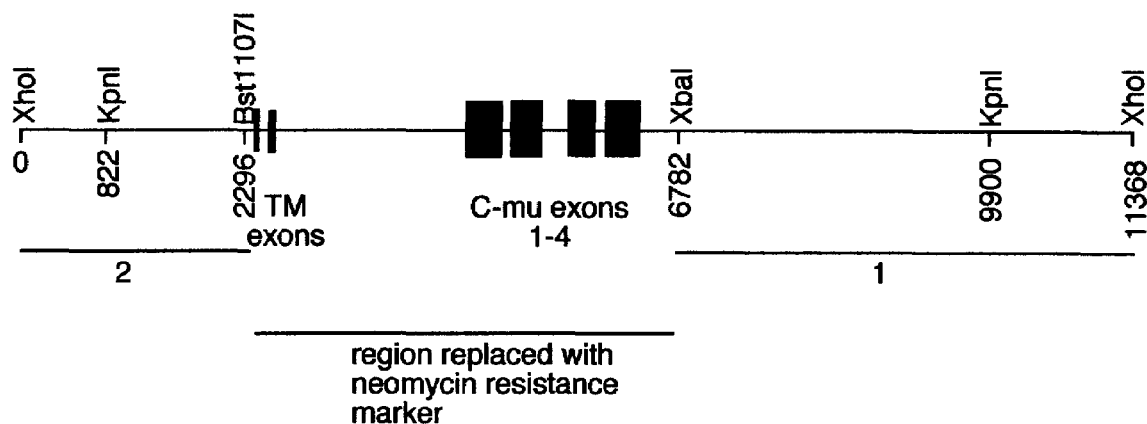
FIG. 2A contains a mu (IgM heavy chain) knockout construct according to the invention.

Typically, and preferably the construct will comprise a marker gene that provides for selection of desired homologous recombinants, for example, fibroblast cells, wherein the IgM heavy chain gene and/or Ig light chain gene has been effectively disrupted. Exemplary marker genes include antibiotic resistance markers, drug resistance markers, and green fluorescent protein, among others. A preferred construct is shown in FIG. 2A and starting materials used to make this construct in FIGS. 3A and 3B. Other constructs containing two regions of homology to an endogenous immunoglobulin gene, which flank a positive selection marker (e.g., an antibiotic resistance gene) that is operably linked to a promoter, may be generated using standard molecular biology techniques and used in the methods of the present invention.

Figure 3A:
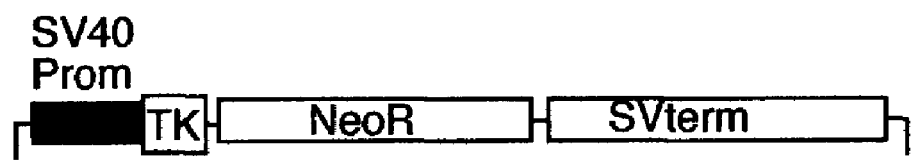
FIGS. 3A and 3B contain schematic illustrations of construct "pSTneoB" and "pLoxP-STneoB" that were used to produce the mu knockout DNA construct, which is illustrated in FIG. 3C.
Figure 3B:
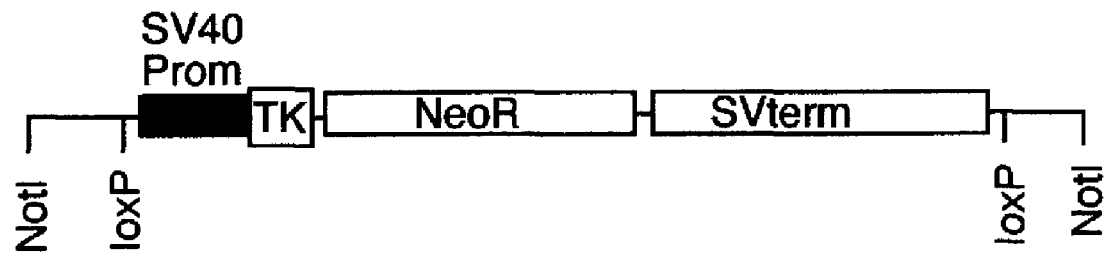
Figure 3C:
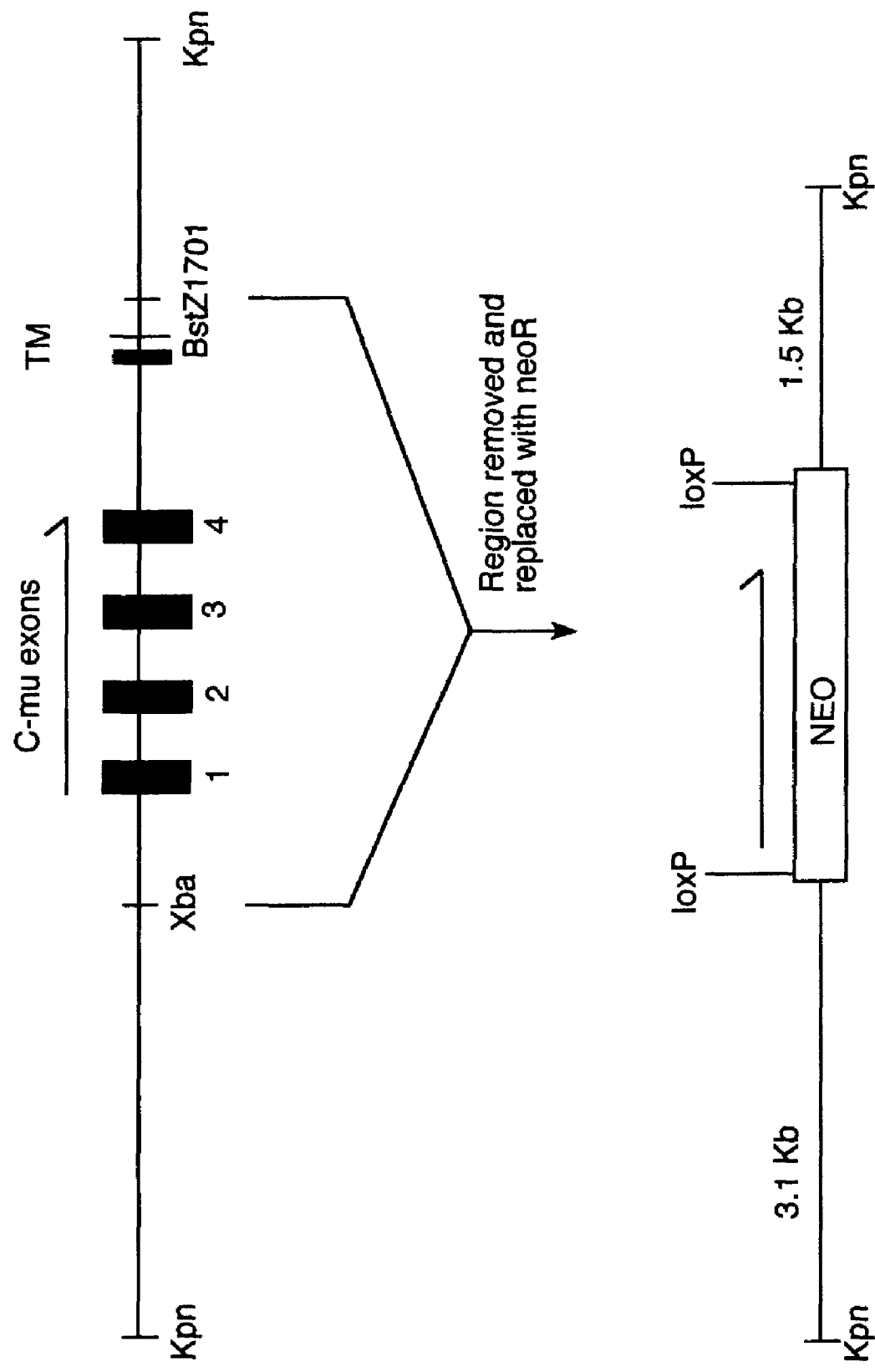
FIG. 3D is the polynucleotide sequence of the 1.5 kb region of the genomic bovine mu heavy chain locus that was used as the first region of homology in the mu knockout construct (SEQ ID NO: 47).
FIG. 3E is the polynucleotide sequence of the 3.1 kb region of the genomic bovine mu heavy chain locus that was used as the second region of homology in the mu knockout construct construct (SEQ ID NO: 48). In this sequence, each "n" represents any nucleotide or no nucleotide. The region of consecutive "n" nucleotides represents an approximately 0.9 to 1.0 kb region for which the polynucloetide sequence has not been determined.
FIG. 3F is a schematic illustration of a puromycin resistant, bovine mu heavy chain knockout construct.
FIG. 3G is the polynucleotide sequence of a bovine kappa light chain cDNA (SEQ ID NO: 60). All or part of this sequence may be used in a kappa light chain knockout construct. Additionally, this kappa light chain may be used to isolate a genomic kappa light chain sequence for use in a kappa light chain knockout construct.

The mu knockout construct shown in FIGS. 2A and 3C was designed to remove the exons encoding the bovine immunoglobulin heavy chain constant region, designated as "C-mu exons 1–4" and the two exons encoding the transmembrane domain, designated "TM exons".

To construct this vector, the region designated as "1", an Xba1-Xho1 fragment from the genomic mu heavy chain bovine sequence, was subcloned into the commercial DNA vector, pBluescript (Stratagene, La Jolla, Calif.), previously cut with the enzymes XbaI and XhoI. Once this fragment was cloned, there was a NotI restriction enzyme recognition sequence adjacent to the XbaI site, used to insert a NotI fragment of approximately 3.5 Kb. This fragment contains a neomycin resistance marker, described further below. If desired, other mu knock out constructs may be constructed using the genomic mu heavy chain sequence from another ungulate breed, species, or genus (e.g., the mu heavy chain sequence deposited as Genbank accession number U63637 from a Swiss Bull/Holstein cross).

Once fragment "1" and the neomycin resistance marker were joined together into pBluescript, there remained a Sac1 site adjacent to the neomycin resistance marker. The new construct was linearized with Sac1 and converted to a blunt end by filling in the sticky ends left from the Sac1 digest, using DNA polymerase.

The fragment designated "2" was isolated as an XhoI-BstI1071 fragment and converted to a blunt-ended fragment by filling in the sticky ends left from the Xho1 and BstI1071 enzymes, using DNA polymerase.

Once finished, the final construct contained region 2, the neomycin resistance marker and region 1, respectively.

For transfection of bovine fibroblasts, the construct was digested with the restriction enzyme, Kpn1 (two Kpn1 sites are shown in the diagram) and the DNA fragment was used for homologous recombination.

The neomycin resistance construct was assembled as follows. A construct designated "pSTneoB" (Katoh et al., Cell Struct. Funct. 12:575, 1987; Japanese Collection of Research Biologicals (JCRB) deposit number: VE039) was designed to contain a neomycin resistance gene under the control of an SV40 promoter and TK enhancer upstream of the coding region. Downstream of the coding region is an SV40 terminator sequence. The neo cassette was excised from "pSTneoB" as a XhoI fragment. After the ends of the fragment were converted to blunt ends using standard molecular biology techniques, the blunt ended fragment was cloned into the EcoRV site in the vector, pBS246 (Gibco/Life Technologies). This site is flanked by loxP sites. The new construct, designated "pLoxP-STNeoR", was used to generate the mu knockout DNA construct. The desired fragment of this construct is flanked by loxP sites and NotI sites, which were originally present in the pBS246 cloning vector. The desired NotI fragment, which contains loxP-neo-loxP, was used for replacement of the immunoglobulin mu constant region exons. The SV40 promoter operably linked to the neomycin resistance gene activates the transcription of the neomycin resistance gene, allowing cells in which the desired NotI fragment has replaced the mu constant region exons to be selected based on their resulting antibiotic resistance.

After a cell line is obtained in which the IgM heavy chain allele has been effectively disrupted, it is used as a nuclear transfer donor to produce a cloned ungulate fetus (for example, a cloned bovine fetus) and eventually a fetus or animal wherein one of the IgM heavy alleles is disrupted. Thereafter, a second round of gene targeted disruption can be effected using somatic cells derived therefrom, e.g., fibroblasts, in order to produce cells in which the second IgM heavy chain allele is inactivated, using a similar vector, but containing a different selectable marker.

Preferably, concurrent to the first targeted gene disruption, a second ungulate (for example, bovine) somatic cell line is also genetically modified, which similarly may be of male or female origin. If the first cell line manipulated is male, it is preferable to modify a female cell line; vice versa if the first cell line manipulated is female, it is preferable to select a male cell line. Again, preferably, the manipulated cells comprise ungulate (for example, bovine) fetal fibroblasts.

In a preferred embodiment, the female fetal fibroblast is genetically modified so as to introduce a targeted disruption of one allele of the Ig lambda light chain gene. This method similarly is carried out using a vector having regions of homology to the ungulate (for example, bovine) Ig lambda light chain, and a selectable marker, which DNA construct is designed such that upon integration and homologous recombination with the endogenous Ig light chain results in disruption (inactivation) of the targeted Ig lambda light gene.

Once a female fibroblast cell line is selected having the desired targeted disruption, it similarly is utilized as a donor cell for nuclear transfer or the DNA from such cell line is used as a donor for nuclear transfer.

Alternatively, this cell may be subjected to a second round of homologous recombination to inactivate the second Ig lambda light chain using a similar DNA construct to that used to disrupt the first allele, but containing a different selectable marker.

As discussed in the background of the invention, methods for effecting nuclear transfer, and particularly for the production of cloned bovines and cloned transgenic bovines have been reported and are described in U.S. Pat. No. 5,995,577 issued to Stice et al. and assigned to University of Massachusetts. Still, alternatively the nuclear transfer techniques disclosed in WO 95/16670; WO 96/07732; WO 97/0669; or WO 97/0668, (collectively, Roslin Methods) may be used. The Roslin methods differ from the University of Massachusetts techniques in that they use quiescent rather than proliferating donor cells. All of these patents are incorporated by reference herein in their entirety. These nuclear transfer procedures will produce a transgenic cloned fetus which can be used to produce a cloned transgenic bovine offspring, for example, an offspring which comprises a targeted disruption of at least one allele of the Ig light chain gene and/or IgM gene. After such cell lines have been created, they can be utilized to produce a male and female heavy and light chain hemizygous knockout (M and F Hemi H/L) fetus and offspring. Moreover, these techniques are not limited to use for the production of transgenic bovines; the above techniques may be used for nuclear transfer of other ungulates as well.

Following nuclear transfer, production of desired animals may be affected either by mating the ungulates or by secondary gene targeting using the homologous targeting vector previously described.

As noted previously, a further object of the invention involves creating male and female heavy and light chain hemizygous knockouts wherein such hemizygous knockouts are produced using the cell lines already described. This may be affected either by mating of the offspring produced according to the above described methods, wherein an offspring which comprises a disrupted allele of the IgM heavy chain gene is mated with another offspring which comprises a disrupted allele of the Ig light chain. Alternatively, this may be affected by secondary gene targeting by manipulating a cell which is obtained from an offspring produced according to the above-described procedures. This will comprise effecting by homologous recombination targeted disruption of an allele of the IgM heavy chain gene or allele of the Ig light chain. After a cell line is produced which comprises a male and female heavy and light chain hemizygous knockout (M and F Hemi H/L) it will be used to produce a fetus or calf which comprises such a knockout. As noted, this is effected either by mating or secondary gene targeting.

Once the male and female heavy and light chain hemizygous knockouts are obtained, cells from these animals may be utilized to create homozygous knockout (Homo H/L) fetuses. Again, this is affected either by sequential gene targeting or mating. Essentially, if affected by mating, this will involve mating the male heavy and light chain hemizygous knockout with a female heavy and light chain hemizygous knockout and selection of an offspring which comprises a homozygous knockout. Alternatively, the cells from the hemizygous knockout described above may be manipulated in tissue culture, so as to knock out the other allele of the IgM or Ig light chain (lambda) gene. Secondary gene targeting may be preferred to mating as this may provide for more rapid results, especially given that the gestation period of ungulates, such as bovines, is relatively long.

Once homozygous knockouts (Homo H/L) have been obtained, they are utilized for introduction of a desired nucleic acid which contains genes (preferably, entire gene loci) for producing antibodies of a particular species, such as a human. Preferably, human artificial chromosomes are used, such as those disclosed in WO 97/07671 (EP 0843961) and WO00/10383 (EP 1106061). These human artificial chromosomes also are described in a corresponding issued Japanese patent JP 30300092. Both of these applications are incorporated by reference in their entirety herein. Also, the construction of artificial human chromosomes that contain and express human immunoglobulin genes is disclosed in Shen et al., *Hum. Mol. Genet.* 6(8):1375–1382 (1997); Kuroiwa et al., *Nature Biotechnol.* 18(10):1086–1090 (2000); and Loupert et al., *Chromosome* 107(4):255–259 (1998), all of which are incorporated by reference in their entirety herein. Human artificial chromosomes may also be utilized to introduce xenogenous antibody genes into wild-type animal cells; this is accomplished using the methods described above. Introduction of artificial chromosome into animal cells, especially fetal fibroblast cells can be performed by microcell fusion as described herein.

In an alternative to the use of human artificial chromosome, nucleic acid encoding immunoglobulin genes may be integrated into the chromosome using a YAC vector, BAC vector, or cosmid vector. Vectors comprising xenogenous Ig genes (WO98/24893, WO96/33735, WO 97/13852, WO98/24884) can be introduced to fetal fibroblasts cells using known methods, such as electroporation, lipofection, fusion with a yeast spheroplast comprising a YAC vector, and the like. Further, vectors comprising xenogenous Ig genes can be targeted to the endogenous Ig gene loci of the fetal fibroblast cells, resulting in the simultaneous introduction of the xenogenous Ig gene and the disruption of the endogenous Ig gene.

Integration of a nucleic acid encoding a xenogenous immunoglobulin gene may also be carried out as described in the patents by Lonberg et al. (supra). In the "knockin" construct used for the insertion of xenogenous immunoglobulin genes into a chromosome of a host ungulate, one or more immunoglobulin genes and an antibiotic resistance gene may be operably-linked to a promoter which is active in the cell type transfected with the construct. For example, a constitutively active, inducible, or tissue specific promoter may be used to activate transcription of the integrated antibiotic resistance gene, allowing transfected cells to be selected based on their resulting antibiotic resistance. Alternatively, a knockin construct in which the knockin cassette containing the Ig gene(s) and the antibiotic resistance gene is not operably-linked to a promoter may be used. In this case, cells in which the knockin cassette integrates downstream of an endogenous promoter may be selected based on the resulting expression of the antibiotic resistance marker under the control of the endogenous promoter. These selected cells may be used in the nuclear transfer procedures described herein to generate a transgenic ungulate containing a xenogenous immunoglobulin gene integrated into a host chromosome.

Using similar methodologies, it is possible to produce and insert artificial chromosomes containing genes for expression of Ig of different species such as dog, cat, other ungulates, non-human primates among other species. As discussed above, and as known in the art, immunoglobulin genes of different species are well known to exhibit substantial sequence homology across different species.

Once it has been determined that the inserted artificial chromosome, for example, a human artificial chromosome, has been stably introduced into a cell line, e.g., a bovine fetal fibroblast, it is utilized as a donor for nuclear transfer. This may be determined by PCR methods. Similarly, animals are obtained which comprise the homozygous knockout, and further comprise a stably introduced nucleic acid, such as a human artificial chromosome. After calves have been obtained which include the stably incorporated nucleic acid (for example, human artificial chromosome), the animals are tested to determine whether they express human Ig genes in response to immunization and affinity maturation.

Modifications of the overall procedure described above may also be performed. For example, xenogenous Ig genes may be introduced first and than endogenous Ig genes may be inactivated. Further, an animal retaining xenogenous Ig genes may be mated with an animal in which an endogenous Ig gene is inactivated. While the approaches to be utilized in the invention have been described above, the techniques that are utilized are described in greater detail below. These examples are provided to illustrate the invention, and should not be construed as limiting. In particular, while these examples focus on transgenic bovines, the methods described may be used to produce and test any transgenic ungulate.

Knockout Procedures to Produce Transgenic Ungulates that Express Human Igs

As discussed above, the present invention relates to the production of Homo H/L fetuses or calves. The approach is summarized in FIG. 1. There are three schemes outlined therein. The first relies on successive knockouts in regenerated fetal cell lines. This approach is the technically most difficult and has the highest level of risk but as noted above potentially yields faster results than breeding approaches. The other two schemes rely on breeding animals. In the second scheme, only single knockouts of heavy and light chain genes are required in male and female cell lines, respectively. This scheme does not rely on regeneration of cell lines and is technically the simplest approach but takes the longest for completion. Scheme 3 is an intermediate between schemes 1 and 2. In all schemes only Homo H/L fetuses are generated because of potential difficulties in survival and maintenance of Homo H/L knockout calves. If necessary, passive immunotherapy can be used to increase the survival of Homo H/L knockout calves.

Experimental Design The present invention preferably involves the production of a hemizygous male heavy chain knockout (M Hemi H) and a hemizygous female light chain knockout (F Hemi L) and the production of 40 day fetuses from these targeted deletions. The cells from the embryos are harvested, and one allele of the light locus is targeted in the M Hemi H cells and one allele of the heavy chain locus is targeted in the F Hemi L cells resulting in cells with hemizygous deletions of both the H and L loci (Hemi H/L). These cells are used to derive 40 day fetuses from which fibroblasts are isolated.

The M Hemi H/L fibroblasts are targeted with the other H chain allele to create M Homo H/Hemi L, and the F Hemi H/L are targeted with the other L chain allele to create F Homo L/Hemi H. In order to create homozygous deletions, higher drug concentrations are used to drive homozygous targeting. However, it is possible that this approach may not be successful and that breeding may be necessary. An exemplary strategy which relies on cre/lox targeting of the selection cassette allows the same selective systems to be used for more than one targeted deletion. These fibroblasts are cloned and 40 day fetuses harvested and fibroblast cells isolated. The fetal cells from this cloning are targeted to produce homozygous deletions of either the H or L loci resulting in M Homo H/L and F Homo H/L fetal fibroblasts. These fibroblasts are cloned and 40 day fetuses derived and fibroblasts isolated. The Homo H/L fetal fibroblasts are then used for incorporation of the HAC optionally by the use of breeding procedures.

Library Construction Fetal fibroblast cells are used to construct a genomic library. Although it is reported to be significant that the targeting construct be isogenic with the cells used for cloning, it is not essential to the invention. For example, isogenic, substantially isogenic, or nonisogenic constructs may be used to produce a mutation in an endogenous immunoglobulin gene. In one possible method, Holstein cattle, which genetically contain a high level of inbreeding compared to other cattle breeds, are used. We have not detected any polymorphisms in immunoglobulin genes among different animals. This suggests that sequence homology should be high and that targeting with nonisogenic constructs should be successful.

A library is constructed from one male cell line and one female cell line at the same time that the "clonability" testing is being conducted. It is envisioned that at the end of the process, a library will be produced and a number of different fetal cell lines will be tested and one cell line chosen as the best for cloning purposes.

Figure 2B:
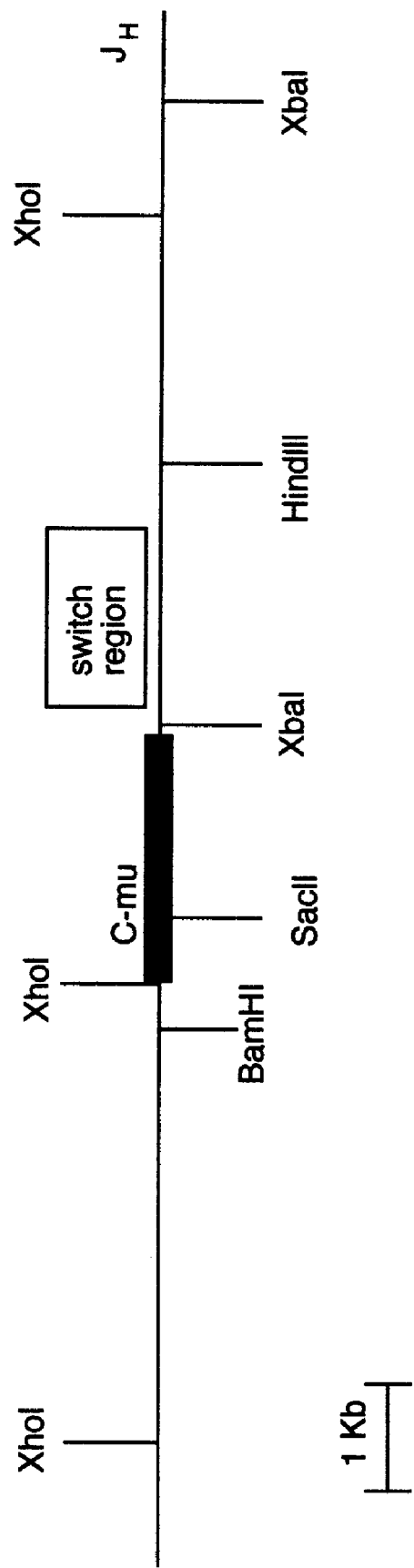
FIG. 2B is a restriction map of immunoglobulin loci from a Holstein cattle.

Genomic libraries are constructed using high molecular weight DNA isolated from the fetal fibroblast cells. DNA is size fractionated and high molecular weight DNA between 20–23 Kb is inserted into the lambda phage vector LambdaZap or LambdaFix. The inventors have had excellent success with Stratagene prepared libraries. Therefore, DNA is isolated and the size selected DNA is sent to Stratagene for library preparation. To isolate clones containing bovine heavy and light chains, radiolabeled IgM cDNA and radiolabeled light chain cDNA is used. Additionally, light chain genomic clones are isolated in case it is necessary to delete the locus. Each fetal cell library is screened for bovine heavy and light chain containing clones. It is anticipated that screening approximately $10^5$–$10^6$ plaques should lead to the isolation of clones containing either the heavy chain or light chain locus. Once isolated, both loci are subcloned into pBluescript and restriction mapped. A restriction map of these loci in Holsteins is provided in FIG. 2B (Knight et al. J Immunol 140(10):3654–9, 1988). Additionally, a map from the clones obtained is made and used to assemble the targeting construct.

Production of Targeting Constructs Once the heavy and light chain genes are isolated, constructs are made. The IgM construct is made by deleting the IgM constant region membrane domain. As shown by Rajewsky and colleagues in mice, deletion of the membrane domain of IgM results in a block in B cell development since surface IgM is a required signal for continued B cell development (Kitamura et al., Nature 350:423–6). Thus homozygous IgM cattle lack B cells. This should not pose a problem since in the present strategy no live births of animals lacking functional Ig are necessary. However, if necessary, passive immunotherapy may be used to improve the survival of the animals until the last step when the human Ig loci are introduced.

An exemplary targeting construct used to effect knockout of the IgM heavy chain allele is shown below in FIG. 2A. For the heavy chain, the membrane IgM domain is replaced with a neomycin cassette flanked by lox P sites. The attached membrane domain is spliced together with the neo cassette such that the membrane domain has a TAG stop codon inserted immediately 5' to the lox P site ensuring that the membrane domain is inactivated. This is placed at the 5' end of the targeting construct with approximately 5–6 kilobases of 3' chromosomal DNA.

If increasing drug concentrations does not allow deletion of the second allele of either IgM heavy or light chains, the cre/lox system (reviewed in Sauer, 1998, Methods 14:381–392) is used to delete the selectable marker. As described below, the cre/lox system allows the targeted deletion of the selectable marker. All selectable markers are flanked with loxP sequences to facilitate deletion of these markers if this should be necessary.

The light chain construct contains the bovine lambda chain constant region (e.g., the lambda light chain constant region found in Genbank accession number AF396698 or any other ungulate lambda light chain constant region) and a puromycin resistance gene cassette flanked by lox P sites and will replace the bovine gene with a puromycin cassette flanked by lox P sites. Approximately 5–6 kilobases of DNA 3' to the lambda constant region gene will be replaced 3' to the puromycin resistance gene. The puromycin resistance gene will carry lox P sites at both 5' and 3' ends to allow for deletion if necessary. Due to the high degree of homology between ungulate antibody genes, the bovine lambda light chain sequence in Genbank accession number AF396698 is expected to hybridize to the genomic lambda light chain sequence from a variety of ungulates and thus may be used in standard methods to isolate various ungulate lambda light chain genomic sequences. These genomic sequences may be used in standard methods, such as those described herein, to generate knockout constructs to inactivate endogenous lambda light chains in any ungulate.

A kappa light chain knockout construct may be constructed similarly using the bovine kappa light chain sequence in FIG. 3G or any other ungulate kappa light chain sequence. This bovine kappa light chain may be used as a hybridization probe to isolate genomic kappa light chain sequences from a variety of ungulates. These genomic sequences may be used in standard methods, such as those described herein, to generate knockout constructs to inactivate endogenous kappa light chains in any ungulate.

Additional ungulate genes may be optionally mutated or inactivated. For example, the endogenous ungulate Ig J chain gene may be knocked out to prevent the potential antigenicity of the ungulate Ig J chain in the antibodies of the invention that are administered to humans. For the construction of the targeting vector, the cDNA sequence of the bovine Ig J chain region found in Genbank accession number U02301 may be used. This cDNA sequence may be used as a probe to isolate the genomic sequence of bovine Ig J chain from a BAC library such as RPC1-42 (BACPAC in Oakland, Calif.) or to isolate the genomic sequence of the J chain from any other ungulate. Additionally, the human J chain coding sequence may be introduced into the ungulates of present invention for the functional expression of human IgA and IgM molecules. The cDNA sequence of human J chain is available from Genbank accession numbers AH002836, M12759, and M12378. This sequence may be inserted into an ungulate fetal fibroblast using standard methods, such as those described herein. For example, the human J chain nucleic acid in a HAC, YAC vector, BAC vector, cosmid vector, or knockin construct may be integrated into an endogenous ungulate chromosome or maintained independently of endogenous ungulate chromosomes. The resulting transgenic ungulate cells may be used in the nuclear transfer methods described herein to generate the desired ungulates that have a mutation that reduces or eliminates the expression of functional ungulate J chain and that contain a xenogenous nucleic acid that expresses human J chain.

Additionally, the ungulate α-(1,3)-galactosyltransferase gene may be mutated to reduce or eliminate expression of the galactosyl(α1,3)galactose epitope that is produced by the α-(1,3)-galactosyltransferase enzyme. If human antibodies produced by the ungulates of the present invention are modified by this carbohydrate epitope, these glycosylated antibodies may be inactivated or eliminated, when administered as therapeutics to humans, by antibodies in the recipients that are reactive with the carbohydrate epitope. To eliminate this possible immune response to the carbohydrate epitope, the sequence of bovine alpha-(1,3)-galactosyltransferase gene may be used to design a knockout construct to inactive this gene in ungulates (Genbank accession number J04989; Joziasse et al., J. Biol. Chem. 264(24):14290–7, 1989). This bovine sequence or the procine alpha-(1,3)-galactosyltransferase sequence disclosed in U.S. Pat. Nos. 6,153,428 and 5,821,117 may be used to obtain the genomic alpha-(1,3)-galactosyltransferase sequence from a variety of ungulates to generate other ungulates with reduced or eliminated expression of the galactosyl(α1,3)galactose epitope.

If desired, the ungulate prion gene may be mutated or inactivated to reduce the potential risk of an infection such as bovine spongiform encephalopathy (BSE). For the construction of the targeting vector, the genomic DNA sequence of the bovine prion gene may be used (Genbank accession number AJ298878). Alternatively, this genomic prion sequence may be used to isolate the genomic prion sequence from other ungulates. The prior gene may be inactivated using standard methods, such as those described herein or those suggested for knocking out the alpha-(1,3)-galactosyltransferase gene or prion gene in sheep (Denning et al., Nature Biothech., 19: 559–562, 2001).

For targeting the second allele of each locus, it may be necessary to assemble a new targeting construct containing a different selectable marker, if the first selectable marker remains in the cell. As described in Table 1, a variety of selection strategies are available and may be compared and the appropriate selection system chosen. Initially, the second allele is targeted by raising the drug concentration (for example, by doubling the drug concentration). If that is not successful, a new targeting construct may be employed.

The additional mutations or the gene inactivation mentioned above may be incorporated into the ungulates of the present invention using various methodologies. Once a transgenic ungulate cell line is generated for each desired mutation, crossbreeding may be used to incorporate these additional mutations into the ungulates of the present invention. Alternatively, fetal fibroblast cells which have these additional mutations can be used as the starting material for the knockout of endogenous Ig genes and/or the introduction of xenogenous Ig genes. Also, fetal fibroblast cells having a knockout mutation in endogenous Ig genes and/or containg xenogenous Ig genes can be uses as a starting material for these additional mutations or inactivations.

Targeted Deletion of Ig Loci Targeting constructs are introduced into embryonic fibroblasts, e.g., by electroporation. The cells which incorporate the targeting vector are selected by the use of the appropriate antibiotic. Clones that are resistant to the drug of choice will be selected for growth. These clones are then subjected to negative selection with gancyclovir, which will select those clones which have integrated appropriately. Alternatively, clones that survive the drug selection are selected by PCR. It is estimated that it will be necessary to screen at least 500–1000 clones to find an appropriately targeted clone. The inventors' estimation is based on Kitamura (Kitamura et al., Nature 350:423–6, 1991) who found that when targeting the membrane domain of IgM heavy chain constant region approximately 1 in 300 neo resistant clones were properly targeted. Thus, it is proposed to pool clones into groups of 10 clones in a 96 well plate and screen pools of 10 clones for the targeted clones of choice. Once a positive is identified, single clones isolated from the pooled clone will be screened. This strategy should enable identification of the targeted clone.

Because fibroblasts move in culture it is difficult to distinguish individual clones when more than approximately ten clones are produced per dish. Further, strategies may be developed for clonal propagation with high efficiency transfection. Several reasonable strategies, such as dilution cloning, may be used.

Cre/Lox Excision of the Drug Resistance Marker As shown above, exemplary targeting constructs contain selectable markers flanked by loxP sites to facilitate the efficient deletion of the marker using the cre/lox system. Fetal fibroblasts carrying the targeting vector are transfected via electroporation with a Cre containing plasmid. A recently described Cre plasmid that contains a GFPcre fusion gene [Gagneten S. et al., Nucleic Acids Res 25:3326–31 (1997)] maybe used. This allows the rapid selection of all clones that contain Cre protein. These cells are selected either by FACS sorting or by manual harvesting of green fluorescing cells via micromanipulation. Cells that are green are expected to carry actively transcribed Cre recombinase and hence delete the drug resistance marker. Cells selected for Cre expression are cloned and clones analyzed for the deletion of the drug resistance marker via PCR analysis. Those cells that are determined to have undergone excision are grown to small clones, split and one aliquot is tested in selective medium to ascertain with certainty that the drug resistance gene has been deleted. The other aliquot is used for the next round of targeted deletion.

TABLE 1

Selectable markers and drugs for selection

| Gene | Drug |
|---|---|
| Neo[r] | G418[1] |
| Hph | Hygromycin B[2] |
| Puro | Puromycin[3] |
| Ecogpt | Mycophenolic acid[4] |
| Bsr | Blasticidin S[5] |
| HisD | Histidinol[6] |
| DT-A | Diphtheria toxin[7] |

[1]Southern PJ, Berg P. 1982. Transformation of mammalian cells to antibiotic resistance with a bacterial gene under control of the SV40 early region promoter. J Mol Appl Genet 1:327–41.
[2]Santerre RF, Allen NE, Hobbs JN Jr, Rao RN, Schmidt RJ. 1984. Expression of prokaryotic genes for hygromycin B and G418 resistance as dominant-selection markers in mouse L cells. Gene 30:147–56.
[3]Wirth M, Bode J, Zettlmeissl G, Hauser H. 1988. Isolation of overproducing recombinant mammalian cell lines by a fast and simple selection procedure. Gene 73:419–26.
[4]Drews RE, Kolker MT, Sachar DS, Moran GP, Schnipper LE. 1996. Passage to nonselective media transiently alters growth of mycophenolic acid-resistant mammalian cells expressing the escherichia coli xanthine-guanine phosphoribosyltransferase gene: implications for sequential selection strategies. Anal Biochem 235:215–26.
[5]Karreman C. 1998. New positive/negative selectable markers for mammalian cells on the basis of Blasticidin deaminase-thymidine kinase fusions. Nucleic Acids Res 26:2508–10.
[6]Hartman SC, Mulligan RG. 1988. Two dominant-acting selectable markers for gene transfer studies in mammalian cells. Proc Natl Acad Sci U.S.A. 85:8047–51.
[7]Yagi T, Nada S., Watanabe N, Tamemoto H, Kohmura N, Ikawa Y, Aizawa S. 1993. A novel negative selection for homologous recombinants using diphtheria toxin A fragment gene. Anal Biochem 214:77–86.

Application of Targeting Strategies to Altering Immunoglobulin Genes of Other Ungulates To alter immunoglobulin genes of other ungulates, targeting vectors are designed to contain three main regions. The first region is homologous to the locus to be targeted. The second region is a drug selection marker that specifically replaces a portion of the targeted locus. The third region, like the first region, is homologous to the targeted locus but is not contiguous with the first region in the wild type genome. Homologous recombination between the targeting vector and the desired wild type locus results in deletion of locus sequences between the two regions of homology represented in the targeting vector and replacement of that sequence with a drug resistance marker. In preferred embodiments, the total size of the two regions of homology is approximately 6 kilobases, and the size of the second region that replaces a portion of the targeted locus is approximately 2 kilobases. This targeting strategy is broadly useful for a wide range of species from prokaryotic cells to human cells. The uniqueness of each vector used is in the locus chosen for gene targeting procedures and the sequences employed in that strategy. This approach may be used in all ungulates, including, without limitation, goats (Capra hircus), sheep (Ovis aries), and the pig (Sus scrufa), as well as cattle (Bos taurus).

The use of electroporation for targeting specific genes in the cells of ungulates may also be broadly used in ungulates. The general procedure described herein is adaptable to the introduction of targeted mutations into the genomes of other ungulates. Modification of electroporation conditions (voltage and capacitance) may be employed to optimize the number of transfectants obtained from other ungulates.

In addition, the strategy used herein to target the heavy chain locus in cattle (i.e., removal of all coding exons and intervening sequences using a vector containing regions homologous to the regions immediately flanking the removed exons) may also be used equally well in other ungulates. For example, extensive sequence analysis has been performed on the immunoglobulin heavy chain locus of sheep (*Ovis aries*), and the sheep locus is highly similar to the bovine locus in both structure and sequence (Genbank accession numbers Z71572, Z49180 through Z49188, M60441, M60440, AF172659 through AF172703). In addition to the large number of cDNA sequences reported for rearranged *Ovis aries* immunoglobulin chains, genomic sequence information has been reported for the heavy chain locus, including the heavy chain 5' enhancer (Genbank accession number Z98207), the 3' mu switch region (Z98680) and the 5' mu switch region (Z98681). The complete mRNA sequence for the sheep secreted form of the heavy chain has been deposited as accession number X59994. This deposit contains the entire sequence of four coding exons, which are very homologous to the corresponding bovine sequence.

Information on the sheep locus was obtained from Genbank and used to determine areas of high homology with bovine sequence for the design of primers used for PCR analysis. Because non-isogenic DNA was used to target bovine cells, finding areas of high homology with sheep sequence was used as an indicator that similar conservation of sequences between breeds of cow was likely. Given the similarity between the sequences and structures of the bovine and ovine immunoglobulin loci, it would be expected that the targeting strategies used to remove bovine immunoglobulin loci could be successfully applied to the ovine system. In addition, existing information on the pig (*Sus scrofa*, accession number S42881) and the goat (*Capra hircus*, accession number AF140603), indicates that the immunoglobulin loci of both of these species are also sufficiently similar to the bovine loci to utilize the present targeting strategies.

Procedures for Insertion of HACs

Essentially, male and female bovine fetal fibroblast cell lines containing human artificial chromosome sequences (#14fg., #2fg., and #22fg.) are obtained and selected and used to produce cloned calves from these lines.

For example, HACs derived from human chromosome #14 ("#14fg," comprising the Ig heavy chain gene), human chromosome #2 ("#2fg," comprising the Ig kappa chain gene) and human chromosome #22 ("#22fg," comprising the Ig lambda chain gene) can be introduced simultaneously or successively.

The transmission of these chromosome fragments is tested by mating a male #14fg. animal to female #2fg. and #22fg. animals and evaluating offspring. If transmission is successful then the two lines are mated to produce a line containing all three chromosome fragments.

Also, #14fg., #2fg., and #22fg. chromosome fragments may be inserted into Homo H/L fetal cells and used to generate cloned calves or cross transgenic HAC calves with Homo H/L calves. Alternatively, other HACs, such as ΔHAC or ΔΔHAC, may be introduced as described in Example 2 or introduced using any other chromosome transfer method.

Rationale Germline transmission of HACs should be useful for introducing the HACs into the Ig knockout animals and in propagating animals in production herds. The concern in propagation of HACs through the germline is incomplete pairing of chromosomal material during meiosis. However, germline transmission has been successful in mice as shown by Tomizuka et al. (Proc. Natl. Acad. Sci. USA, 97:722, 2000).

The strategy outlined in FIG. 1A consists of inserting #14fg. into a male line of cells and #2fg. and #22fg. each into female cell lines. Calves retaining a HAC are produced and germline transmission can be tested both through females and males. Part of the resulting offspring (~25%) should contain both heavy and light chain HACs. Further crossing should result in a line of calves containing all three chromosomal fragments. These animals are used for crossing with Homo H/L animals, produced from fetal cells as previously described.

Experimental Design Cells are obtained from the original screening of cell lines. These may be Holstein or different lines than those used above. This allows crossing while maintaining as much genetic variation in the herd as possible. Introduction of HACs into cell lines and selection of positive cell lines is then effected. Selected cell lines are used for nuclear transfer and calves are produced. Starting at 12 months of age semen and eggs are collected, fertilized, and transferred into recipient animals. Cell samples are taken for DNA marker analysis and karyotyping. Beginning at birth, blood samples are taken and analyzed for the presence of human Ig proteins.

As indicated above, HACs are also transferred into Homo H/L cell lines using the procedures developed in the above experiments.

Testing for Human Ig Expression

The goal of the experiment is to generate male Homo H cells and cloned fetuses, to insert one or more HACs that together contain human IgH and human IgL loci (such as HAC #14fg. and #22fg.) into Homo H cells and generate calves, and to test expression of human Ig response to immunization and affinity maturation. This is carried out as follows.

Experimental Design Homo H cells are generated from Hemi H cells produced as described previously. The double knockout is produced either by antibiotic selection or a second insertion. HACs are transferred into these cells as described previously. Calves are produced by nuclear transfer. Testing calves retaining a HAC begins shortly after birth and includes (1) evaluation for human Ig expression, (2) response to immunization, (3) affinity maturation, and (4) transmission of the HACs to offspring.

Human Ig expression is monitored by bleeding the animals and assaying for the presence of human heavy and light chain expression by ELISA, RT-PCR, or FACS analysis. Once it has been determined that the animals produce human Ig, animals are immunized with tetanus toxoid in adjuvant. Animals are bled once a week following immunization and responses to antigen determined via ELISA or FACS and compared to pre-bleeds collected before immunization. One month after the initial immunization, animals are boosted with an aqueous form of the antigen. One week following the boost, the animals are bled and response to antigen measured via ELISA or FACS and compared to the prebleed. The ELISA or FACS assay permits measurement of most of the titer of the response as well as the heavy chain isotypes produced. This data allows a determination of an increase in antibody titer as well as the occurrence of class switching.

Estimates of average affinity are also measured to determine if affinity maturation occurs during the response to antigen.

After the transgenic bovines have been obtained as described above, they are utilized to produce transgenic Igs, preferably human, but potentially that of other species, e.g. dog, cat, non-human primate, other ungulates such as sheep, pig, goat, murines such as mouse, rat, guinea pig, rabbit, etc. As noted, Ig genes are known to be conserved across species.

Transgenic Antisera and Milk Containing Xenogenous Antibodies

The bovine (or other ungulate) yields transgenic antisera directed to whatever antigen(s) it is endogenously exposed, or to exogenously administered antigen(s). For example, antigens may be administered to the ungulate to produce desired antibodies reactive with the antigens, including antigens such as pathogens (for example, bacteria, viruses, protozoans, yeast, or fungi), tumor antigens, receptors, enzymes, cytokines, etc. Exemplary pathogens for antibody production include, without limitation, hepatitis virus (for example, hepatitis C), immunodeficiency virus (for example, HIV), herpes virus, parvovirus, enterovirus, ebola virus, rabies virus, measles virus, vaccinia virus, *Streptococcus* (for example, *Streptococcus pneumoniae*), *Haemaphilus* (for example, *Haemophilus influenza*), *Neisseria* (for example, *Neisseria meningitis*), *Coryunebacterium diptheriae*, *Haemophilus* (for example, *Haemophilus pertussis*), *Clostridium* (for example, *Clostridium botulinium*), *Staphlococcus*, *Pseudomonas* (for example, *Pseudomonas aeruginosa*), and respiratory syncytial virus (RSV).

One or more pathogens may be administered to a transgenic ungulate to generate hyperimmune serum useful for the prevention, stabilization, or treatment of a specific disease. For example, pathogens associated with respiratory infection in children may be administered to a transgenic ungulate to generate antiserum reactive with these pathogens (e.g., *Streptococcus pneumoniae*, *Haemophilus influenza*, and/or *Neissaria meningitis*). These pathogens may optionally be treated to reduce their toxicity (e.g., by exposure to heat or chemicals such as formaldehyde) prior to administration to the ungulate.

For the generation of broad spectrum Ig, a variety of pathogens (e.g., multiple bacterial and/or viral pathogens) may be administered to a transgenic ungulate. This hyperimmune serum may be used to prevent, stabilize, or treat infection in mammals (e.g., humans) and is particularly useful for treating mammals with genetic or acquired immunodeficiencies.

In addition, antibodies produced by the methods of the invention may be used to suppress the immune system, for example, to treat neuropathies, as well as to eliminate particular human cells and modulate specific molecules. For example, anti-idiotypic antibodies (i.e., antibodies which inhibit other antibodies) and antibodies reactive with T cells, B cells, or cytokines may be useful for the treatment of autoimmune disease or neuropathy (e.g., neuropathy due to inflammation). These antibodies may be obtained from transgenic ungulates that have not been administered an antigen, or they may be obtained from transgenic ungulates that have been administered an antigen such as a B cell, T cell, or cytokine (e.g., TNFα).

Transgenic antisera generated from transgenic ungulates that have not been administered an antigen may be used to manufacture pharmaceuticals comprising human polyclonal antibodies, preferably human IgG molecules. These human antibodies may be used in place of antibodies isolated from humans as Intraveneous Immunoglobulin (IVIG) therapeutics.

Transgenic antiserum may optionally be enriched for antibodies reactive against one or more antigens of interest. For example, the antiserum may be purified using standard techniques such as those described by Ausubel et al. (Current Protocols in Molecular Biology, volume 2, p. 11.13.1–11.13.3, John Wiley & Sons, 1995). Preferred methods of purification include precipitation using antigen or antibody coated beads, column chromatography such as affinity chromatography, magnetic bead affinity purification, and panning with a plate-bound antigen. Additionally, the transgenic antiserum may be contacted with one or more antigens of interest, and the antibodies that bind an antigen may be separated from unbound antibodies based on the increased size of the antibody/antigen complex. Protein A and/or protein G may also be used to purify IgG molecules. If the expression of endogenous antibodies is not eliminated, protein A and/or an antibody against human Ig light chain lambda (Pharmingen) may be used to separate desired human antibodies from endogenous ungulate antibodies or ungulate/human chimeric antibodies. Protein A has higher affinity for human Ig heavy chain than for bovine Ig heavy chain and may be used to separate desired Ig molecules containing two human heavy chains from other antibodies containing one or two ungulate heavy chains. An antibody against human Ig light chain lambda may be used to separate desired Ig molecules having two human Ig lambda chains from those having one or two ungulate Ig light chains. Additionally or alternatively, one or more antibodies that are specific for ungulate Ig heavy or light chains may be used in a negative selection step to remove Ig molecules containing one or two ungulate heavy and/or light chains.

The resultant antisera may itself be used for passive immunization against an antigen. Alternatively, the antisera has diagnostic, prophylactic, or purification use, e.g. for attaining purification of antigens.

Alternatively, after antisera administration, B cells may be isolated from the transgenic bovine and used for hybridoma preparation. For example, standard techniques may be used to fuse a B cell from a transgenic ungulate with a myeloma to produce a hybridoma secreting a monoclonal antibody of interest (Mocikat, J. Immunol. Methods 225:185–189, 1999; Jonak et al., Hum. Antibodies Hybridomas 3:177–185, 1992; Srikumaran et al., Science 220:522, 1983). Preferred hybridomas include those generated from the fusion of a B-cell with a myeloma from a mammal of the same genus or species as the transgenic ungulate. Other preferred myelomas are from a Balb/C mouse or a human. In this instance, hybridomas are provided that make xenogenous monoclonal antibodies against a particular antigen. For example, this technology may be used to produce human, cat, dog, etc. (dependent upon the specific artificial chromosome) monoclonal antibodies that are specific to pathogens. Methods for selecting hybridomas that produce antibodies having desirable properties, i.e., enhanced binding affinity, avidity, are well known.

Alternatively, a B cell from a transgenic ungulate may be genetically modified to express an oncogene, such as ras, myc, abl, bcl2, or neu, or infected with a transforming DNA or RNA virus, such as Epstein Barr virus or SV40 virus (Kumar et al., Immunol. Lett. 65:153–159, 1999; Knight et al., Proc. Nat. Acad. Sci. USA 85:3130–3134, 1988; Shammah et al., J. Immunol. Methods /160-19-25, 1993; Gustafsson and Hinkula, Hum. Antibodies Hybridomas 5:98–104, 1994; Kataoka et al., Differentiation 62:201–211, 1997; Chatelut et al., Scand. J. Immunol. 48:659–666, 1998). The resulting immortalized B cells may also be used to produce a theoretically unlimited amount of antibody. Because Ig is also secreted into the milk of ungulates, ungulate milk may also be used as a source of xenogenous antibodies.

While the invention has been described adequately supra, the following examples are additionally provided as further exemplification of the invention.

EXAMPLE 1

Bovine IgM Knock Out

The following procedures were used to generate bovine fibroblast cell lines in which one allele of the immunoglobulin heavy chain (mu) locus is disrupted by homologous recombination. A DNA construct for effecting an IgM knockout was generated by the removal of exons 1–4 of the Mu locus (corresponds to IgM heavy chain gene) which were replaced with a copy of a neomycin resistance gene. Using this construct, neomycin resistant cell lines have been obtained which were successfully used in nuclear transfer procedures, and blastocysts from these cell lines have been implanted into recipient cows. Additionally, some of these blastocysts were tested to confirm that targeted insertion occurred appropriately in the mu locus using PCR procedures. Blastocysts resulting from nuclear transfer procedures from several of the cell lines obtained indicated that heterozygous IgM-KO fetuses were in gestation. Additionally, both male and female cell lines that comprise a single IgM heavy chain (mu) knockout have been produced. It is anticipated that mating of animals cloned from these cell lines will give rise to progeny wherein both copies of mu are inactivated. These procedures are discussed in greater detail below.

DNA Construct The DNA used in all transfections described in this document was generated as follows. The four main exons (excluding the transmembrane domain exons), CH1–4, are flanked by an XhoI restriction site at the downstream (CH4) end and an XbaI site at the upstream (CH1) end. The construct used for the transfection procedure consisted of 1.5 kb of genomic sequence downstream of the XhoI site and 3.1 Kb of genomic sequence upstream of the XbaI site (FIGS. 3D and 3E). These sequences were isolated as described herein from a Holstein cow from a dairy herd in Massachusetts. A neomycin resistance marker was inserted between these two fragments on a 3.5 Kb fragment, replacing 2.4 Kb of DNA, originally containing CH1–4, from the originating genomic sequence. The backbone of the vector was pBluescriptII SK+ (Stratagene) and the insert of 8.1 Kb was purified and used for transfection of bovine fetal fibroblasts. This construct is shown in FIGS. 3A–3C. Other mu knockout constructs containing other homologous regions and/or containing another antibiotic resistance gene may also be constructed using standard methods and used to mutate an endogenous mu heavy chain gene.

Transfection /Knockout Procedures Transfection of fetal bovine was performed using a commercial reagent, Superfect Transfection Reagent (Qiagen, Valencia, Calif., USA), Catalog Number 301305.

Bovine fibroblasts were generated from disease-tested male Charlais cattle at Hematech's Kansas facility and sent to Hematech's Worcester Molecular Biology Labs for use in all experiments described. Any other ungulate breed, genus, or species may be used as the source of donor cells (e.g., somatic cells such as fetal fibroblasts). The donor cells are genetically modified to contain a mutation that reduces or eliminates the expression of functional, endogenous Ig.

The medium used for culture of bovine fetal fibroblasts consisted of the following components: 500 ml Alpha MEM (Bio-Whittaker # 12-169F); 50 ml fetal calf serum (HyClone #A-1111-D); 2 ml antibiotic/antimyotic (Gibco/BRL #15245-012); 1.4 ml 2-mercaptoethanol (Gibco/BRL #21985-023); 5.0 ml L-Glutamine (Sigma Chemical #G-3126); and 0.5 ml tyrosine tartrate (Sigma Chemical #T-6134).

On the day prior to transfection procedures, cells were seeded in 60 mm tissue culture dishes with a targeted confluency of 40–80% as determined by microscopic examination.

On the day of transfection, 5 μg of DNA, brought to a total volume of 150 μl in serum-free, antibiotic-free medium, was mixed with 20 μl of Superfect transfection reagent and allowed to sit at room temperature for 5–10 minutes for DNA-Superfect complex formation. While the complex formation was taking place, medium was removed from the 60 mm tissue culture dish containing bovine fibroblasts to be transfected, and cells were rinsed once with 4 ml of phosphate-buffered saline. One milliliter of growth medium was added to the 170 μl DNA/Superfect mixture and immediately transferred to the cells in the 60 mm dish. Cells were incubated at 38.5° C., 50% carbon dioxide for 2.5 hours. After incubation of cells with the DNA/Superfect complexes, medium was aspirated off and cells were washed four times with 4 ml PBS. Five ml of complete medium were added and cultures were incubated overnight at 38.5° C., 5% $CO_2$. Cells were then washed once with PBS and incubated with one ml of 0.3% trypsin in PBS at 37° C. until cells were detached from the plate, as determined by microscopic observation. Cells from each 60 mm dish were split into 24 wells of a 24 well tissue culture plate (41.7 ul/well). One milliliter of tissue culture medium was added to each well and plates were allowed to incubate for 24 hours at 38.5° C. and 5% $CO_2$ for 24 hours.

During all transfection procedures, sham transfections were performed using a Superfect/PBS mixture containing no DNA, as none of those cells would be expected to contain the neomycin resistance gene and all cells would be expected to die after addition of G418 to the tissue culture medium. This served as a negative control for positive selection of cells that received DNA.

After the 24 hour incubation, one more milliliter of tissue culture medium containing 400 μg G418 was added to each well, bringing the final G418 concentration to 200 μg/ml. Cells were placed back into the incubator for 7 days of G418 selection. During that period, both transfected and sham transfection plates were monitored for cell death and over 7 days, the vast majority of wells from the sham transfections contained few to no live cells while plates containing cells that received the DNA showed excellent cell growth.

After the 7 day selection period, the cells from wells at 90–100% confluency were detached using 0.2 ml 0.3% trypsin in PBS and were transferred to 35 mm tissue culture plates for expansion and incubated until they became at least 50% confluent, at which point, cells were trypsinized with 0.6 ml 0.3% trypsin in PBS. From each 35 mm tissue culture plate, 0.3 ml of the 0.6 ml cell suspension was transferred to a 12.5 $cm^2$ tissue culture flask for further expansion. The remaining 0.3 ml was reseeded in 35 mm dishes and incubated until they attained a minimal confluency of approximately 50%, at which point cells from those plates were processed for extraction of DNA for PCR analysis. Flasks from each line were retained in the incubator until they had undergone these analyses and were either terminated if they did not contain the desired DNA integration or kept for future nuclear transfer and cryopreservation.

Screening for Targeted Integrations As described above the DNA source for screening of transfectants containing the DNA construct was a 35 mm tissue culture dish containing a passage of cells to be analyzed. DNA was prepared as follows and is adapted from a procedure published by Laird et al. (Laird et al., "Simplified mammalian DNA isolation procedure", *Nucleic Acids Research*, 19:4293). Briefly, DNA was prepared as follows. A cell lysis buffer was prepared with the following components: 100 mM Tris-HCl buffer, pH 8.5; 5 mM EDTA, pH 8.0; 0.2% sodium dodecyl sulfate; 200 mM NaCl; and 100 ug/ml Proteinase K.

Medium was aspirated from each 35 mm tissue culture dish and replaced with 0.6 ml of the above buffer. Dishes were placed back into the incubator for three hours, during which time cell lysis and protein digestion were allowed to occur. Following this incubation, the lysate was transferred to a 1.5 ml microfuge tube and 0.6 ml of isopropanol was added to precipitate the DNA. Tubes were shaken thoroughly by inversion and allowed to sit at room temperature for 3 hours, after which the DNA precipitates were spun down in a microcentrifuge at 13,000 rpm for ten minutes. The supernatant from each tube was discarded and the pellets were rinsed with 70% ethanol once. The 70% ethanol was aspirated off and the DNA pellets were allowed to air-dry. Once dry, each pellet was resuspended in 30–50 ul of Tris (10 mM)-EDTA (1 mM) buffer, pH 7.4 and allowed to hydrate and solubilize overnight. 5–7 microliters of each DNA solution was used for each polymerase chain reaction (PCR) procedure.

Two separate PCR procedures were used to analyze transfectants. The first procedure used two primers that were expected to anneal to sites that are both located within the DNA used for transfection. The first primer sequence is homologous to the neomycin resistance cassette of the DNA construct and the second is located approximately 0.5 Kb away, resulting in a short PCR product of 0.5 Kb. In particular, primers Neo1 (5'-CTT GAA GAC GAA AGG GCC TCG TGA TAC GCC-3', SEQ ID NO: 42) and IN2521 (5'-CTG AGA CTT CCT TTC ACC CTC CAG GCA CCG-3', SEQ ID NO: 43) were used. A Qiagen PCR kit was used for this PCR reaction. The PCR reaction mixture contained 1 pmole of each primer, 5 ul of 10× reaction buffer, 10 ul of Q solution, 5 ul of DNA, and 1 ul of dNTP solution. The reaction mixture was brought to a total volume of 50 ul with H$_2$O. This PCR amplification was performed using an initial denaturing incubation at 94° C. for two minutes. Then, 30 cycles of denaturation, annealing, and amplification were performed by incubation at 94° C. for 45 seconds, 60° C. for 45 seconds, and 72° C. for two minutes. Then, the reaction mixture was incubated at 72° C. for five minutes and at 4° C. until the mixture was removed from the PCR machine. Alternatively, any other primers that are homologous to the region of the knockout construct that integrates into the genome of the cells may be used in a standard PCR reaction under appropriate reaction conditions to verify that cells surviving G418 selection were resistant as a result of integration of the DNA construct.

Because only a small percentage of transfectants would be expected to contain a DNA integration in the desired location (the Mu locus), another pair of primers was used to determine not only that the DNA introduced was present in the genome of the transfectants but also that it was integrated in the desired location. The PCR procedure used to detect appropriate integration was performed using one primer located within the neomycin resistance cassette of the DNA construct and one primer that would be expected to anneal over 1.8 Kb away, but only if the DNA had integrated at the appropriate site of the IgM locus (since the homologous region was outside the region included in the DNA construct used for transfection). The primer was designed to anneal to the DNA sequence immediately adjacent to those sequences represented in the DNA construct if it were to integrate in the desired location (DNA sequence of the locus, both within the region present in the DNA construct and adjacent to them in the genome was previously determined). In particular, primers Neo1 and OUT3570 (5'-CGA TGA ATG CCC CAT TTC ACC CAA GTC TGT C-3', SEQ ID NO: 44) were used for this analysis. This PCR reaction was performed using a Qiagen PCR kit as described above for the first PCR reaction to confirm the integration of the targeting construct into the cells. Alternatively, this PCR analysis may be performed using any appropriate reaction conditions with any other primer that is homologous to a region of the knockout construct that integrates into the genome of the cells and any other primer that is homologous to a region in the genome of the cells that is upstream or downstream of the site of integration.

Using these methods, 135 independent 35 mm plates were screened for targeted integration of the DNA construct into the appropriate locus. Of those, DNA from eight plates was determined to contain an appropriately targeted DNA construct and of those, three were selected for use in nuclear transfer procedures. Those cells lines were designated as "8-1C", "5-3C" and "10-1C". Leftover blastocysts not used for transfer into recipient cows were used to extract DNA which was subjected to additional PCR analysis. This analysis was effective using a nested PCR procedure using primers that were also used for initial screening of transfected lines.

As noted above, three cell lines were generated using the gene targeting construct designed to remove exons 1–4 of the mu locus. These lines all tested positive for targeted insertions using a PCR based test and were used for nuclear transfers. Leftover blastocysts resulting from those nuclear transfers were screened by PCR testing the appropriately targeted construct. The following frequencies of positive blastocysts were obtained:

| | |
|---|---|
| Cell Line 8-1C: | 6/8 |
| Cell Line 10-1C: | 2/16 |
| Cell Line 5-3C: | 0/16 |

Although at forty days of gestation, 11 total pregnancies were detected by ultrasound, by day 60, 7 fetuses had died. The remaining 4 fetuses were processed to regenerate new fetal fibroblasts and remaining organs were used to produce small tissue samples for PCR analysis. The results of the analyses are below:

| | |
|---|---|
| Line 8-1C: | two fetuses, one fetus positive for targeted insertion by PCR |
| Line 10-1C: | one fetus, positive for targeted insertion by PCR |
| Line 5-3C: | one fetus, negative for targeted insertion by PCR |

Surprisingly, although the frequency of 10-1 C blastocysts testing positive for targeted insertion was only 2/16, the one viable 60-day fetus obtained from that cell line was positive as determined by PCR. A positive fetus from 8-1C was also obtained. Southern blot analysis of DNA of all tissue samples is being effected to verify that the construct not only targeted correctly at one end (which is determined by PCR of the shorter region of homology present in the original construct) but also at the other end. Based on results to date, it is believed that two heavy chain knockout fetuses from two independent integration events have been produced. Also, since these fetuses were derived from two different lines, at least one is likely to have integrated construct correctly at both ends. Once the Southern blot analyses have confirmed appropriate targeting of both ends of targeting construct, further nuclear transfers will be performed to generate additional fetuses which will be carried to term.

Nuclear Transfer and Embryo Transfer Nuclear transfers were performed with the K/O cell line (8-1-C (18)) and eight embryos were produced. A total of six embryos from this batch were transferred to three disease free recipients at Trans Ova Genetics ("TOG"; Iowa).

Frozen embryos have been transferred to ten disease free recipients to obtain disease free female fibroblast cell lines. Fetal recoveries are scheduled after confirming the pregnancies at 35–40 days.

Pregnancy Diagnosis and Fetal Recovery Pregnancy status of the eighteen recipients transferred with cloned embryos from knockout fetal cells was checked by ultrasonography. The results are summarized below.

TABLE 2

Pregnancy at 40 days using mu heavy chain knockout donor cells

| Clone ID | No of recips transferred | Pregnancy at 40 days (%) |
|---|---|---|
| 8-1-0C | 5 | 4 (80) |
| 10-1-C | 6 | 4 (67) |
| 5-3-C | 5 | 3 (60) |
| Total | 16 | 11 (69) |

Pregnancy Diagnosis Pregnancy status of the three recipients to whom cloned embryos were transferred from knockout cells (8-1C) was checked; one was open and the other two required reconfirmation after one month.

Fetal Recoveries and Establishment of Cell Lines Eleven pregnancies with the K/O embryos at 40 days were obtained. Four live fetuses were removed out of these at 60 days. Cell lines were established from all four and cryopreserved for future use. Also we collected and snap froze tissue samples from the fetuses and sent them to Hematech molecular biology laboratory for PCR/Southern blot analysis.

All four of the cell lines were male. In order to secure a female cell line, cell lines were established and cryopreserved for future establishment of K/O cells from the fetuses (six) collected at 55 days of gestation from the pregnancies established at Trans Ova Genetics with disease free recipients. Recently, the existence of a female cell line containing a mu knockout was confirmed. This female cell line may be used to produce cloned animals which may be mated with animals generated from the male cell lines, and progeny screened for those that contain the double mu knockout.

EXAMPLE 2

Introduction of HAC

Additional experiments were carried out to demonstrate that immunoglobulin heavy chain (mu) and lambda light chain may be produced by a bovine host, either alone or in combination. In addition, these experiments demonstrated that the immunoglobulin chains were rearranged and that polyclonal sera was obtained. In these procedures, immunoglobulin-expressing genes were introduced into bovine fibroblasts using human artificial chromosomes. The fibroblasts were then utilized for nuclear transfer, and fetuses were obtained and analyzed for antibody production. These procedures and results are described in more detail below.

HAC Constructs The human artificial chromosomes (HACs) were constructed using a previously described chromosome-cloning system (Kuroiwa et al., Nature Biotech. 18: 1086–1090, 2000). Briefly, for the construction of ΔHAC, the previously reported human chromosome 22 fragment (hChr22) containing a loxP sequence integrated at the HCF2 locus was truncated at the AP000344 locus by telomere-directed chromosomal truncation (Kuroiwa et al., Nucleic Acid Res., 26: 3447–3448, 1998). Next, cell hybrids were formed by fusing the DT40 cell clone containing the above hChr22 fragment (hCF22) truncated at the AP000344 locus with a DT40 cell clone (denoted "R clone") containing the stable and germline-transmittable human minichromosome SC20 vector. The SC20 vector was generated by inserting a loxP sequence at the RNR2 locus of the S20 fragment. The SC20 fragment is a naturally-occurring fragment derived from human chromosome 14 that includes the entire region of the human Ig heavy chain gene (Tomizuka et al., Proc. Natl. Acad. Sci. USA 97:722, 2000). The resulting DT40 cell hybrids contained both hChr fragments. The DT40 hybrids were transfected with a Cre recombinase-expression vector to induce Cre/loxP-mediated chromosomal translocation between hCF22 and the SC20 vector. The stable transfectants were analyzed using nested PCR to confirm the cloning of the 2.5 megabase hChr22 region, defined by the HCF2 and AP000344 loci, into the loxP-cloning site in the SC20 vector. The PCR-positive cells which were expected to contain ΔHAC were then isolated by FACS sorting based on the fluorescence of the encoded green fluorescent protein. Fluorescent in situ hybridization (FISH) analysis of the sorted cells was also used to confirm the presence of ΔHAC, which contains the 2.5 megabase hChr22 insert.

Similarly, ΔΔHAC was also constructed using this chromosome-cloning system. The hChr22 fragment was truncated at the AP000344 locus, and then the loxP sequence was integrated into the AP000553 locus by homologous recombination in DT40 cells. The resulting cells were then fused with the R clone containing the SC20 minichromosome vector. The cell hybrids were transfection with a Cre-expression vector to allow Cre/loxP-mediated chromosomal translocation. The generation of ΔΔHAC, which contains the 1.5 megabase hChr22 insert, defined by the AP000553 and AP000344 loci, was confirmed by PCR and FISH analyses.

The functionality of ΔHAC and ΔΔHAC in vivo was assessed by the generation of chimeric mice containing these HACs. These HACs were individually introduced into mouse embryonic stem (ES) cells, which were then used for the generation of chimeric mice using standard procedures (Japanese patent number 2001–142371; filed May 11, 2000). The resulting mice had a high degree of chimerism (85–100% of coat color), demonstrating a high level of pluripotency of the ES cells containing these HACs and the mitotic stability of these HACs in vivo. Furthermore, ΔHAC was transmitted through the germline of the ΔHAC chimeric mouse to the next offspring, demonstrating the meiotic stability of this HAC.

Chicken DT40 cells retaining these HACs have been deposited under the Budapest treaty on May 9, 2001 in the International Patent Organism Depository, National Institute of Advanced Industrial Science and Technology, Tsukuba Central 6, 1-1, Higashi 1-Chome Tsukuba-shi, Ibaraki-ken, 305-8566 Japan. The depository numbers are as follows: ΔHAC (FERM BP-7582), ΔΔHAC (FERM BP-7581), and SC20 fragment (FERM BP-7583). Chicken DT40 cells retaining these HACs have also been deposited in the Food Industry Research and Development Institute (FIRDI) in Taiwan. The depository numbers and dates are as follows: ΔHAC (CCRC 960144; Nov. 9, 2001), ΔΔHAC (CCRC 960145; Nov. 9, 2001), and SC20 fragment (the cell line was deposited under the name SC20 (D); CCRC 960099; Aug. 18, 1999).

The 2.5 megabase (Mb) hChr22 insert in ΔHAC is composed of the following BAC contigs, which are listed by Genbank accession number: AC002470, AC002472, AP000550, AP000551, AP000552, AP000556, AP000557, AP000558, AP000553, AP000554, AP000555, D86995, D87019, D87012, D88268, D86993, D87004, D87022, D88271, D88269, D87000, D86996, D86989, D88270, D87003, D87018, D87016, D86999, D87010, D87009, D87011, D87013, D87014, D86991, D87002, D87006, D86994, D87007, D87015, D86998, D87021, D87024, D87020, D87023, D87017, AP000360, AP00361, AP000362, AC000029, AC000102, U07000, AP000343, and AP000344. The 1.5 Mb hChr22 insert in ΔΔHAC is composed of the following BAC contigs: AP000553, AP000554, AP000555, D86995, D87019, D87012, D88268, D86993, D87004, D87022, D88271, D88269, D87000, D86996, D86989, D88270, D87003, D87018, D87016, D86999, D87010, D87009, D87011, D87013, D87014, D86991, D87002, D87006, D86994, D87007, D87015, D86998, D87021, D87024, D87020, D87023, D87017, AP000360, AP00361, AP000362, AC000029, AC000102, U07000, AP000343, and AP000344 (Dunham et al, Nature 402:489-499, 1999).

Generation of Bovine Fetal Fibroblasts To generate bovine fetal fibroblasts, day 45 to 60 fetuses were collected from disease-tested Holstein or Jersey cows housed at Trans Ova (Iowa), in which the pedigree of the male and female parents were documented for three consecutive generations. The collected fetuses were shipped on wet ice to Hematech's Worcester Molecular Biology Division for the generation of primary fetal fibroblasts. Following arrival, the fetus(es) were transferred to a non-tissue culture grade, 100 mm plastic petri dish in a tissue culture hood. Using sterile forceps and scissors, the extraembryonic membrane and umbilical cord were removed from the fetus. After transferring the fetus to a new plastic petri dish, the head, limbs and internal organs were removed. The eviscerated fetus was transferred to a third petri dish containing approximately 10 ml of fetus rinse solution composed of: 125 ml 1× Dulbecco's-PBS (D-PBS) with $Ca^{2+}$ and $Mg^{2+}$ (Gibco-BRL, cat#. 14040); 0.5 ml Tylosine Tartrate (8 mg/ml, Sigma, cat#. T-3397); 2 ml Penicillin-Streptomycin (Sigma, cat#. P-3539); and 1 ml of Fungizone (Gibco-BRL, cat#. 15295-017) (mixed and filtered through a 0.2 μm nylon filter unit [Nalgene, cat#. 150-0020).

The fetus was washed an additional three times with the fetus rinse solution to remove traces of blood, transferred to a 50 ml conical tissue culture tube, and finely minced into small pieces with a sterile scalpel. The tissue pieces were washed once with 1×D-PBS without $Ca^{2+}$ and $Mg^{2+}$ (Gibco-BRL, cat#. 14190). After the tissue pieces settled to the bottom of the tube, the supernatant was removed and replaced with approximately 30 ml of cell dissociation buffer (Gibco-BRL, cat#. 13151-014). The tube was inverted several times to allow mixing and incubated at 38.5° C./5% $CO_2$ for 20 minutes in a tissue culture incubator. Following settling of the tissue to the bottom of the tube, the supernatant is removed and replaced with an equivalent volume of fresh cell dissociation buffer. The tissue and cell dissociation buffer mixture was transferred to a sterile, 75 ml glass trypsinizing flask (Wheaton Science Products, cat#. 355393) containing a 24 mm, round-ended, spin bar. The flask was transferred to a 38.5° C./5% $CO_2$ tissue culture incubator, positioned on a magnetic stir plate, and stirred at a sufficient speed to allow efficient mixing for approximately 20 minutes. The flask was transferred to a tissue culture hood; the tissue pieces allowed to settle, followed by removal of the supernatant and harvesting of the dissociated cells by centrifugation at 1,200 rpm for five minutes. The cell pellet was re-suspended in a small volume of complete fibroblast culture media composed of: 440 ml alpha MEM (BioWhittaker, cat#. 12-169F); 50 ml irradiated fetal bovine serum; 5 ml GLUTAMAX-I supplement (Gibco-BRL, cat#. 25050-061); 5 ml Penicillin-Streptomycin (Sigma, cat#. P-3539); 1.4 ml 2-mercaptoethanol (Gibco-BRL, cat#. 21985-023) (all components except the fetal bovine serum were mixed were filtered through 0.2 μm nylon filter unit [Nalgene, cat#. 151-4020]), and stored on ice. The dissociation process was repeated three additional times with an additional 30 ml of cell dissociation solution during each step. Cells were pooled; washed in complete fibroblast media; passed sequentially through 23 and 26 gauge needles, and finally through a 70 μm cell strainer (B-D Falcon, cat#. 352350) to generate a single cell suspension. Cell density and viability were determined by counting in a hemacytometer in the presence of trypan blue (0.4% solution, Sigma, cat#. T-8154).

Primary fibroblasts were expanded at 38.5° C./5% $CO_2$ in complete fibroblast media at a cell density of $1 \times 10^6$ viable cells per T75 $cm^2$ tissue culture flask. After 3 days of culture or before the cells reached confluency, the fibroblasts were harvested by rinsing the flask once with 1×D-PBS (without $Ca^{2+}$ and $Mg^{2+}$) and incubating with 10 ml of cell dissociation buffer for 5 to 10 minutes at room temperature. Detachment of cells was visually monitored using an inverted microscope. At this step, care was taken to ensure that cell clumps were disaggregated by pipeting up-and-down. After washing and quantitation, the dissociated fibroblasts were ready for use in gene targeting experiments. These cells could also be cryopreserved for long-term storage.

Introduction of HACs into Bovine Fetal Fibroblasts ΔHAC and ΔΔHAC were transferred from the DT40 cell hybrids to Chinese hamster ovary (CHO) cells using microcell-mediated chromosome transfer (MMCT) (Kuroiwa et al. Nature Biotech. 18: 1086-1090, 2000). The CHO clone containing ΔHAC ("D15 clone") was cultured in F12 (Gibco) medium supplemented with 10% FBS (Gibco), 1 mg/ml of G418, and 0.2 mg/ml of hygromycin B at 37° C. and 5% $CO_2$. The D15 clone was expanded into twelve T25 flasks. When the confluency reached 80-90%, colcemid (Sigma) was added to the medium at a final concentration of 0.1 μg/ml. After three days, the medium was exchanged with DMEM (Gibco) supplemented with 10 μg/ml of cytochalacin B (Sigma). The flasks were centrifuged for 60 minutes at 8,000 rpm to collect microcells. The microcells were purified through 8, 5, and 3-μm filters (Costar) and then resuspended in DMEM medium. The microcells were used for fusion with bovine fibroblasts as described below.

Bovine fetal fibroblasts were cultured in α-MEM (Gibco) medium supplemented with 10% FBS (Gibco) at 37° C. and 5% $CO_2$. The fibroblasts were expanded in a T175 flask. When the confluency reached 70–80%, the cells were detached from the flask with 0.05% trypsin. The fibroblast cells were washed twice with DMEM medium and then overlayed on the microcell suspension. After the microcell-fibroblast suspension was centrifuged for five minutes at 1,500 rpm, PEG1500 (Roche) was added to the pellet according to the manufacturer's protocol to enable fusion of the microcells with the bovine fibroblasts. After fusion, the fused cells were plated into six 24-well plates and cultured in α-MEM medium supplemented with 10% FBS for 24 hours. The medium was then exchanged with medium containing 0.7 mg/ml of G418. After growth in the presence of the G418 antibiotic for about two weeks, the G418 resistant, fused cells were selected. These G418-resistant clones were used for nuclear transfer, as described below.

Similarly, ΔΔHAC from the CHO clone ΔΔC13 was transferred into bovine fetal fibroblasts by means of MMCT. The selected G418-resistant clones were used for nuclear transfer.

Nuclear Transfer, Activation, and Embryo Culture The nuclear transfer procedure was carried out essentially as described earlier (Cibelli et al., Science 1998: 280:1256–1258). In vitro matured oocytes were enucleated about 18–20 hours post maturation (hpm) and chromosome removal was confirmed by bisBenzimide (Hoechst 33342, Sigma) labeling under UV light. These cytoplast-donor cell couplets were fused, by using single electrical pulse of 2.4 kV/cm for 20 μsec (Electrocell manipulator 200, Genetronics, San Diego, Calif.). After 3–4 hrs, a random sub-set of 25% of the total transferred couplets was removed, and the fusion was confirmed by bisBenzimide labeling of the transferred nucleus. At 30 hpm reconstructed oocytes and controls were activated with calcium ionophore (5 μM) for 4 minutes (Cal Biochem, San Diego, Calif.) and 10 μg Cycloheximide and 2.5 μg Cytochalasin D (Sigma) in ACM culture medium for 6 hours as described earlier (Lin et al., Mol. Reprod. Dev. 1998: 49:298–307; Presicce et al., Mol. Reprod. Dev. 1994:38:380–385). After activation eggs were washed in HEPES buffered hamster embryo culture medium (HECM-Hepes) five times and placed in culture in 4-well tissue culture plates containing irradiated mouse fetal fibroblasts and 0.5 ml of embryo culture medium covered with 0.2 ml of embryo tested mineral oil (Sigma). Twenty five to 50 embryos were placed in each well and incubated at 38.5° C. in a 5% $CO_2$ in air atmosphere. On day four 10% FCS was added to the culture medium.

Embryo Transfer Day 7 and 8 nuclear transfer blastocysts were transferred into day 6 and 7 synchronized recipient heifers, respectively. Recipient animals were synchronized using a single injection of Lutalyse (Pharmacia & Upjohn, Kalamazoo, Mich.) followed by estrus detection. The recipients were examined on day 30 and day 60 after embryo transfer by ultrasonography for the presence of conceptus and thereafter every 30 days by rectal palpation until 270 days. The retention of a HAC in these bovine fetuses is summarized in Table 3 and is described in greater detail in the sections below.

TABLE 3

Summary of HAC retention in bovine fetuses

| HAC | Cell Clone | Recip/Fetus No. | NT Date | Recovery Date | Fetal Age | HAC Retention H | L |
|---|---|---|---|---|---|---|---|
| ΔΔ | 4-12 | 5580 | 2/14 | 4/13 | 58 | + | + |
| ΔΔ | 2-14 | 5848 | 2/15 | 4/13 | 57 | − | − |
| ΔΔ | 4-12 | 5868A | 2/14 | 6/13 | 119 | + | + |
| ΔΔ | 4-12 | 5868B | 2/14 | 6/13 | 119 | + | + |
| ΔΔ | 4-12 | 5542A | 2/14 | 5/16 | 91 | + | + |
| ΔΔ | 4-12 | 5542B | 2/14 | 5/16 | 91 | + | + |
| ΔΔ | 4-12 | 5174 | 2/14 | 5/16 | 91 (abnormal) | nd | nd |
| ΔΔ | 4-12 | 6097 | 2/14 | Remains | 160 (7/24) | nd | nd |
| Δ | 4-8 | 6032 | 1/31 | 3/30 | 58 | + | + |
| Δ | 2-13 | 5983 | 2/2 | 3/30 | 56 | − | − |
| Δ | 4-2 | 5968 | 2/2 | 3/30 | 56 | + | + |
| Δ | 2-22 | 6045 | 2/2 | 3/30 | 56 | + | + |
| Δ | 4-8 | 5846 | 1/31 | 4/20 | 79 | − | − |
| Δ | 2-13 | 6053 | 2/2 | 4/27 | 84 | + | − |
| Δ | 4-2 | 5996 | 2/1 | 4/20 | 77 | + | − |

Introduction of a HAC Containing a Fragment of Human Chromosome #14 The SC20 fragment, a human chromosome #14 fragment ("hchr.14fg", containing the Ig heavy chain gene), was introduced into fetal fibroblast cells in substantially the same manner as described above. Any other standard chromosome transfer method may also be used to insert this HAC or another HAC containing a human Ig gene into donor cells. The resulting donor cells may be used in standard nuclear transfer techniques, such as those described above, to generate transgenic ungulates with the HAC.

The pregnancy status of the 28 recipients to whom cloned embryos were transferred from cells containing the hchr.14fg was checked by ultrasonography. The results are summarized in Table 4.

TABLE 4

Pregnancy at 40 days using donor cells containing hchr.14fg

| Clone ID | No of recips transferred | Pregnancy at 40 days (%) |
|---|---|---|
| 2-1 | 08 | 03 (38) |
| 4-2 | 10 | 00 (00) |
| 4-1 | 05 | 00 (00) |
| 4-1 | 03 | 01 (33) |
| 2-1 | 02 | 01 (50) |
| Total | 28 | 05 (18) |

The pregnancy rates were lower than anticipated. This is believed to be attributable to extremely abnormally hot weather during embryo transfer.

As illustrated in FIG. 27, pregnancy rates for HAC carrying embryos appear to be equivalent to non-transgenic cloned pregnancies. One recipient carrying a ΔΔHAC calf gave birth recently to a live healthy calf. Others will be born over the next several months Demonstration of Rearrangement and Expression of Human Heavy Chain Locus in a ΔHAC Bovine Fetus Cloned ΔHAC-transgenic bovine fetuses were removed at various gestational days and analyzed for the presence, rearrangement, and expression of the human immunoglobulin loci. Analysis of genomic DNA and cDNA obtained by RT-PCR from spleen and nonlymphoid tissues (liver and brain) of one of these fetuses indicated the presence, rearrangement, and expression of the ΔHAC.

Presence of Human Heavy and/or Light Chain in ΔHAC Fetuses To determine whether the human heavy and light chains were retained in ΔHAC fetuses, liver DNA was isolated from ΔHAC fetuses and analyzed by PCR for the presence of genomic DNA encoding human heavy and light chains.

For the detection of genomic heavy chain DNA, the following primers were used: VH3-F 5'-AGTGAGATAAG-CAGTGGATG-3' (SEQ ID NO: 1) and VH3-R 5'-CTTGT-GCTACTCCCATCACT-3' (SEQ ID NO: 2). The primers used for detection of lambda light chain DNA were IgL-F 5'-GGAGACCACCAAACCCTCCAAA-3' (SEQ ID NO: 3) and IgL-R 5'-GAGAGTTGCAGAAGGGGTYGACT-3' (SEQ ID NO: 4). The PCR reaction mixtures contained 18.9 µl water, 3 µl of 10×Ex Taq buffer, 4.8 µl of dNTP mixture, 10 pmol forward primer and 10 pmol of reverse primer, 1 µl of genomic DNA, and 0.3 µl of Ex Taq. Thirty-eight cycles of PCR were performed by incubating the reaction mixtures at the following conditions: 85° C. for three minutes, 94° C. for one minute, 98° C. for 10 seconds, 56° C. for 30 seconds, and 72° C. for 30 seconds.

Figure 5:
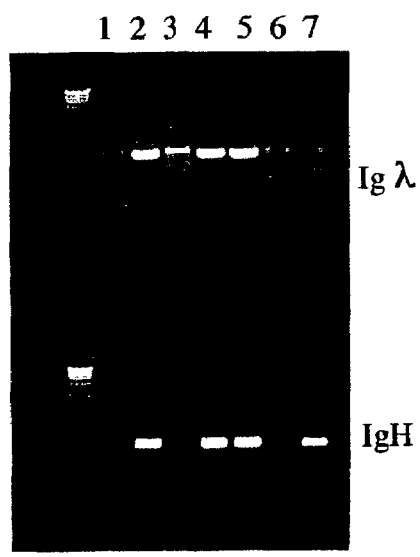
FIG. 5 is a picture of an agarose gel showing the presence of genomic DNA encoding human heavy and light chains in ΔHAC fetuses.

As shown in FIG. 5, fetuses #5968, 6032 and 6045 each contained both human heavy chain (µ) and light chain (λ) loci. Fetus #5996 contained only the human heavy chain locus. Fetus #5983 did not contain the human heavy chain and may not have contained the human light chain. Fetus #5846 did not contain either human sequence. Thus, fetuses #5983 and 5846 may not have retained the HAC. These results suggested that ΔHAC can be stably retained up to gestational day 58 in bovines.

Presence of Human Cmu Exons in ΔHAC Fetus #5996 Primers specific for a mRNA transcript including portions of Cmu 3 and Cmu 4 were used to determine whether ΔHAC was present and expressing transcripts encoding the constant region of the human mu locus of fetus #5996.

Figure 7:
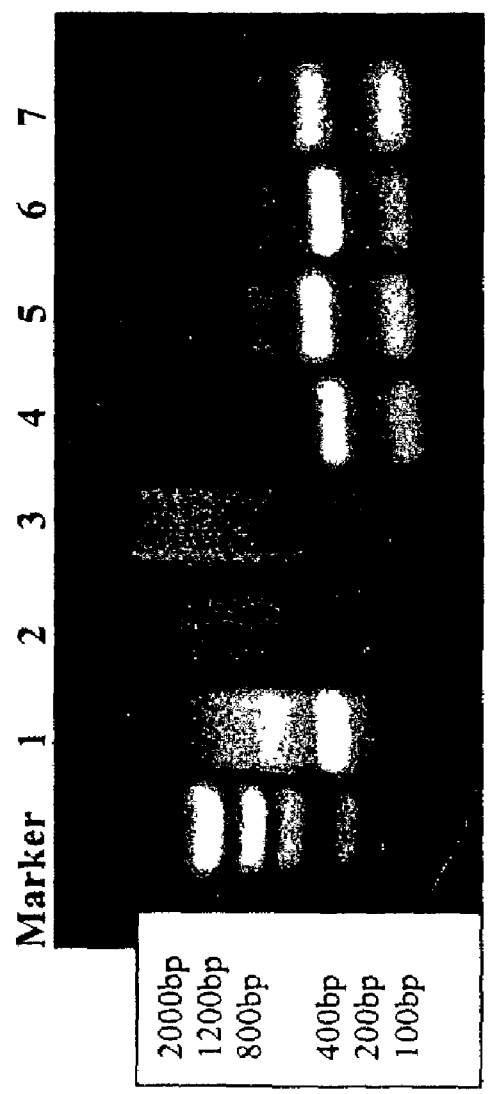
FIG. 7 is a picture of an agarose gel showing the rearrangement of endogenous bovine heavy chain in ΔHAC fetus #5996

For this RT-PCR analysis of the genomic constant region of the human mu heavy chain, primers "CH3-F1" (5'accac-ctatgacagcgtgac-3', SEQ ID NO: 5) and "CH4-R2" (5'-gtggcagcaagtagacatcg-3', SEQ ID NO: 6) were used to generate a RT-PCR product of 350 base pairs. This PCR amplification was performed by an initial denaturing incubation at 95° C. for five minutes. Then, 35 cycles of denaturation, annealing, and amplification were performed by incubation at 95° C. for one minute, 59° C. for one minute, and 72° C. for two minutes. Then, the reaction mixtures were incubated at 72° C. for 10 minutes. Rearranged bovine heavy chain was detected using primers I7L and P9, as described below (FIG. 7). As an internal control, levels of GAPDH RNA was detected using primers "GAPDH forward" (5'-gtcatcatctctgccccttctg-3', SEQ ID NO: 7) and "GAPDH reverse" (5'-aacaacttcttgatgtcatcat-3', SEQ ID NO: 8). For this amplification of GAPDH RNA, samples were incubated at 95° C. for five minutes, followed by 35 cycles of incubation at 95° C. for one minute, 55° C. for one minute, and 72° C. for two minutes. Then, the mixtures were incubated at 72° C. for seven minutes.

This analysis showed that RT-PCR analysis of the spleen of fetus #5996 produced a band (lane 3) matching the amplification products generated using control human spleen cDNA (lane 4) and cDNA obtained from a ΔHAC chimeric mouse (lane 5) (FIG. 6). No such band was detected in nonlymphoid tissues: bovine liver (lane 1) or bovine brain (lane 2). The capacity of these tissues to support RT-PCR was shown by the successful amplification of the housekeeping gene, GADPH, in both liver (lane 10 of FIG. 6) and brain (lane 6 of FIG. 7).

Rearrangement of Bovine Heavy Chain Locus by 77 Gestational Days The ΔHAC fetus #5996 was tested to determine whether it had undergone the developmental processes necessary for the expression and activation of the recombination system required for immunoglobulin heavy chain locus rearrangement. For this analysis, standard RT-PCR analysis was performed to detect the presence of mRNA transcripts encoding mu-VH rearrangements. RNA isolated from the spleen, liver, and brain of fetus #5996 was analyzed by RT-PCR using primers "17L" (5'-ccctcctctttgt-gctgtca-3', SEQ ID NO: 9) and "P9" (5'-caccgtgctctcatcg-gatg-3', SEQ ID NO: 10). The PCR reaction mixtures were incubated at 95° C. for 3 minutes, and then 35 cycles of denaturation, annealing, and amplification were performed using the following conditions: 95° C. for one minute, 58° C. for one minute, and 72° C. for two minutes. The reaction mixture was then incubated at 72° C. for 10 minutes.

Lane 5 of FIG. 7 shows that a product of the size expected for amplification of a rearranged bovine heavy chain (450 base pairs) was obtained. This product migrated to a position equivalent to that of a control bovine Cmu heavy chain cDNA known to contain sequences corresponding to rearranged bovine heavy chain transcripts (lane 7). As expected, the rearranged heavy chain was expressed in the spleen (lane 5), but absent from the brain (lane 2) and liver (lane 3) at this point in development.

Rearrangement and Expression of the Human Heavy Chain Locus in the ΔHAC Fetus #5996 The rearrangement and expression of the human heavy chain locus was demonstrated by the amplification of a segment of DNA including portions of Cmu and VH regions. Primers specific for RNA transcripts including portions of Cmu (Cmu1) and VH (VH3-30) were used to determine if RNA transcripts containing rearranged human Cmu-VDJ sequences were present (FIG. 8).

For this RT-PCR analysis, primers "Cmu1" (5'-caggtg-cagctggtggagtctgg-3', SEQ ID NO: 11) and "VH3-30" (5'caggagaaagtgatggagtc-3', SEQ ID NO: 12) were used to produce a RT-PCR product of 450 base pairs. This RT-PCR was performed by incubating reaction mixtures at 95° for 3 minutes, followed by 40 cycles of incubation at 95° for 30 minutes, 69° for 30 minutes, and 72° for 45 minutes, and one cycle of incubation at 72° for 10 minutes. This RT-PCR product was then reamplified with the same primers by one cycle of incubation at 95° C. for three minute, 40 cycles of incubation at 95° C. for one minute, 59° C. for one minute, 72° C. for one minute, and one cycle of incubation at 72° C. for 10 minutes. As an internal control, RT-PCR amplification of GAPDH was performed as described above.

The gel in FIG. 8 shows that RT-PCR analysis of the spleen from fetus #5996 produced a band (lane 5) matching the amplification products generated using human spleen cDNA (lane 4) or ΔHAC chimeric mouse spleen cDNA (lane 1). No such band was detected in bovine liver (lane 2) or bovine brain (lane 3). As a positive control, amplification of GADPH RNA (lanes 8 and 9) showed the capacity of these tissues to support RT-PCR.

Rearrangement and expression of the human heavy chain region in fetus #5996 was also demonstrated by RT-PCR analysis using primers CH3-F3 (5'-GGAGACCAC-CAAACCCTCCAAA-3', SEQ ID NO: 13) and CH4-R2 (5'-GTGGCAGCAAGTAGACATCG-3', SEQ ID NO: 14). These PCR reaction mixtures contained 18.9 µl water, 3 µl of 10×Ex Taq buffer, 4.8 µl of dNTP mixture, 10 pmol forward primer, 10 pmol of reverse primer, 1 µl of cDNA, and 0.3 µl of Ex Taq. Forty PCR cycles were performed by incubating the reaction mixtures under the following conditions: 85° C. for three minutes, 94° C. for one minute, 98° C. for 10 seconds, 60° C. for 30 seconds, and 72° C. for 30 seconds.

Figure 9:
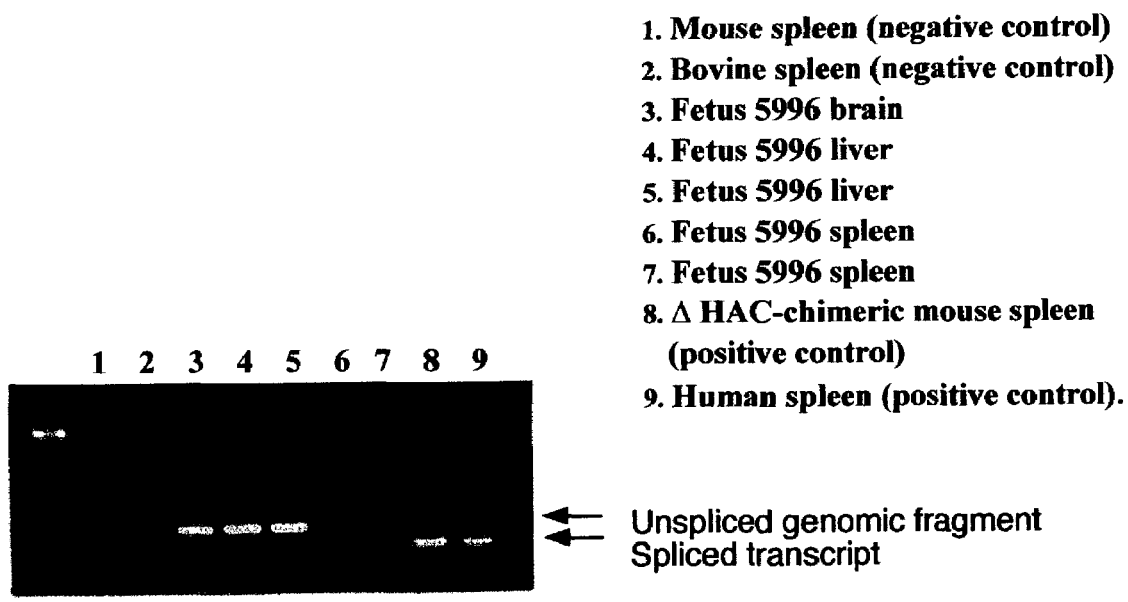
FIG. 9 is a picture of an agarose gel showing the expression of the spliced constant region from the human heavy chain locus in ΔHAC fetus #5996.

As shown in lanes 6 and 7 of FIG. 9, an amplified sequence from the spleen of fetus #5996 was the same size as the spliced constant region fragments from the two positive controls: a sample from a human spleen (lane 8) and a ΔHAC chimeric mouse spleen (lane 9). As expected, the negative controls from a normal mouse spleen and a bovine spleen did not contain an amplified sequence (lanes 1 and 2). Samples from the liver and brain of fetus #5996 did not contain an amplified spliced sequence of the same size as the spliced human mu heavy chain constant region fragments but did contain a amplified sequence of an unspliced genomic fragment derived from genomic DNA contaminating the RNA sample (lanes 3, 4, and 5).

VDJ Rearrangement of the Human Heavy Chain Locus in a ΔHAC Fetus RT-PCR analysis was also performed to further demonstrate VDJ rearrangement in the heavy chain locus in ΔHAC fetus #5996. Nested RT-PCR was performed using primer Cmu-1 (5'-CAGGAGAAAGTGATGGAGTC-3', SEQ ID NO: 15) for the first reaction, primer Cmu-2 (5'-AGGCAGCCAACGGCCACGCT-3', SEQ ID NO: 16) for the second reaction, and primer VH3-30.3 (5'-CAGGT-GCAGCTGGTGGAGTCTGG-3', SEQ ID NO: 17) for both reactions. The RT-PCR reaction mixtures contained 18.9 µl water, 3 µl of 10×Ex Taq buffer, 4.8 µl of dNTP mixture, 10 pmol forward primer, 10 pmol of reverse primer, 1 µl of cDNA, and 0.3 µl of Ex Taq. The RT-PCR was performed using 38 cycles under the following conditions for the first reaction: 85° C. for three minutes, 94° C. for one minute, 98° C. for 10 seconds, 65° C. for 30 seconds, and 72° C. for 30 seconds. For the second reaction, 38 cycles were performed under the following conditions: 85° C. for three minutes, 94° C. for one minute, 98° C. for 10 seconds, 65° C. for 30 seconds, and 72° C. for 30 seconds using primers VH3-30.3 and Cmu-2 (5'-AGGCAGCCAACGGCCACGCT-3', SEQ ID NO: 16).

Figure 10:
FIG. 10 is a picture of an agarose gel showing the expression of rearranged human heavy chain in ΔHAC fetus #5996.

As shown in lanes 6 and 7 of FIG. 10, RT-PCR analysis of the spleen of fetus #5996 produced a heavy chain band of the same size as the positive controls in lanes 8 and 9. Samples from the liver and brain of fetus #5996 contained some contaminating rearranged DNA (lanes 3 and 5). The negative controls in lanes 1 and 2 produced bands of the incorrect size.

Verification of ΔHAC Rearrangement By Sequencing The cDNA obtained by reverse transcription of RNA from the spleen of the ΔHAC fetus #5996 was amplified with primers specific for rearranged human mu and run on an agarose gel. The band produced by amplification with the Cmu1-VH3-30 primer pair was excised from the gel. The amplified cDNA was recovered from the band and cloned. DNA from a resulting clone that was PCR-positive for rearranged human mu was purified and sequenced (FIG. 11A).

The sequence from this ΔHAC fetus is greater than 95% homologous to over 20 known human heavy chain sequences. For example, the mu chain of a human anti-pneumococcal antibody is 97% homologous to a region of this sequence (FIG. 11B).

Additional sequences from rearranged human heavy chains were also obtained by RT-PCR analysis of the spleen of fetus #5996 using primers Cmu-1 and VH3-30.3, followed by reamplification using primers Cmu-2 and VH3-30.3. The RT-PCR products were purified using CHROMA SPIN column (CLONETECH) and cloned into the pCR2.1 TA-cloning vector (Invitrogen) according to manufacturer's protocol. The Dye Terminator sequence reaction (ABI Applied System) was performed in a 10 µl volume reaction mixture composed of BigDye Terminator reaction mixture (3 µl), template plasmid (200 ng), and the Cmu-2 primer (1.6 pmol). The sequencing reaction was performed using a ABI 3700 sequencer. For this analysis, twenty-five cycles were conducted under the following conditions: 96° C. for one minute, 96° C. for 10 seconds, 55° C. for five seconds, and 60° C. for four minutes.

At least two rearranged human heavy chain transcripts were identified, which were VH3-11/D7-27/JH3/Cµ and VH3-33/D6-19/JH2/Cµ (FIGS. 12A and 12B). The results demonstrate that VDJ rearrangement of the human mu heavy chain locus occurs in the ΔHAC in the spleen of fetus #5996. The identification of more than one rearranged heavy chain sequence from the same fetus also demonstrates the ability of ΔHAC fetuses to generate diverse human immunoglobulin sequences.

Rearrangement and Expression of Human Heavy and Light Chain Loci in ΔΔHAC Fetus

Cloned fetuses derived from bovine fetal fibroblasts tranchromosomal for the ΔΔHAC were removed from recipient cows at various gestational days. The fetuses were analyzed for the presence and rearrangement of the HAC-borne human immunoglobulin heavy and lambda light chain loci. Studies of genomic DNA from these tissues indicated the presence of the human immunoglobulin heavy and light chains in some of the fetuses. Examination of cDNA derived from the spleens of these fetuses indicated rearrangement and expression of the immunoglobulin heavy and light chain loci in some of these fetuses. FACS analysis also demonstrated the expression of human lambda light chain protein on the surface of splenic lymphocytes in two of the fetuses.

Presence of Human Heavy and Light Chain Loci in ΔΔHAC Fetuses To determine whether ΔΔHAC fetuses retained the human heavy and light chain loci, PCR analysis was performed on genomic DNA from the liver of 58 day fetus #5580, 57 day fetus # 5848, and 91 day fetuses #5442A and 5442B. The PCR primers used for detection of the heavy chain loci were VH3-F (5'-AGTGAGATAAGCAGTG-GATG-3', SEQ ID NO: 18) and VH3-R (5'-CTTGTGC-TACTCCCATCACT-3', SEQ ID NO: 19), and the primers used for the detection of the light chain were IgL-F (5'-GGAGACCACCAAACCCTCCAAA-3', SEQ ID NO: 20) and IgL-R (5'-GAGAGTTGCAGAAGGGGTYGACT-3', SEQ ID NO: 21). The PCR reaction mixtures contained 18.9 µl water, 3 ul of 10×Ex Taq buffer, 4.8 µl of dNTP mixture, 10 pmol forward primer, 10 pmol of reverse primer, 1 µl of genomic DNA, and 0.3 ul of Ex Taq. Thirty-eight PCR cycles were performed as follows: 85° C. for three minutes, 94° C. for one minute, 98° C. for 10 seconds, 56° C. for 30 seconds, and 72° C. for 30 seconds (FIGS. 13 and 14).

Figure 13:
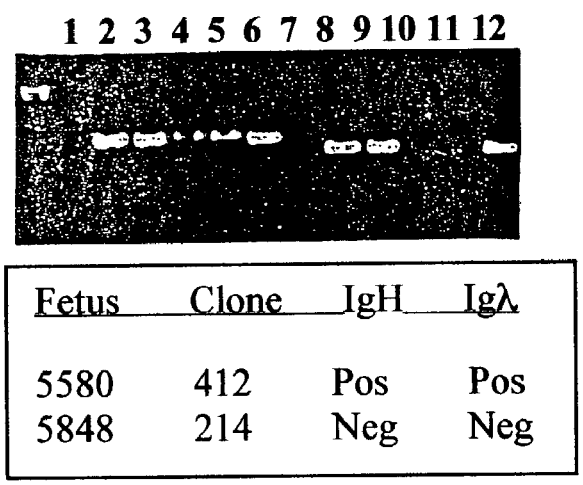
FIG. 13 is a picture of an agarose gel demonstrating that ΔΔHAC fetus #5580 contains both human heavy and light chain immunoglobulin loci.
Figure 14:
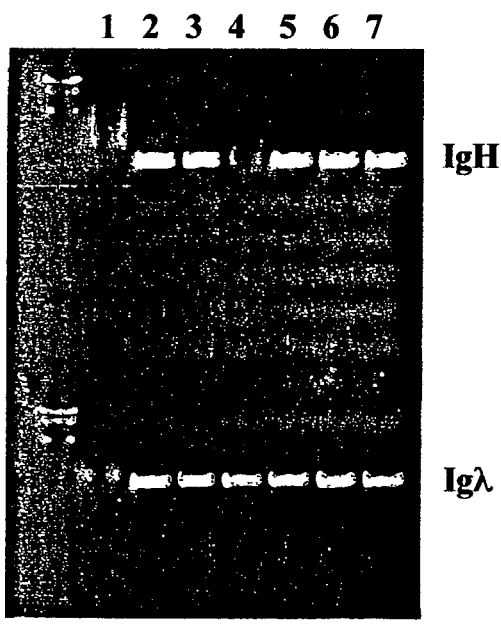
FIG. 14 is a picture of an agarose gel demonstrating that ΔΔHAC fetuses #5442A, and 5442B contain both human heavy and light chain loci.

As illustrated in FIGS. 13 and 14, positive control 58 day fetus #5580 contained both human heavy and light chain immunoglobulin loci. Additionally, the 91 day fetuses #5442A and 5442B also contained both heavy and light chain loci (FIG. 14). In contrast, fetus #5848 did not contain either human loci and may not have contained ΔΔHAC. These results suggested that ΔΔHAC can be stably retained up to gestational day 91 in bovine.

Rearrangement and Expression of Human Heavy Chain Locus in ΔΔHAC Fetus #5442A RT-PCR was used to detect expression of rearranged human heavy chain RNA transcripts in ΔΔHAC fetus #5542A. The RT-PCR primers used were CH3-F3 (5'-GGAGACCACCAAACCCTCCAAA-3', SEQ ID NO: 22) and CH4-R2 (5'-GAGAGTTGCA-GAAGGGGTGACT-3', SEQ ID NO: 23). The RT-PCR reaction mixtures contained 18.9 µl water, 3 µl of 10×Ex Taq buffer, 4.8 µl of dNTP mixture, 10 pmol forward primer, 10 pmol of reverse primer, 1 µl of cDNA, and 0.3 µl of Ex Taq. Forty cycles of RT-PCR cycles were performed as follows: 85° C. for three minutes, 94° C. for one minute, 98° C. for 10 seconds, 60° C. for 30 seconds, and 72° C. for 30 seconds.

Figure 15:
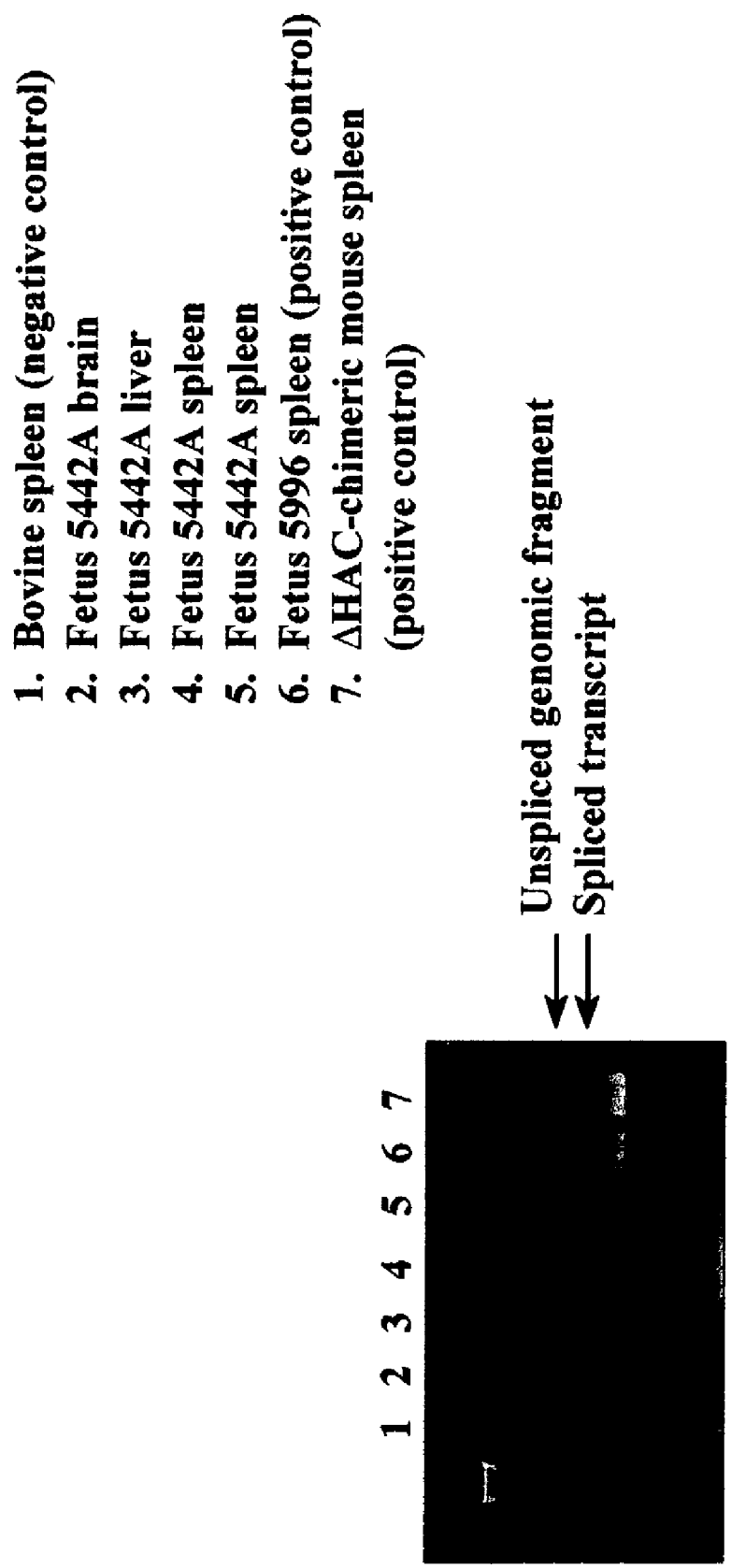
FIG. 15 is a picture of an agarose gel showing the expression of the spliced mu constant region from the human heavy chain locus in ΔΔHAC fetus #5442A.

Lanes 4 and 5 of FIG. 15 contained amplified spliced mu heavy chain constant region sequences from the spleen of fetus #5442A that are similar in size to that of the positive control samples. These results indicate that fetus #5442A expressed a rearranged mu heavy chain transcript in its spleen. Faint bands were also seen in the region of the unspliced genomic sequence, which are amplified from genomic DNA contaminated in the RNA sample. Control samples from the liver and brain of fetus #5442A did not produce a band of the size expected for an amplified rearranged heavy chain sequence.

Rearrangement and Expression of Human Heavy Chain Locus in ΔΔHAC Fetus #5868A RT-PCR was used to detect expression of rearranged human heavy chain RNA transcripts in the spleen of a ΔΔHAC fetus at 119 gestational days (fetus #5868A). The primers used for this analysis were VH30-3 (5'-caggtgcagctggtggagtctgg-3', SEQ ID NO: 24) and CM-1 (5'-caggagaaagtgatggagtc-3', SEQ ID NO: 25). Additionally, primers "GAPDH up" (5'-gtcatcatctctgcccct-tctg-3', SEQ ID NO: 26) and "GAPDH down" (5'-aacaact-tcttgatgtcatcat-3', SEQ ID NO: 27) were used to amplify GAPDH control transcripts. For this PCR analysis, the reaction mixture was incubated at 95° C. for five minutes and then multiple cycles of denaturation, annealing, and amplification were performed by incubation at 95° C. for one minute, 58° C. for one minute, and 72° C. for two minutes. Then, the mixture was incubated at 72° C. for 10 minutes.

Figure 16:
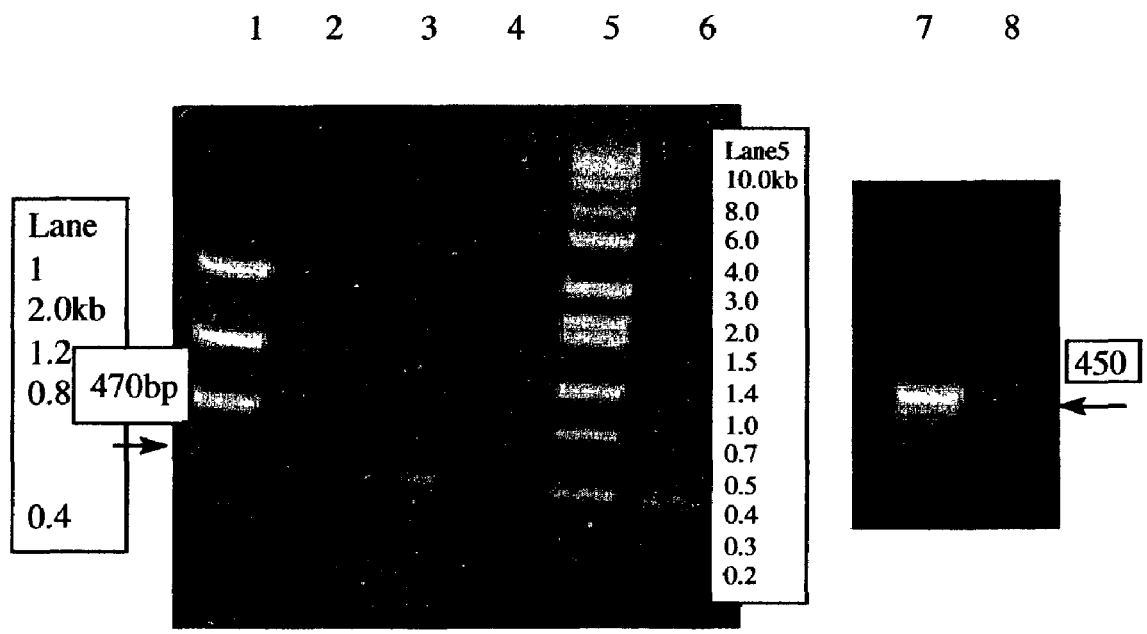
FIG. 16 is a picture of an agarose gel showing the rearrangement and expression of the human heavy chain locus in ΔΔHAC fetus #5868A.

Lane 3 of FIG. 16 contains the RT-PCR product produced from this analysis of ΔΔHAC fetus# 5868A. This RT-PCR product was the size expected for the amplification of a rearranged human heavy chain (470 base pairs) and migrated to the same position in the gel as the control cDNA known to contain sequences corresponding to rearranged human heavy chain transcripts. As controls, both ΔΔHAC fetus# 5868A fetal spleen cDNA and normal bovine cDNA samples generated a product when amplified with GAPDH primers, demonstrating the capacity of the cDNA to support amplification (lanes 7 and 8).

Rearrangement and Expression of Human Lambda Locus in ΔΔHAC Fetuses #5442A and 5442B Primers specific for amplification of a transcript including portions of human lambda were used to detect RNA transcripts from a rearranged human lambda light chain locus.

Figure 17:
FIG. 17 is a picture of an agarose gel showing rearrangement and expression of the human Ig lambda locus in ΔΔHAC fetuses #5442A and 5442B.

For the RT-PCR analysis shown in FIG. 17, an equimolar mixture of primers Cλ1 (.5'-GGGAATTCGGGTAGAAGT-TCACTGATCAG-3', SEQ ID NO: 28), Cλ2-3 (5'-GG-GAATTCGGGTAGAAGTCACTTATGAG-3', SEQ ID NO: 29), and Cλ7 (5'-GGGAATTCGGGTAGAAGTCACTTAC-GAG-3', SEQ ID NO: 30) was used with primer Vλ1 LEA1 (5'-CCCCCAAGCTTRCCKGSTYYCCTCTCCTC-3', SEQ ID NO: 31). The RT-PCR reaction mixtures contained 18.9 µl water, 3 µl of 10×Ex Taq buffer, 4.8 µl of dNTP mixture, 10 pmol forward primer, 10 pmol of reverse primer, 1 µl of cDNA and 0.3 µl of Ex Taq. The RT-PCR conditions were as follows: 40 cycles of 85° C. for three minutes, 94° C. for one minute, 98° C. for 10 seconds, 60° C. for 30 seconds, and 72° C. for one minute.

Figure 18:
FIG. 18 is a picture of an agarose gel showing rearrangement and expression of the human Ig lambda locus in ΔΔHAC fetus #5442A.

As shown in FIG. 18, this RT-PCR analysis was also performed using an equimolar mixture of primers Vλ3LEA1 (5'-CCCCCAAGCTTGCCTGGACCCCTCTCTGG-3'; SEQ ID NO:32), Vλ3JLEAD (5'-ATCGGCAAAGCTTG-GACCCCTCTCTGGCTCAC-3', SEQ ID NO: 33), VλBACK4 (5'-CCCCCAAGCTTCTCGGCGTCCTTGCT-TAC-3', SEQ ID NO: 34) and an equimolar mixture of primers Cλ1 (5'-GGGAATTCGGGTAGAAGTTCACT-GATCAG-3', SEQ ID NO: 35) Cλ2-3 (5'-GGGAAT-TCGGGTAGAAGTCACTTATGAG-3', SEQ ID NO: 36) and Cλ7 (5'-GGGAATTCGGGTAGAAGTCACTTAC-GAG-3', SEQ ID NO: 37). The RT-PCR reaction conditions were the same as those described above for FIG. 7.

Lanes 6 and 7 of FIG. 17 and lanes 4 and 5 of FIG. 18 contained RT-PCR products from the spleen of fetus #5442A that are similar in size to the positive control bands, indicating the presence of rearranged light chain RNA transcripts in this fetus. The spleen sample from fetus #5442B produced very weak bands of the appropriate size which are not visible in the picture. This RT-PCR product indicates that fetus #5442B also expressed a rearranged light chain immunoglobulin transcript in its spleen. As expected, samples from the brain of fetuses #5442A and 5442B did not express human rearranged lambda light chain transcripts.

Rearrangement and Expression of Human Lambda Locus in ΔΔHAC Fetus #5868A RNA transcripts from a rearranged human lambda light chain locus were also detected in ΔΔHAC fetus# 5868A. For this analysis, primers specific for amplification of a transcript including portions of human lambda were used to detect ΔΔHAC-encoded expression of transcripts encoding portions of a rearranged human lambda locus. Primer VL1 LEAI (5'-cccccaagcttRccKgStYYcctctc-ctc-3'; SEQ ID NO:38) and an equimolar mixture of primers CL1 (5'-gggaattcgggtagaagtcactgatcag-3'; SEQ ID NO:39), CL2-3 (5'-gggaattcgggtagaagtcacttatgag-3'; SEQ ID NO:40), and CL7 (5'-gggaattcgggtagaagtcacttacgag-3'; SEQ ID NO:41) were used for this analysis. For this RT-PCR reaction, the reaction mixtures were incubated at 95° C. for 5 minutes and then multiple cycles of denaturation, annealing, and amplification were performed by incubation at 95° C. for one minute, 60° C. for one minute, and 72° C. for two minutes. Then, the mixtures were incubated at 72° C. for 10 minutes.

Figure 19:
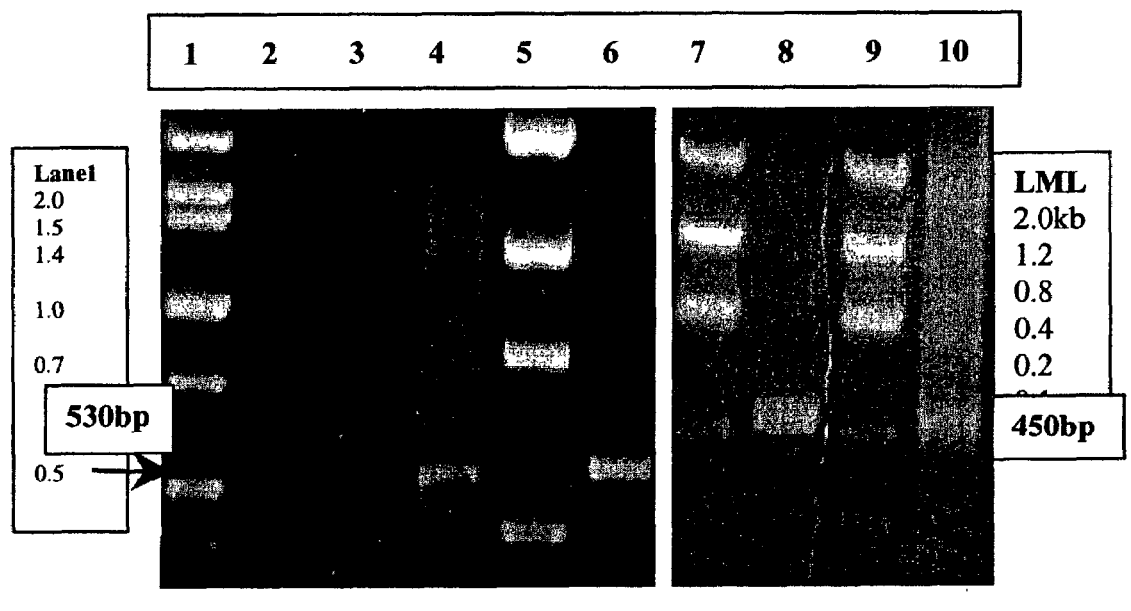
FIG. 19 is a picture of an agarose gel showing rearrangement and expression of the human Ig lambda locus in ΔΔHAC fetus #5868A.

This analysis demonstrated that spleen cDNA from ΔΔHAC #5868A (lane 4 of FIG. 19) produced a RT-PCR product of the same size as the TC mouse spleen cDNA (lane 6) positive control. No such RT-PCR product was detected using either brain or liver cDNA from ΔΔHAC #5868A (lanes 2 and 3, respectively). The capacity of each of these tissues to support RT-PCR was shown by successful amplification of the housekeeping gene, GAPDH using primers "GAPDH up" and "GAPDH down" (lanes 8 and 10).

Verification of ΔΔHAC Rearrangement by Sequencing RT-PCR analysis was performed on a spleen sample from fetus #5442A using an equimolar mixture of primers Cλ1, Cλ2-3, and Cλ7 with primer Vλ1LEA1, or an equimolar mixture of primersVλ3LEA1, Vλ3JLEAD, and VλBACK4 and an equimolar mixture of primers Cλ1, C/2-3, and Cλ7 in. The PCR products were purified using a CHROMA SPIN column (CLONETECH) and cloned into the pCR2.1 TA-cloning vector (Invitrogen), according to manufacturer's protocol. The Dye Terminator sequence reaction (ABI Applied System) was carried out using the Cλ1, Cλ2-3, and Cλ7 primers in an equimolar mixture. Twenty-five cycles were performed at 96° C. for one minute, 96° C. for 10 seconds, 55° C. for five seconds, and 60° C. for four minutes. The 10 µl reaction mixture contained BigDye Terminator reaction mixture (3 µl), template plasmid (200 ng), and the Cλ1, Cλ2-3, and Cλ7 primers (1.6 pmol). The reaction mixture was analyzed using a ABI 3700 sequencer.

At least two rearranged human lambda light chain transcripts were identified (V1-17/JL3/Cλ and V2-13/JL2/Cλ). These results demonstrate that VJ rearrangement of human lambda light chain genes occurs in the ΔΔHAC in the spleen of fetus #5442A (FIGS. 20 and 21).

Figure 22D:
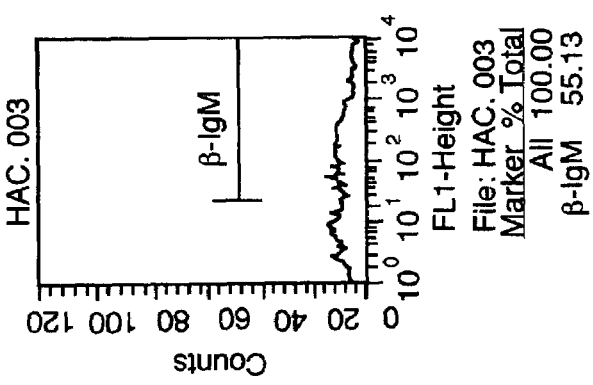
Figure 22C:
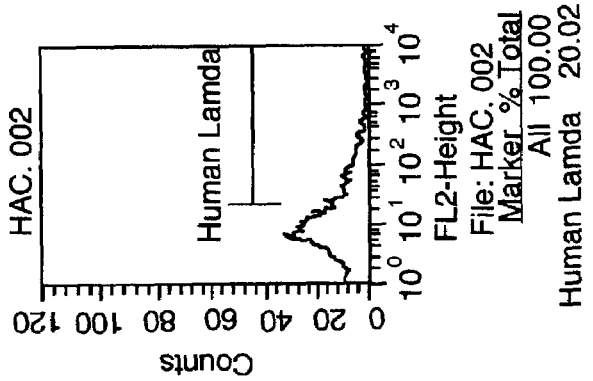
Figure 22B:
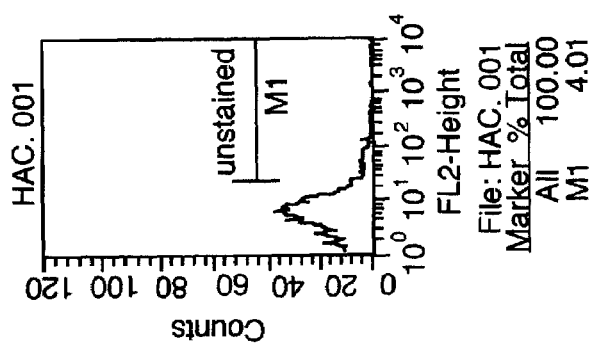
Figure 22A:
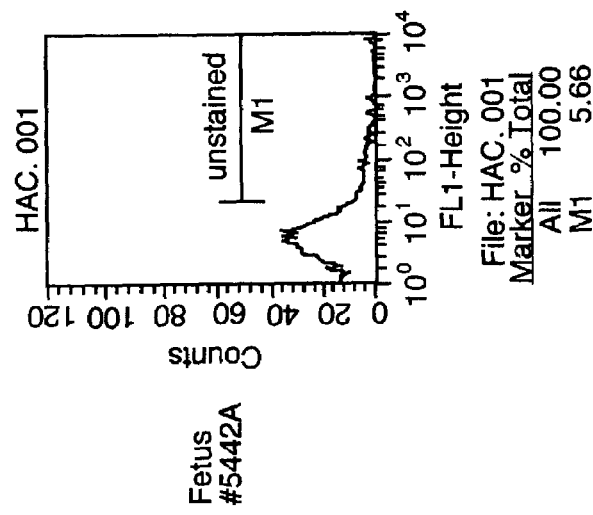

FACS Analysis of Expression of Human Lambda Light Chain and Bovine Heavy Chain in ΔΔHAC Fetus #5442A and 5442B Splenic lymphocytes from ΔΔHAC Fetus #5442A and 5442B were analyzed for the expression of human lambda light chain and bovine heavy chain proteins. These cells were reacted with a phycoerytherin labeled anti-human lambda antibody (FIGS. 22C and 22D), a FITC labeled anti-bovine IgM antibody (FIGS. 22D and 22H), or no antibody (FIGS. 22A, 22B, 22E, and 22F) for 20 minutes at 4° C. Cells were then washed twice with PBS plus 2% FCS and analyzed on a FASCalibur cell sorter. The percent of cells reacting with the antibody was calculated using the non antibody controls to electronically se the gates. These percentages are displayed beneath each histogram. Fetus # 5442A (FIGS. 22A–22D) and fetus #5442B (FIGS. 22E–22H) expressed both human lambda light chain protein and bovine heavy chain protein.

EXAMPLE 3

Transgenic Ungulates Producing Xenogenous Antibodies and Reduced Amounts of Endogenous Antibodies Transgenic ungulates expressing a xenogenous antibody and having a reduced level of expression of endogenous antibodies may also be generated. By increasing the number of functional xenogenous immunoglobulin heavy or light chain genes relative to the number of functional endogenous heavy or light chain genes, the percentage of B cells expressing xenogenous antibodies should increase.

To generate these transgenic ungulates, ΔHAC or ΔΔHAC transgenic ungulates may be mated with transgenic ungulates containing a mutation in one or both alleles of an endogenous immunoglobulin chain (e.g., a mu heavy chain or a lambda or kappa light chain). If desired, the resulting transgenic ungulates may be mated with (i) transgenic ungulates containing a mutation in one or both alleles of an endogenous alpha-(1,3)-galactosyltransferase, prion, and/or J chain nucleic acid or (ii) transgenic ungulates containing an exogenous J chain nucleic acid (e.g., human J chain). Alternatively, a cell (e.g., a fetal fibroblast) from a ΔHAC or ΔΔHAC transgenic fetus may be genetically modified by the mutation of one or more endogenous immunoglobulin genes. In another possible method, ΔHAC or ΔΔHAC is introduced into a cell (e.g., a fetal fibroblast) in which endogenous immunoglobulins (mu heavy and/or lambda light chains) are hemizgously or homozygously inactivated. In any of the above methods, the cells may also be genetically modified by (i) the introduction of a mutation, preferably a knockout mutation, into one or both alleles of an endogenous alpha-(1,3)-galactosyltransferase, prion, and/or J chain nucleic acid or (ii) the introduction of an exogenous J chain nucleic acid. The resulting transgenic cell may then be used in nuclear transfer procedures to generate the desired transgenic ungulates. Exemplary methods are described below.

Figure 3F:
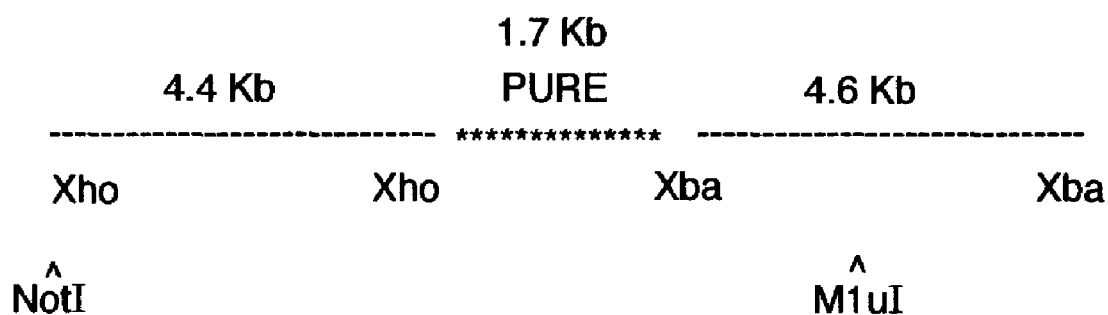
Figure 4:
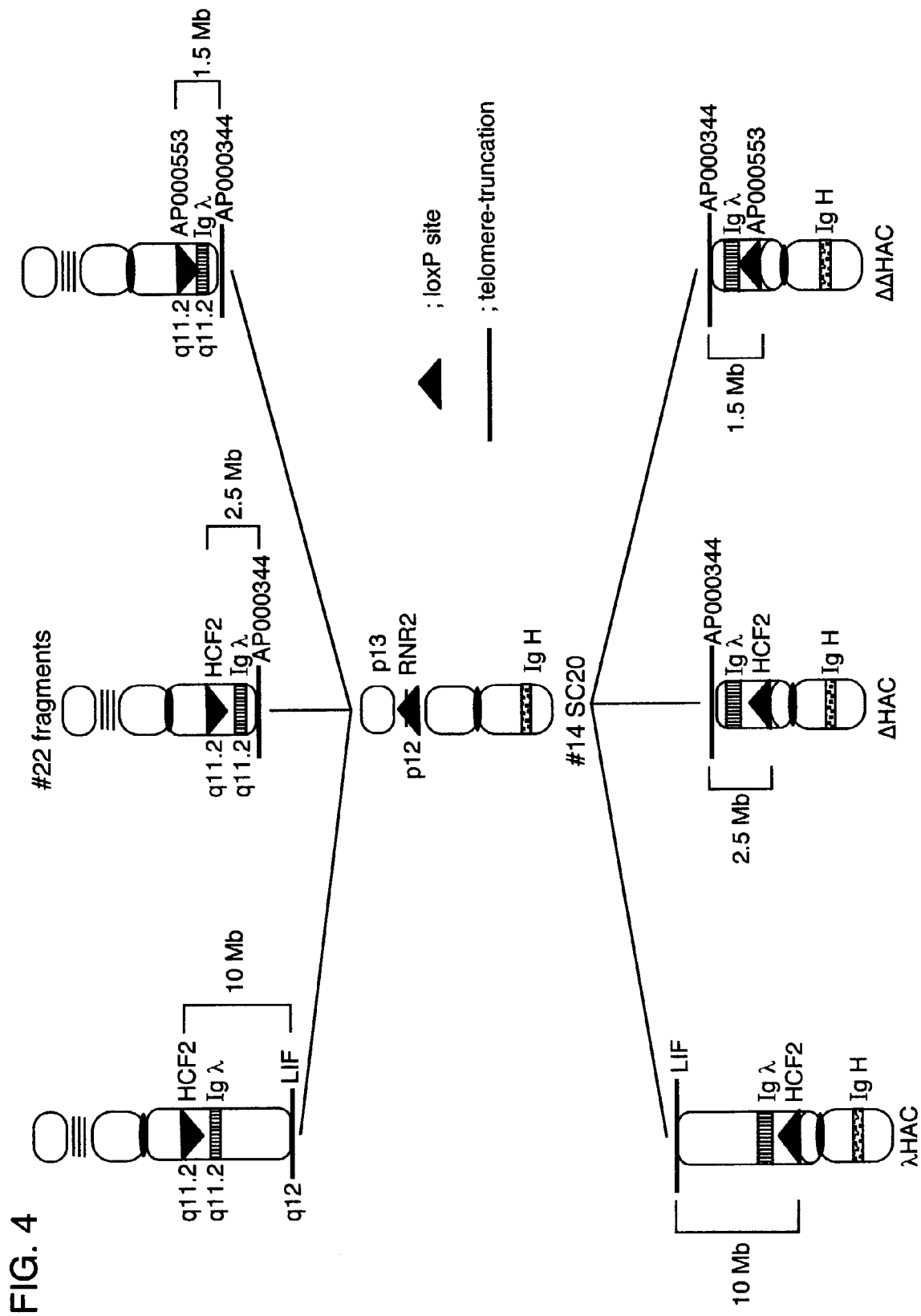
FIG. 4 is a schematic illustration of the construction of ΔHAC and ΔΔHAC.

DNA Constructs The mu heavy chain (FIG. 2A), lambda light chain, kappa light chain, alpha-(1,3)-galactosyltransferase, prion, and/or J chain knockout constructs described above may be used. Alternatively, the puromycin resistant mu heavy chain construct described below may be used (FIG. 3F). This knockout construct was designed to remove the 4 main coding exons of the bovine mu heavy chain locus but leave the transmembrane domain intact, resulting in the inactivation of the mu heavy chain locus.

The puromycin resistant construct was assembled as follows. A 4.4 kilobase XhoI fragment containing the region immediately proximal to coding exon 1 was inserted into the XhoI site of pBluescript II SK+. Plasmid pPGKPuro, which contains a puromycin resistant gene, was obtained from Dr. Peter W. Laird, Whitehead Institute, USA. A 1.7 Kb XhoI fragment containing a puromycin resistance gene was subcloned adjacent to, and downstream of, the 4.4 Kb fragment into the SalI site present in the polylinker region. This 1.7 Kb puromycin marker replaces the coding exons CH1, CH2, CH3 and CH4 of the bovine immunoglobulin heavy chain locus. An XbaI fragment containing a 4.6 Kb region of the mu locus that is downstream of these four exons in the wild-type genomic sequence was added to this construct for use as the second region of homology.

To generate the final targeting construct, a subclone of this construct was generated by cutting the three assembled fragments with NotI and MluI The MluI restriction digestion truncates the 4.6 Kb fragment down to 1.4 Kb. The NotI site lies in the polylinker and does not cut into the subcloned DNA itself. The MluI site was filled in with a Klenow fragment to generate a blunt end, and the NotI/filled in MluI fragment was subcloned into a fresh pBluescript II SK+ vector using the NotI and SmaI sites present in the pBluescript vector. For gene targeting, the final vector is linearized with NotI.

Gene Targeting by Electroporation and Drug Selection of Transfected Fibroblasts For electroporation, a single cell suspension of $1 \times 10^7$ bovine fetal fibroblasts (e.g., fibroblasts obtained as described in Example 2 from a ΔHAC or ΔΔHAC transgenic fetus) that had undergone a limited number of population doublings is centrifuged at 1200 rpm for five minutes and re-suspended in 0.8 ml of serum-free Alpha-MEM medium. The re-suspended cells are transferred to a 0.4 cm electroporation cuvette (Invitrogen, cat#. P460-50). Next, 30 µg of a restriction enzyme-linearized, gene targeting vector DNA is added, and the contents of the cuvette are mixed using a 1 ml pipette, followed by a two minute incubation step at room temperature. The cuvette is inserted into the shocking chamber of a Gene Pulser II electroporation system (Biorad) and then electroporated at 1000 volts and 50 µF. The cuvette is quickly transferred to a tissue culture hood and the electroporated cells are pipetted into approximately 30 ml of complete fibroblast medium. The cells are equally distributed into thirty 100 mm tissue culture dishes (Corning, cat#. 431079), gently swirled to evenly distribute the cells, and incubated at 38.5° C./5% $CO_2$ for 16 to 24 hours The media is removed by aspiration and replaced with complete fibroblast medium containing the selection drug of choice. The media is changed every two days and continued for a total time period of 7 to 14 days. During the drug selection process, representative plates are visually monitored to check for cell death and colony formation. Negative control plates are set up that contained fibroblasts that are electroporated in the absence of the gene targeting vector and should yield no colonies during the drug selection process.

Picking of Drug Resistant Fibroblast Colonies and Expansion of Cells Following completion of the drug selection step (usually 7 to 14 days), the drug resistant colonies are macroscopically visible and ready for transfer to 48 well tissue culture plates for expansion. To assist in the transferring process, individual colonies are circled on the bottom of the tissue culture plate using a colored marker (Sharpie). Tissue culture plates containing colonies are washed 2× with 1×D-PBS (without $Ca^{2+}$ and $Mg^{2+}$) and then 5 ml of a 1:5 dilution of the cell dissociation buffer is added per plates. Following a 3 to five minute room temperature incubation step, individual colonies start to detach from the bottom of the tissue culture dish. Before the colonies detached, they are individually transferred to a single well of a 48 well tissue culture plate using a P200 pipetmen and an aerosol barrier pipette tip (200 or 250 μl). Following transfer, the colony is completely dissociated by pipeting up-and-down and 1 ml of complete fibroblast medium is added. To ensure that the cells are drug resistant, drug selection is continued throughout the 48 well stage. The transferred colonies are cultured at 38.5° C./5% $CO_2$ and visually monitored using an inverted microscope. Two to seven days later, wells that are approaching confluency are washed two times with 1×D-PBS (without $Ca^{2+}$ and $Mg^{2+}$) and detached from the bottom of the well by the addition of 0.2 ml of cell dissociation buffer, followed by a five minutes room temperature incubation step. Following detachment, the cells are further dissociated by pipeting up-and-down using a P1000 pipetmen and an aerosol pipette tip (1000 μl). Approximately 75% of the dissociated fibroblasts are transferred to an individual well of a 24 well tissue culture plate to expand further for subsequent PCR analysis and the remaining 25% is transferred to a single well of a second 24 well plate for expansion and eventually used for somatic cell nuclear transfer experiments. When cells in the plate containing 75% of the original cells expanded to near confluency, DNA is isolated from that clone for genetic analysis.

DNA Preparation The procedure used to isolate DNA for genetic analyses is adapted from Laird et al, Nucleic Acids Research, 1991, Volume 19, No. 15. In particular, once a particular clone has attained near-confluency in one well of a 24 well plate, culture medium is aspirated from that well and the adherent cells are washed twice with PBS. The PBS is aspirated off and replaced with 0.2 ml buffer to lyse the cells and digest excess protein from the DNA to be isolated. This buffer is composed of 100 mM Tris-HCl (pH 8.5), 5 mM EDTA, 0.2% SDS, 200 mM NaCl and 100 ug/ml proteinase K. The 24 well plate is returned to the tissue culture incubator for a minimum of three hours to allow the release of the DNA and digestion of protein. The viscous product of this procedure is transferred to a 1.5 ml microcentrifuge tube and 0.2 ml of isopropanol added to precipitate the DNA. The precipitate is recovered by centrifugation, the DNA pellet is rinsed with 70% ethanol, and after air-drying, the pellet is resuspended in 25–50 ul of buffer containing 10 mM Tris, pH 8, and 1 mM EDTA. This DNA is used for PCR analyses of clones.

Screening of Clones Two different approaches are used to screen clones, both employing the polymerase chain reaction (PCR). All approaches described in this section are adaptable to the targeting of any other gene, the only difference being the sequences of the primers used for genetic analysis.

According to the first approach, two separate pairs of primers are used to independently amplify products of stable transfection. One pair of primers is used to detect the presence of the targeting vector in the genome of a clone, regardless of the site of integration. The primers are designed to anneal to DNA sequences both present in the targeting vector. The intensity of the PCR product from this PCR reaction may be correlated with the number of copies of the targeting vector that have integrated into the genome. Thus, cells containing only one copy of the targeting vector tend to result in less intense bands from the PCR reaction. The other pair of primers is designed to detect only those copies of the vector that integrated at the desired locus. In this case, one primer is designed to anneal within the targeting vector and the other is designed to anneal to sequences specific to the locus being targeted, which are not present in the targeting vector. In this case, a PCR product is only detected if the targeting vector has integrated directly next to the site not present in the targeting vector, indicating a desired targeting event. If product is detected, the clone is used for nuclear transfer.

For the neomycin resistant heavy chain knockout construct, primers Neol (5'-CTT GAA GAC GAA AGG GCC TCG TGA TAC GCC-3', SEQ ID NO: 42) and IN2521 (5'-CTG AGA CTT CCT TTC ACC CTC CAG GCA CCG-3', SEQ ID NO: 43) are used to detect the presence of the targeting vector in cells, regardless of the location of integration. Primers Neol and OUT3570 (5'-CGA TGA ATG CCC CAT TTC ACC CAA GTC TGT C-3', SEQ ID NO: 44) are used to specifically amplify only those copies of the targeting construct that integrated into the mu heavy chain locus.

For these PCR reactions to analyze the integration of the neomycin resistant heavy chain knockout construct, a Qiagen PCR kit is used. The PCR reaction mixture contains 1 pmole of each primer, 5 ul of 10× reaction buffer, 10 ul of Q solution, 5 ul of DNA, and 1 ul of dNTP solution. The reaction mixture is brought to a total volume of 50 ul with $H_2O$. This PCR amplification is performed using an initial denaturing incubation at 94° C. for two minutes. Then, 30 cycles of denaturation, annealing, and amplification are performed by incubation at 94° C. for 45 seconds, 60° C. for 45 seconds, and 72° C. for two minutes. Then, the reaction mixture is incubated at 72° C. for five minutes and at 4° C. until the mixture is removed from the PCR machine.

In the alternative approach, a single primer set is used to amplify the targeted locus and the size of the PCR products is diagnostic for correct targeting. One primer is designed to anneal to a region of the locus not present in the targeting vector and the other primer is designed to anneal to a site present in the targeting vector but also present in the wild type locus. In this case, there is no detection of targeting vector that had integrated at undesirable sites in the genome. Because the region deleted by the targeting vector is different in size from the drug selection marker inserted in its place, the size of the product depended on whether the locus amplified is of wild-type genotype or of targeted genotype. Amplification of DNA from clones containing incorrect insertions or no insertions at all of the targeting vector results in a single PCR product of expected size for the wild type locus. Amplification of DNA from clones containing a correctly targeted ("knocked out") allele results in two PCR products, one representing amplification of the wild type allele and one of altered, predictable size due to the replacement of some sequence in the wild-type allele with the drug resistance marker, which is of different length from the sequence it replaced.

For the puromycin resistant heavy chain knockout construct, primers Shortend (5'-CTG AGC CAA GCA GTG GCC CCG AG-3', SEQ ID NO: 45) and Longend (5'-GGG CTG AGA CTG GGT GAA CAG AAG GG-3', SEQ ID NO: 46) are used. This pair of primers amplifies both the wild-type heavy chain locus and loci that have been appropriately targeted by the puromycin construct. The size difference between the two bands is approximately 0.7 Kb. The presence of the shorter band is indicative of appropriate targeting.

For this PCR reaction to analyze the integration of the puromcying resistant heavy chain knockout construct, a Promega Master Mix kit is used. The PCR reaction mixture contains 1 pmole of each primer, 2.5 ul of DNA, and 25 ul of 2× Promega Master Mix. The reaction mixture is brought to a total volume of 50 ul with $H_2O$. This PCR amplification is performed using an initial denaturing incubation at 94° C. for two minutes. Then, 30 cycles of denaturation, annealing, and amplification are performed by incubation at 94° C. for 45 seconds, 60° C. for 45 seconds, and 72° C. for two minutes. Then, the reaction mixture is incubated at 72° C. for five minutes and at 4° C. until the mixture is removed from the PCR machine.

First Round of Nuclear Transfer Selected fibroblast cells in which an immunoglobulin gene has been inactivated may be used for nuclear transfer as described in Example 2 to generate a transgenic ungulate containing a mutation in an endogenous immunoglobulin gene and containing a HAC encoding an xenogenous immunoglobulin gene. Alternatively, nuclear transfer may be performed using standard methods to insert a nucleus or chromatin mass (i.e., one or more chromosomes not enclosed by a membrane) from a selected transgenic fibroblast into an enucleated oocyte (U.S. Ser. No. 60/258,151; filed Dec. 22, 2000). These methods may also be used for cells in which an endogenous alpha-(1,3)-galactosyltransferase, prion, and/or J chain nucleic acid has been mutated.

Second Round of Mutagenesis and Nuclear Transfer If desired, a cell (e.g., a fetal fibroblast) may be obtained from a transgenic ungulate generated from the first round of nuclear transfer. Another round of gene targeting may be performed as described above to inactivate the second allele of the gene inactivated in the first round of targeting. Alternatively, another immunoglobulin (e.g., mu heavy chain, lambda light chain, kappa light chain, or J chain), alpha-(1,3)-galactosyltransferase, or prion gene may be inactivated in this round of targeting. For this second round of targeting, either a higher concentration of antibiotic may be used or a knockout construct with a different antibiotic resistance marker may be used. Antibiotic resistance cells may be selected as described above. The selected cells may be used in a second round of nuclear transfer as described above to generate, for example, a transgenic ungulate containing two mutations in endogenous immunoglobulin genes and containing a HAC encoding an xenogenous immuno-globulin gene. Alternatively, the selected antibiotic resistant cells may first be treated to isolate G1 phase cells as described below, which are used for the second round of nuclear transfer.

To isolation of G1 cells for nuclear transfer, $5.0 \times 10^5$ cells are plated onto 100 mm tissue culture plates containing 10 ml of α-MEM+FCS, twenty four hours prior to isolation. The following day, plates are washed with PBS and the culture medium is replaced for 1–2 hours before isolation. The plates are then shaken for 30–60 seconds on a Vortex-Genie 2 (Fisher Scientific, Houston, Tex., medium speed), the medium is removed, spun at 1000 G for five minutes and the pellet is re-suspended in 250 μl of MEM +FCS. Newly divided cell doublets attached by a cytoplasmic bridge, are then selected, as these cells are in early G1. This isolation procedure is referred to as the "shake off" method.

EXAMPLE 4

Transgenic Ungulates Having Reduced α-1,3-galactosyltransferase Activity

Bovine fibroblast cell lines in which one allele of the α-1,3-galactosyltransferase locus is mutated were generated by homologous recombination. The DNA construct for generating the α-galactosyltransferase knockout cells was used to prevent transcription of functional, full-length α-galactosyltransferase mRNA by inserting both a puromycin-resistance gene (puro, described in Example 3) and a transcription termination cassette (STOP) in exon 9 which contains the catalytic domain. Thus, the resulting immature α-galactosyltransferase transcripts lack the catalytic domain. The DNA construct (i.e., the α-galactosyltransferase KO vector) was electroporated into three independent bovine fibroblast cell lines, and then puromycin-resistant colonies were isolated. Based on PCR analysis, homologous recombination in the exon 9 region occurred in some colonies. Thus, bovine fibroblast cell lines in which one allele of α1,3-galactosyltransferase locus is mutated were generated. If desired, the second allele can be mutated by using the same knockout vector and a higher concentration of antibiotic to select for homozygous knockout cells or using another knockout vector with a different antibiotic resistance gene. This method may also be applied to cells from other ungulates to generate transgenic cells for use in the nuclear transfer methods described herein to produce transgenic ungulates of the present invention.

These methods are described further below.

Figure 23:
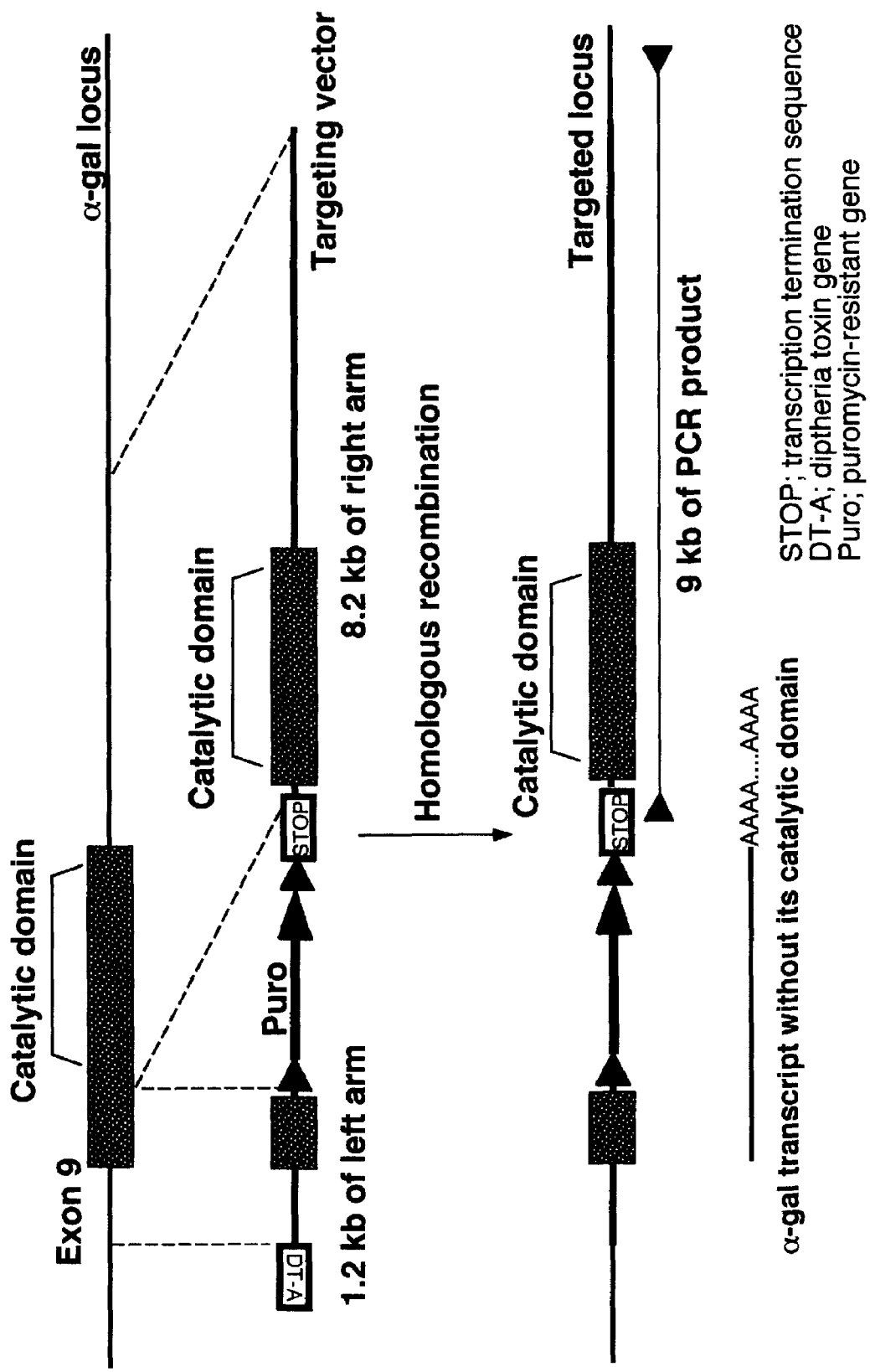
FIG. 23 is a schematic illustration of the α-(1,3)-galactosyltransferase knockout vector used to insert a puromycin resistance gene and a transcription termination sequence into the endogenous α-(1,3)-galactosyltransferase gene in bovine cells.

Construction of an α-1,3-galactosyltransferase KO Vector The α-1,3-galactosyltransferase KO vector was generated as follows (FIG. 23). To isolate genomic DNA around exon 9 of the α-1,3-galactosyltransferase gene, a DNA probe was amplified by PCR using the following primer pair 5'-gat-gatgtctccaggatgcc-3' (SEQ ID NO: 61) and 5'-gacaagct-taatatccgcagg-3' (SEQ ID NO: 62). Using this probe, a bovine genomic λ phage library was screened, and 7 positive λ phage clones were identified. One clone, which contained DNA from a male Charolais bovine fibrolast cell, was analyzed further by restriction mapping. The Not I-Xho I genomic fragment containing exon 9 was subcloned into pBluescript II SK(−), and then both puro and STOP cassettes were inserted at the Avi I site in the Not I-Xho I genomic fragment which is 5' to the catalytic domain. A diphtheria toxin gene (DT-A, Gibco) was also added to the vector construct to kill cells in which the targeting cassette was integrated nonhomologously.

Transfection/Knockout Procedures Transfection of three fetal fibroblasts cell lines (two from a male Jersey bovine and one from a female Jersey bovine) was performed using a standard electroporation protocol as follows. The medium used to culture the bovine fetal fibroblasts contained 500 ml Alpha MEM (Gibco, 12561-049), 50 ml fetal calf serum (Hy-Clone #ABL13080), 5 ml penicillin-streptomycin (SIGMA), and 1 ml 2-mercaptoethanol (Gibco/BRL #21985-023). On the day prior to transfection, cells were seeded on a T175 tissue culture flask with a targeted confluency of 80–100%, as determined by microscopic examination. On the day of transfection, about $10^7$ bovine fibroblasts cells were trypsinized and washed once with alpha-MEM medium. After resuspension of the cells in 800 µl of alpha-MEM, 30 µg of DNA was added to the cell suspension and mixed well by pipetting. The cell-DNA suspension was transferred into an electroporation cuvette and electroporated at 1,000 V and 50 µF. After that, the electroporated cells were plated onto twenty 24-well plates with the alpha-MEM medium supplemented with the serum. After a 48 hour-culture, the medium was replaced with medium containing 1 µg/ml of puromycin, and the cells were cultured for 2–3 weeks to select puromycin resistant cells. After selection, all colonies which reached close to 100% confluency were picked, and genomic DNA was extracted from the colonies to screen for the desired homologous recombination events by PCR.

Screening for Targeted Integrations As described above, the genomic DNA was extracted from each 24-well independently using the PUREGENE DNA isolation Kit (Gentra SYSTEMS) according to the manufacture's protocol. Each genomic DNA sample was resuspended in 20 µl of 10 mM Tris-Cl (pH 8.0) and 1 mM EDTA (EDTA). Screening by PCR was performed using the following primer pair 5'-aagaagagaaaggtagaagaccccaaggac-3' (SEQ ID NO: 63) and 5'-cctgggtatagacaggtgggtattgtgc-3' (SEQ ID NO: 64). The sequence of one primer is located in the α-1,3-galactosyltransferase KO vector, and the sequence of the other primer is located just outside of the integrated vector in the targeted endogenous locus (FIG. 23). Therefore, the expected PCR product should be detected only when the KO vector is integrated into the targeted locus by homologous recombination.

The PCR reaction mixtures contained 18.9 µl water, 3 µl of 10×LA PCR buffer II ($Mg^{2+}$ plus), 4.8 µl of dNTP mixture, 10 pmol forward primer, 10 pmol of reverse primer, 1 µl of genomic DNA, and 0.3 µl of LA Taq. Forty cycles of PCR were performed by incubating the reaction mixtures at the following conditions: 85° C. for three minutes, 94° C. for one minute, 98° C. for 10 seconds, and 68° C. for 15 minutes. After PCR, the reaction mixtures were analyzed by electrophoresis. Puromycin-resistant clones which generated PCR products of the expected size were selected (FIG. 23). Thus, bovine fibroblast cell lines in which one allele of the α-1,3-galactosyltransferase locus is mutated by the KO vector were successfully generated.

EXAMPLE 5

Alternative Method for Producing Transgenic Ungulates using Adeno-Associated Viruses to Mutate an Endogenous Gene Adeno-associated virus (AAV) can be used for specific replacement of targeted sequences present in the genome of cells (Inoue et al., Mol. Ther. 3(4):526–530, 2001); Hirata et al., J Virol. 74(10):16536–42, 2000); Inoue et al., J. Virol. 73(9):7376–80, 1999); and Russell et al., Nat. Genet. 18(4): 325–30,1998)). The gene targeting rate is highly efficient in comparison to more conventional gene targeting approaches. AAV has a broad range of host and tissue specificities, including specificity for both bovine and human skin fibroblasts. Thus, AAV can be used to produce transgenic ungulate cells containing one or more mutations in an endogenous immunoglobulin (e.g., mu heavy chain, lambda light chain, kappa light chain, or J chain), alpha-(1, 3)-galactosyltransferase, or prion gene. These transgenic cells can then be used in the nuclear transfer methods described herein to produce transgenic ungulates of the present invention.

Using AAV resulted in homologous recombination of the bovine immunoglobulin heavy chain locus at higher frequencies than previously obtained using traditional gene targeting strategies (i.e., electroporation and lipofection procedures). In the first round of gene targeting experiments, five appropriately targeted fibroblast clones were obtained out of 73 stable transductants containing the DNA introduced through an AAV vector.

These experiments were carried out as follows.

Figure 24:
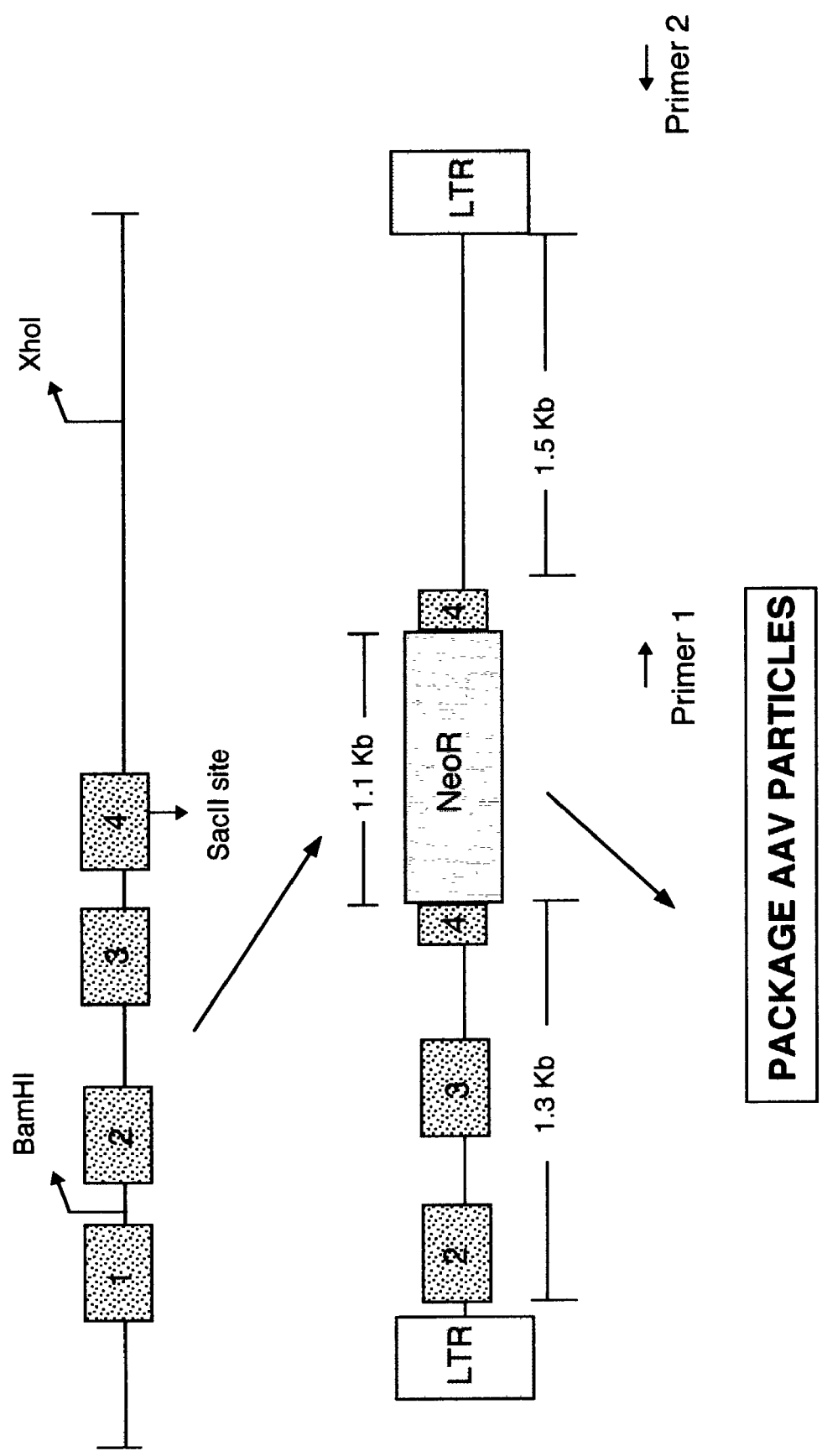
FIG. 24 is a schematic illustration of a BamHI-XhoI fragment containing exons 2, 3, and 4 that was used as a backbone for the AAV targeting vector. A neomycin resistance marker was used for insertional mutagenesis of the locus by insertion into exon 4. The location of the annealing sites for the PCR primers that were used for subsequent confirmation of appropriate targeting is indicated.

AAV Knockout Vectors AAV constructs can disrupt a gene either by simple insertion of foreign sequences or replacement of endogenous sequences with new sequence present in the AAV vector. FIG. 24 shows an AAV construct in which all four coding exons of the bovine immunoglobulin heavy chain mu constant region are present on a 2822 base pair BamHI-XhoI fragment. A 1.16 Kb fragment containing a neomycin resistance marker present in the commercially available vector, pMC1Neo, was inserted into a SacII site present in exon 4 of the mu heavy chain locus from a Holstein bovine. This locus is the one contained in the phage clone isolated to generate the knockout vector described in Example 1. To generate the AVV vector, the SacII site in the mu heavy chain locus was filled in to create blunt ends, which were then ligated to blunt SalI linkers (New England Biolabs). Then, the XhoI fragment of pMC1Neo, which contains the neomycin resistance gene, was ligated to the SalI site added to the locus through the SalI linker. This ligation can be performed because the XhoI and SalI restriction sites have compatible ends. This knockout vector causes a disruptional insertion of the neomycin resistance gene into the endogenous mu heavy chain gene, thereby inactivating the mu heavy chain gene. This gene inactivation occurs without deleting regions of the endogenous mu locus.

Figure 25:
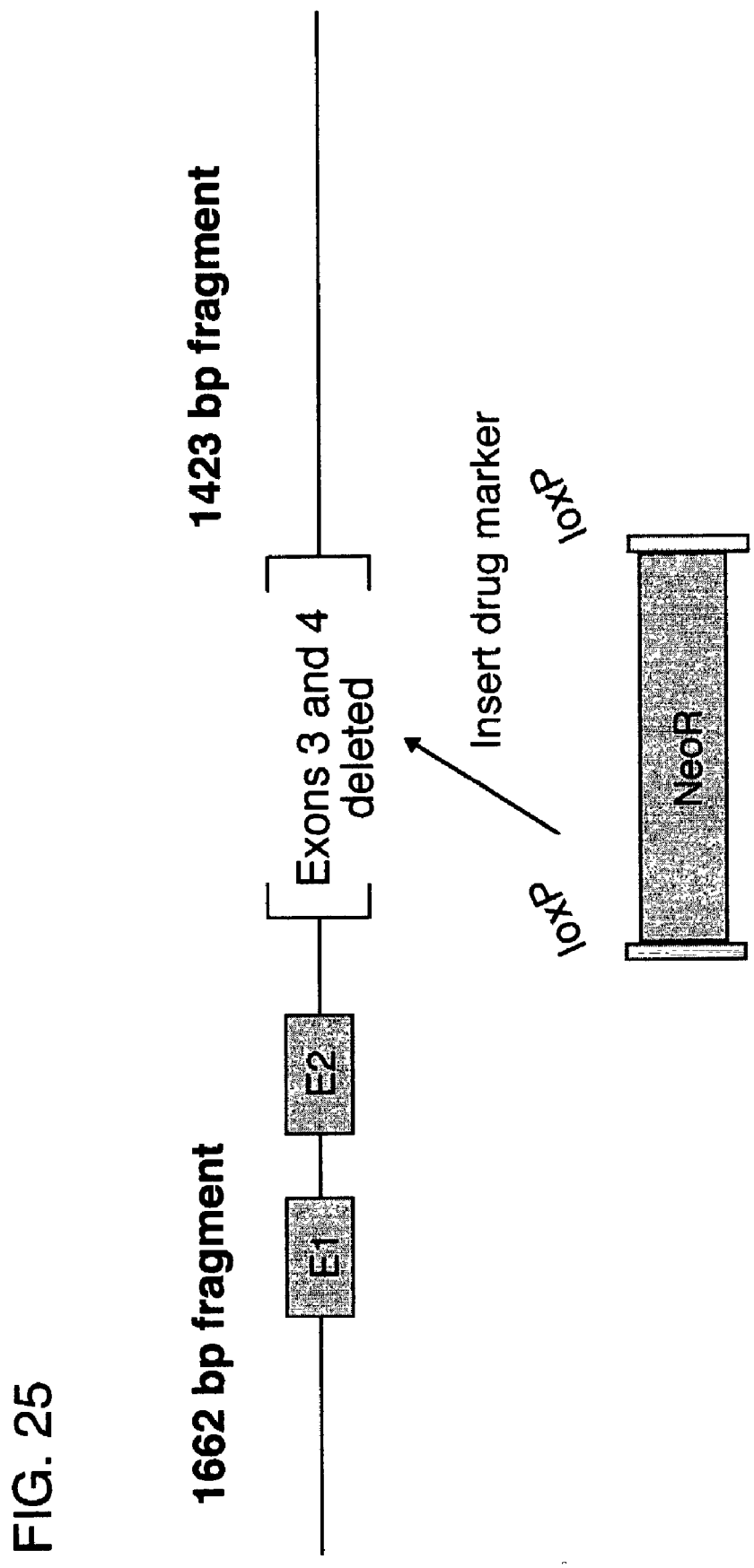
FIG. 25 is a schematic illustration of the construction of an adeno-associated viral construct designed to remove endogenous bovine IgH sequence.

An alternative vector was designed to remove exons 3 and 4 from the endogenous locus during targeting, resulting in the replacement of these two exons with a functional copy of the neomycin resistance gene (FIG. 25). This construct was generated using PCR amplification of genomic DNA from a female Jersey bovine. In particular, the 3' region of homology was amplified using the following primers: 5' GGGGTCTAGAgcagacactacactgatgggcccttggtcc 3' (SEQ ID NO: 65), which adds a XbaI restriction site, and 5' GGGGAAGCTTcgtgtccctggtcctgtctgacacag 3' (SEQ ID NO: 66), which adds a HindIII restriction site. The 5' region of homology was amplified with primers 5' GGGGCTCGAGgtcggcgaaggatgggggaggtg 3' (SEQ ID NO: 67), which adds a XhoI restriction site, and 5' GGGGGGTAC-Cgctgggctgagctgggcagagtggg 3' (SEQ ID NO: 68), which adds a KpnI restriction site. The capitalized nucleotides in these primer sequences are nucleotides that do not anneal to the mu heavy chain locus but are included in the primers to add restriction sites to facilitate later subcloning steps. The first four guanines are added to separate the restriction sites from the very end of the primers because restriction enzymes do not cleave sites that are at the very end of primers as well as internal sites. The 5' region of homology is 1.5 Kb long and contains exons 1 and 2. The 5' region of homology also contains the first 25 nucleotides of exon 3 to maintain the splice acceptor site of exon 3. The splice acceptor site allows exon 3 to be used for splicing and thus prevents the possible splicing of exons 1 and 2 to the downstream transmembrane domain to form an aberrant membrane-bound product. The 3' region of homology is 1.24 Kb long and contains the region immediately downstream of exon 4.

For the construct shown in FIG. 24, the targeting cassette was inserted into the AAV vector reported by Ryan et al. (J. of Virology 70:1542–1553, 1996), which contains viral long terminal repeat (LTR) sequences, using standard methods. The AAV vector was packaged into capsids using the TtetA2 packaging cell line as previously described (Inoue and Russell, 1998, J. Virol. 72:7024–7031, 1998) and purified as previously described (Zolotukhin et al., Gene Therapy, 6: 973–985, 1999). For the construct shown in FIG. 25, the above method or any other standard method can be used to insert the targeting cassette into the AAV vector described by Ryan et aL or any other AAV vector (such as a commercially available vector from Stratagene) and generate viruses containing the vector.

Transduction Procedures Fibroblasts from a female Jersey bovine were seeded into one well of a 48 well tissue culture plate at 40,000 cells per well and cultured in complete medium at 38.5° C. and 5% $CO_2$ until cells attached to the bottom surface of the well. Once cells adhered, the medium was removed and replaced with 0.2 ml of fresh medium containing AAV particles with the vector shown in FIG. 24 at a multiplicity of infection (MOI) of 500–20,000 particles/cell. The MOI was chosen based on pilot experiments that determined the resulting numbers of colonies and the spacing of the colonies during the drug selection phase. Plates were incubated overnight. After this incubation, the transduced wells were rinsed with calcium and magnesium-free PBS and detached from the wells using either trypsin or the cell dissociation buffer described above. A uniform cell suspension was obtained by gentle pipetting of the detached cells, and the cells from the well were redistributed among ten 100 mm tissue culture dishes. Dishes were incubated with complete medium overnight.

Following this incubation of the 100 mm dishes, the medium was replaced with selective medium containing G418 at a concentration of 350 micrograms/ml. Selective medium was changed every 2–3 days until colonies were macroscopically visible on the surface of the dish. At that point, individual colonies were picked and transferred into their own vessels.

Regions containing colonies were marked on the outer surface of the tissue culture dish. Once all colonies were circled, medium was aspirated off the plates, and the plates were washed three times with calcium and magnesium-free PBS. After washing, the plates were flooded with a 1:25 dilution of 1× trypsin and allowed to sit at room temperature until the colonies had visibly begun to detach from the surface of the plate. Plates were kept stationary to prevent detached colonies from floating to another location of the plate. A pipet tip was used to pick up cell clumps in a volume of 50 microliters, and the contents of the pipet tip were transferred into one well of a 24 well tissue culture plate. Once all colonies were transferred, complete medium containing G418 was added, and the isolated clones were allowed to proliferate to near confluency.

When an individual well was close to confluency, it was washed twice with calcium and magnesium free PBS. Cells were detached using 0.2 ml of cell dissociation buffer. Of this cell suspension, 20 µl was transferred to a new 24 well plate, and the remaining cells were allowed to reattach to the surface of the original 24 well plate following the addition of 2.0 ml of complete medium. The original plate was incubated to 100% confluency. The new plate serves as a source of appropriately targeted cells for future bovine cloning procedures.

When a well from the original 24 well plate became 100% confluent, the medium was removed, and the cells were washed once with PBS. PBS was removed and replaced with a cell lysis buffer adopted from Laird et al. (Nucleic Acids Res. 19:4293, 1991). Briefly, 0.2 ml of lysis buffer containing 200 mM NaCl, 100 mM Tris-HCl pH 8.5, 5 mM EDTA, 0.2% SDS, and 100 ug/ml proteinase K was added to the well. The plate was returned to the incubator for between three hours and overnight. The viscous cell lysate was then transferred to a microfuge tube. An equal volume of isopropanol was added to precipitate DNA. Following a 10 minute spin in a microfuge, the supernatant was discarded, and the pellet was washed once with 0.5 ml of 70% ethanol. After removal of the ethanol, the DNA pellet was air-dried and resuspended in 35 microliters of TE buffer (10 mM Tris pH 8 and 1 mM EDTA). Aliquots of 3 µl were used for PCR analysis.

PCR analysis DNA samples from drug resistant clones transduced with AAV particles were screened for appropriate targeting of the vector using PCR analysis. This screening strategy used one primer that anneals within the DNA encoding the drug selection marker and another primer that anneals within the targeted locus, but outside the sequence present in the AAV targeting particles. PCR products are only detected if the AAV targeting DNA has integrated into the desired location of the endogenous genome.

Figure 26:
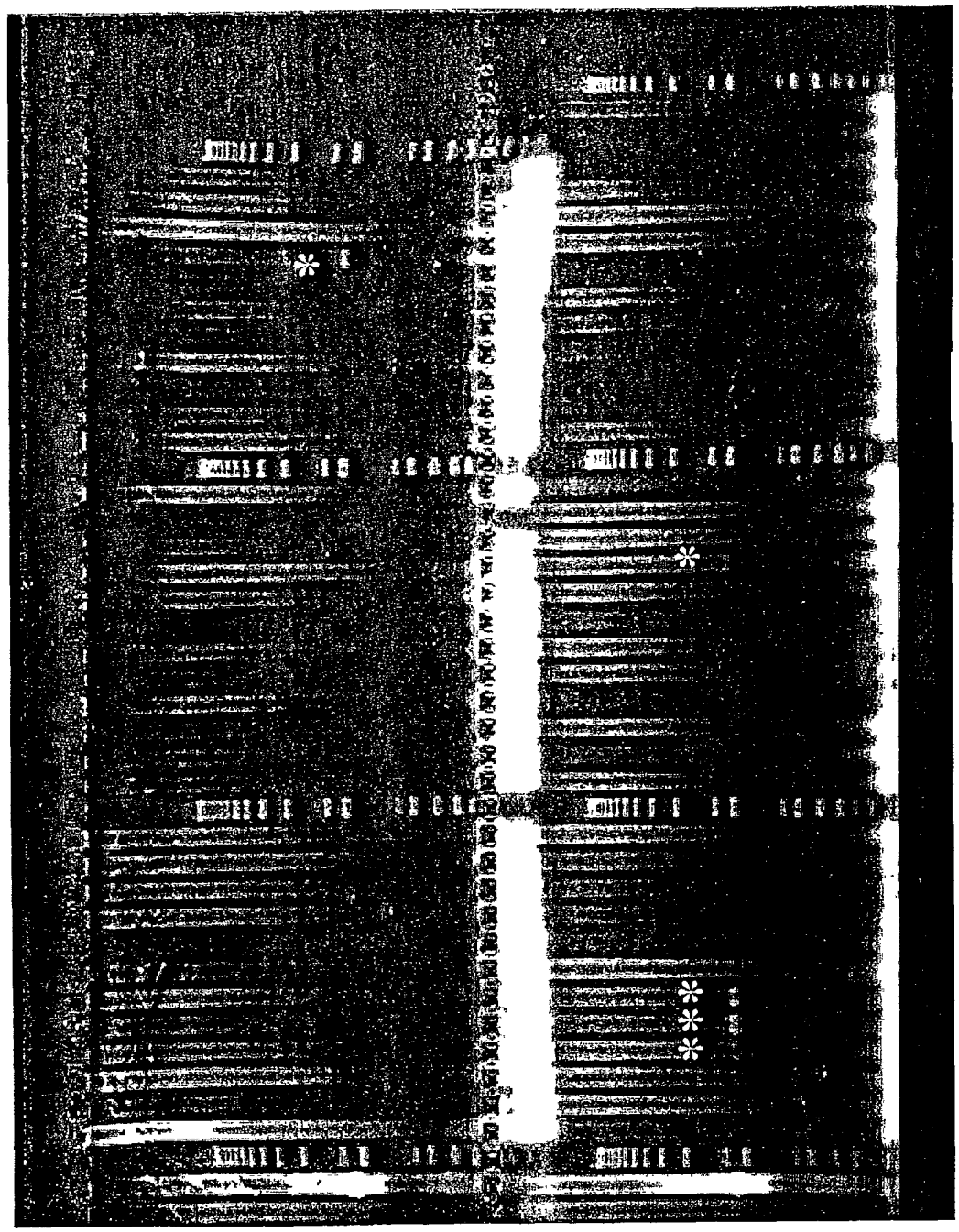
FIG. 26 is a picture of an agarose gel showing the PCR analysis of individually transduced clones for appropriate targeting events. The vector used in this experiment is shown in FIG. 24. PCR products indicative of appropriate targeting are marked with asterisks.

Results from a single targeting experiment using these AAV particles are shown in FIG. 26. Based on this analysis, five out of 73 independent clones contained the appropriate targeted vector DNA.

This method may also be used with the AAV vector shown in FIG. 25 or with any other appropriate adenovirus or adeno-associated viral vector. If desired, the second mu heavy chain allele can be mutated in the isolated colonies by transducing them with an AAV vector with a different antibiotic resistance gene (i.e., a gene other than a neomycin resistance gene). To select the resulting homozygous knockout cells, the infected cells are cultured in the presence of the corresponding antibiotic. Alternatively, the isolated colonies can be transduced with an AAV vector containing a neomycin resistance gene and cultured in the presence of a high concentration of antibiotic (i.e., a concentration of antibiotic that kills heterozygous knockout cells but not homozygous knockout cells).

OTHER EMBODIMENTS

From the foregoing description, it will be apparent that variations and modifications may be made to the invention described herein to adopt it to various usages and conditions. Such embodiments are also within the scope of the following claims.

All publications mentioned in this specification are herein incorporated by reference to the same extent as if each independent publication or patent application was specifically and individually indicated to be incorporated by reference.

The invention claimed is:

1. A transgenic bovine whose cells comprise one or more artificial chromosomes, each artificial chromosome comprising one or more human immunoglobulin heavy or light chain loci that undergo rearrangement and are expressed in B-cells to produce a human immunoglobulin in response to exposure to one or more antigens.

2. The transgenic bovine of claim 1, wherein said one or more artificial chromosomes comprise a human artificial chromosome.

3. The transgenic bovine of claim 2, wherein said human artificial chromosome is ΔHAC or ΔΔHAC.

4. The transgenic bovine of claim 2, wherein said human artificial chromosome is derived from one or more of human chromosome 14, human chromosome 2, and human chromosome 22.

5. The transgenic bovine of claim 1, wherein said immunoglobulin loci comprise both a human immunoglobulin light chain locus and human immunoglobulin heavy chain locus.

6. An isolated B-cell obtained from a transgenic bovine of claim 1, wherein the B-cell comprises one or more artificial chromosomes, each artificial chromosome comprising one or more human immunoglobulin loci that undergo rearrangement and are expressed to produce a human immunoglobulin in response to exposure to one or more antigens.

7. An isolated transgenic bovine B-cell comprising one or more artificial chromosomes, each artificial chromosome comprising one or more human immunoglobulin heavy or light chain loci that undergo rearrangement and are expressed to produce a human immunoglobulin in response to exposure to one or more antigens.

8. The cell of claim 7, wherein said one or more artificial chromosomes comprise a human artificial chromosome.

9. The cell of claim 8, wherein said human artificial chromosome is derived from one or more of human chromosome 14, human chromosome 2, and human chromosome 22.

10. The cell of claim 8, wherein said human artificial chromosome is ΔHAC or ΔΔHAC.

11. The cell of claim 7, wherein said immunoglobulin loci comprise both a human immunoglobulin light chain locus and human immunoglobulin heavy chain locus.

12. A method of producing human antibodies, said method comprising the steps of: (a) administering one or more antigens of interest to a transgenic bovine whose cells comprise one or more artificial chromosomes, each artificial chromosome comprising one or more human immunoglobulin heavy or light chain loci that undergo rearrangement and are expressed in B-cells, resulting in production of human antibodies against said one or more antigens; and (b) recovering said human antibodies from said bovine.

13. The method of claim 12, wherein said one or more artificial chromosomes comprise a human artificial chromosome.

14. The method of claim 13, wherein said human artificial chromosome is derived from one or more of human chromosome 14, human chromosome 2, and human chromosome 22.

15. The method of claim 13, wherein said human artificial chromosome is ΔHAC or ΔΔHAC.

16. A method of producing human antibodies to one or more antigens, said method comprising recovering human antibodies from a transgenic bovine whose cells comprise one or more artificial chromosomes, each artificial chromosome comprising one or more human immunoglobulin heavy or light chain loci that undergo rearrangement and are expressed in B-cells, resulting in production of human antibodies against said one or more antigens.

17. The method of claim 16, wherein said one or more artificial chromosomes comprise a human artificial chromosome.

18. The method of claim 17, wherein said human artificial chromosome is derived from one or more of human chromosome 14, human chromosome 2, and human chromosome 22.

19. The method of claim 17, wherein said human artificial chromosome is ΔHAC or ΔΔHAC.

\* \* \* \* \*

UNITED STATES PATENT AND TRADEMARK OFFICE
CERTIFICATE OF CORRECTION

PATENT NO. : 7,074,983 B2
APPLICATION NO. : 09/988115
DATED : July 11, 2006
INVENTOR(S) : Robl et al.

It is certified that error appears in the above-identified patent and that said Letters Patent is hereby corrected as shown below:

On the Title Page, Item 56, under References Cited, under OTHER PUBLICATIONS, in Parng, Chuen-Lei et al., replace "1g" with -- Ig --.

On the Title Page, Item 56 on Page 2, under References Cited, under OTHER PUBLICATIONS, in Aheam et al., replace "Aheam" with -- Ahearn --.

On the Title Page, Item 56 on Page 2, under References Cited, under OTHER PUBLICATIONS, in Jonak et al., replace "*Hybridomonas*" with -- *Hybridomas* --.

On the Title Page, Item 56 on Page 3, under References Cited, under OTHER PUBLICATIONS, in Miake-Lye et al., replace "Mitolic" with -- Mitotic --.

On the Title Page, Item 56 on Page 3, under References Cited, under OTHER PUBLICATIONS, in Steen et al., replace "Milotic" with -- Mitotic --.

On the Title Page, Item 56 on Page 3, under References Cited, under OTHER PUBLICATIONS, in Fishwild et al., replace "Highavidity human igG monoclonal antibodies from a novel strain of minilocus transgenic mice," with -- "High-avidity Human IgG Kappa Monoclonal Antibodies From a Novel Strain of Minilocus Transgenic Mice," --.

On the Title Page, Item 56 on Page 4, under References Cited, under OTHER PUBLICATIONS, in Mendez et al., replace "Functional transplant of megabase human immunoglobulin toci recapitulates human antibody response in mice," with -- "Functional Transplant of Megabase Human Immunoglobulin Loci Recapitulates Human Antibody Response in Mice," --.

Column 5, Line 11, replace "intravenenous" with -- intravenous --.

Column 6, Line 66, replace "as a an antibody" with -- as an antibody --.

Column 8, Line 54, replace "(intraveneous" with -- (intravenous --.

Column 10, Line 22, replace "immunogloblulin" with -- immunoglobulin --.

Column 12, Line 55, replace "a embryo" with -- an embryo --.

UNITED STATES PATENT AND TRADEMARK OFFICE
CERTIFICATE OF CORRECTION

PATENT NO. : 7,074,983 B2
APPLICATION NO. : 09/988115
DATED : July 11, 2006
INVENTOR(S) : Robl et al.

It is certified that error appears in the above-identified patent and that said Letters Patent is hereby corrected as shown below:

Column 13,
    Line 10, replace "construct construct" with -- construct --.
    Line 14, replace "polynucloetide" with -- polynucleotide --.

Column 15,
    Line 2, replace "do not" with -- does not --.
    Line 37, replace "substituted therefor with" with -- substituted, therefore, with --.
    Line 51, replace "immunoglobulon" with -- immunoglobulin --.

Column 22,
    Line 51, replace "inactive" with -- inactivate --.
    Line 53, replace "procine" with -- porcine --.

Column 23,
    Line 3, replace "Biothech.," with -- Biotech., --.
    Line 23, replace "containg" with -- containing --.
    Line 60, replace "maybe" with -- may be --.

Column 27, Line 28, replace "*Coryunebacterium diptheriae*" with -- *Corynebacterium diphtheriae* --.

Column 28, Line 3, replace "Intraveneous" with -- Intravenous --.

Column 36, Line 27, replace "were mixed were filtered" with -- were mixed and filtered --.

Column 38, Line 59, replace "months" with -- months. --.

Column 40, Line 48, replace "minute" with -- minutes --.

Column 41, Line 17, replace "a" with -- an --.

Column 44, Line 61, replace "C/2-3," with -- C$\lambda$2-3, --.

Column 45,
    Line 23, replace "percent" with -- percentage --.
    Line 61, replace "hemizgously" with -- hemizygously --.

UNITED STATES PATENT AND TRADEMARK OFFICE
CERTIFICATE OF CORRECTION

PATENT NO. : 7,074,983 B2
APPLICATION NO. : 09/988115
DATED : July 11, 2006
INVENTOR(S) : Robl et al.

It is certified that error appears in the above-identified patent and that said Letters Patent is hereby corrected as shown below:

Column 46,
 Line 31, replace "MluI The" with -- MluI. The --.
 Line 61, replace "hours The" with -- hours. The --.

Column 47, Line 29, replace "minutes" with -- minute --.

Column 49, Line 12, replace "puromcying" with -- puromycin --.

Column 52, line 32, replace "Sail linker" with -- SaII linker --.

Column 53, Line 16, replace "Ryan et aL" with -- Ryan et al. --.

Signed and Sealed this

First Day of July, 2008

JON W. DUDAS
*Director of the United States Patent and Trademark Office*

UNITED STATES PATENT AND TRADEMARK OFFICE
CERTIFICATE OF CORRECTION

PATENT NO.       : 7,074,983 B2                                   Page 1 of 1
APPLICATION NO.  : 09/988115
DATED            : July 11, 2006
INVENTOR(S)      : Robl et al.

It is certified that error appears in the above-identified patent and that said Letters Patent is hereby corrected as shown below:

On the Title Page,

Item [*] Notice:    Subject to any disclaimer, the term of this patent is extended or adjusted under 35 USC 154(b) by 68 days Delete the phrase "by 68 days" and insert -- by 129 days --

Signed and Sealed this

Eleventh Day of November, 2008

JON W. DUDAS
*Director of the United States Patent and Trademark Office*

SEQUENCE LISTING

<160> NUMBER OF SEQ ID NOS: 68

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
agtgagataa gcagtggatg                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
cttgtgctac tcccatcact                                          20

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
ggagaccacc aaaccctcca aa                                       22

<210> SEQ ID NO 4
<211> LENGTH: 23
<212> TYPE: DNA
<213> ORGANISM: Artificial Sequence
<220> FEATURE:
<223> OTHER INFORMATION: Synthetic Primer

<400> SEQUENCE: 4
gagagttgca gaagggtyg act                                       23

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
accacctatg acagcgtgac                                          20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
gtggcagcaa gtagacatcg                                          20

<210> SEQ ID NO 7
<211> LENGTH: 22

```
<212> TYPE: DNA
<213> ORGANISM: Artificial Sequence
<220> FEATURE:
<223> OTHER INFORMATION: Synthetic Primer

<400> SEQUENCE: 7
gtcatcatct ctgccccttc tg                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic Primer

<400> SEQUENCE: 8
aacaacttct tgatgtcatc at                                              22

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
ccctcctctt tgtgctgtca                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
caccgtgctc tcatcggatg                                                 20

<210> SEQ ID NO 11
<211> LENGTH: 23
<212> TYPE: DNA
<213> ORGANISM: Artificial Sequence
<220> FEATURE:
<223> OTHER INFORMATION: Synthetic Primer

<400> SEQUENCE: 11
caggtgcagc tggtggagtc tgg                                             23

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
caggagaaag tgatggagtc                                                 20

<210> SEQ ID NO 13
<211> LENGTH: 22
<212> TYPE: DNA
<213> ORGANISM: Artificial Sequence
<220> FEATURE:
<223> OTHER INFORMATION: Synthetic Primer

<400> SEQUENCE: 13
```
ggagaccacc aaaccctcca aa                                                22

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
gtggcagcaa gtagacatcg                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
caggagaaag tgatggagtc                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
aggcagccaa cggccacgct                                                   20

<210> SEQ ID NO 17
<211> LENGTH: 23
<212> TYPE: DNA
<213> ORGANISM: Artificial Sequence
<220> FEATURE:
<223> OTHER INFORMATION: Synthetic Primer

<400> SEQUENCE: 17
caggtgcagc tggtggagtc tgg                                               23

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
agtgagataa gcagtggatg                                                   20

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
cttgtgctac tcccatcact                                                   20

<210> SEQ ID NO 20
<211> LENGTH: 22
<212> TYPE: DNA
<213> ORGANISM: Artificial Sequence

```
<220> FEATURE:
<223> OTHER INFORMATION: Synthetic Primer

<400> SEQUENCE: 20
ggagaccacc aaaccctcca aa                                              22

<210> SEQ ID NO 21
<211> LENGTH: 23
<212> TYPE: DNA
<213> ORGANISM: Artificial Sequence
<220> FEATURE:
<223> OTHER INFORMATION: Synthetic Primer

<400> SEQUENCE: 21
gagagttgca gaagggggtyg act                                            23

<210> SEQ ID NO 22
<211> LENGTH: 22
<212> TYPE: DNA
<213> ORGANISM: Artificial Sequence
<220> FEATURE:
<223> OTHER INFORMATION: Synthetic Primer

<400> SEQUENCE: 22
ggagaccacc aaaccctcca aa                                              22

<210> SEQ ID NO 23
<211> LENGTH: 22
<212> TYPE: DNA
<213> ORGANISM: Artificial Sequence
<220> FEATURE:
<223> OTHER INFORMATION: Synthetic Primer

<400> SEQUENCE: 23
gagagttgca gaagggggtga ct                                             22

<210> SEQ ID NO 24
<211> LENGTH: 23
<212> TYPE: DNA
<213> ORGANISM: Artificial Sequence
<220> FEATURE:
<223> OTHER INFORMATION: Synthetic Primer

<400> SEQUENCE: 24
caggtgcagc tggtggagtc tgg                                             23

<210> SEQ ID NO 25
<211> LENGTH: 20
<212> TYPE: DNA
<213> ORGANISM: Artificial Sequence
<220> FEATURE:
<223> OTHER INFORMATION: Synthetic Primer

<400> SEQUENCE: 25
caggagaaag tgatggagtc                                                 20

<210> SEQ ID NO 26
<211> LENGTH: 22
<212> TYPE: DNA
<213> ORGANISM: Artificial Sequence
<220> FEATURE:
<223> OTHER INFORMATION: Synthetic Primer

<400> SEQUENCE: 26
gtcatcatct ctgccccttc tg                                              22
```

<210> SEQ ID NO 27
<211> LENGTH: 22
<212> TYPE: DNA
<213> ORGANISM: Artificial Sequence
<220> FEATURE:
<223> OTHER INFORMATION: Synthetic Primer

<400> SEQUENCE: 27
aacaacttct tgatgtcatc at                                        22

<210> SEQ ID NO 28
<211> LENGTH: 29
<212> TYPE: DNA
<213> ORGANISM: Artificial Sequence
<220> FEATURE:
<223> OTHER INFORMATION: Synthetic Primer

<400> SEQUENCE: 28
gggaattcgg gtagaagttc actgatcag                                 29

<210> SEQ ID NO 29
<211> LENGTH: 28
<212> TYPE: DNA
<213> ORGANISM: Artificial Sequence
<220> FEATURE:
<223> OTHER INFORMATION: Synthetic Primer

<400> SEQUENCE: 29
gggaattcgg gtagaagtca cttatgag                                  28

<210> SEQ ID NO 30
<211> LENGTH: 28
<212> TYPE: DNA
<213> ORGANISM: Artificial Sequence
<220> FEATURE:
<223> OTHER INFORMATION: Synthetic Primer

<400> SEQUENCE: 30
gggaattcgg gtagaagtca cttacgag                                  28

<210> SEQ ID NO 31
<211> LENGTH: 29
<212> TYPE: DNA
<213> ORGANISM: Artificial Sequence
<220> FEATURE:
<223> OTHER INFORMATION: Synthetic Primer

<400> SEQUENCE: 31
cccccaagct trcckgstyy cctctcctc                                 29

<210> SEQ ID NO 32
<211> LENGTH: 29
<212> TYPE: DNA
<213> ORGANISM: Artificial Sequence
<220> FEATURE:
<223> OTHER INFORMATION: Synthetic Primer

<400> SEQUENCE: 32
cccccaagct tgcctggacc cctctctgg                                 29

<210> SEQ ID NO 33
<211> LENGTH: 32
<212> TYPE: DNA
<213> ORGANISM: Artificial Sequence
<220> FEATURE:
<223> OTHER INFORMATION: Synthetic Primer

```
<400> SEQUENCE: 33
atcggcaaag cttggacccc tctctggctc ac                              32

<210> SEQ ID NO 34
<211> LENGTH: 29
<212> TYPE: DNA
<213> ORGANISM: Artificial Sequence
<220> FEATURE:
<223> OTHER INFORMATION: Synthetic Primer

<400> SEQUENCE: 34
cccccaagct tctcggcgtc cttgcttac                                  29

<210> SEQ ID NO 35
<211> LENGTH: 29
<212> TYPE: DNA
<213> ORGANISM: Artificial Sequence
<220> FEATURE:
<223> OTHER INFORMATION: Synthetic Primer

<400> SEQUENCE: 35
gggaattcgg gtagaagttc actgatcag                                  29

<210> SEQ ID NO 36
<211> LENGTH: 28
<212> TYPE: DNA
<213> ORGANISM: Artificial Sequence
<220> FEATURE:
<223> OTHER INFORMATION: Synthetic Primer

<400> SEQUENCE: 36
gggaattcgg gtagaagtca cttatgag                                   28

<210> SEQ ID NO 37
<211> LENGTH: 28
<212> TYPE: DNA
<213> ORGANISM: Artificial Sequence
<220> FEATURE:
<223> OTHER INFORMATION: Synthetic Primer

<400> SEQUENCE: 37
gggaattcgg gtagaagtca cttacgag                                   28

<210> SEQ ID NO 38
<211> LENGTH: 29
<212> TYPE: DNA
<213> ORGANISM: Artificial Sequence
<220> FEATURE:
<223> OTHER INFORMATION: Synthetic Primer

<400> SEQUENCE: 38
cccccaagct trcckgstyy cctctcctc                                  29

<210> SEQ ID NO 39
<211> LENGTH: 28
<212> TYPE: DNA
<213> ORGANISM: Artificial Sequence
<220> FEATURE:
<223> OTHER INFORMATION: Synthetic Primer

<400> SEQUENCE: 39
gggaattcgg gtagaagtca ctgatcag                                   28

<210> SEQ ID NO 40
```

```
<211> LENGTH: 28
<212> TYPE: DNA
<213> ORGANISM: Artificial Sequence
<220> FEATURE:
<223> OTHER INFORMATION: Synthetic Primer

<400> SEQUENCE: 40
gggaattcgg gtagaagtca cttatgag                                28

<210> SEQ ID NO 41
<211> LENGTH: 28
<212> TYPE: DNA
<213> ORGANISM: Artificial Sequence
<220> FEATURE:
<223> OTHER INFORMATION: Synthetic Primer

<400> SEQUENCE: 41
gggaattcgg gtagaagtca cttacgag                                28

<210> SEQ ID NO 42
<211> LENGTH: 30
<212> TYPE: DNA
<213> ORGANISM: Artificial Sequence
<220> FEATURE:
<223> OTHER INFORMATION: Synthetic Primer

<400> SEQUENCE: 42
cttgaagacg aaagggcctc gtgatacgcc                              30

<210> SEQ ID NO 43
<211> LENGTH: 30
<212> TYPE: DNA
<213> ORGANISM: Artificial Sequence
<220> FEATURE:
<223> OTHER INFORMATION: Synthetic Primer

<400> SEQUENCE: 43
ctgagacttc ctttcaccct ccaggcaccg                              30

<210> SEQ ID NO 44
<211> LENGTH: 31
<212> TYPE: DNA
<213> ORGANISM: Artificial Sequence
<220> FEATURE:
<223> OTHER INFORMATION: Synthetic Primer

<400> SEQUENCE: 44
cgatgaatgc cccatttcac ccaagtctgt c                            31

<210> SEQ ID NO 45
<211> LENGTH: 23
<212> TYPE: DNA
<213> ORGANISM: Artificial Sequence
<220> FEATURE:
<223> OTHER INFORMATION: Synthetic Primer

<400> SEQUENCE: 45
ctgagccaag cagtggcccc gag                                     23

<210> SEQ ID NO 46
<211> LENGTH: 26
<212> TYPE: DNA
<213> ORGANISM: Artificial Sequence
<220> FEATURE:
<223> OTHER INFORMATION: Synthetic Primer

<400> SEQUENCE: 46
```

```
gggctgagac tgggtgaaca gaaggg                                          26

<210> SEQ ID NO 47
<211> LENGTH: 1479
<212> TYPE: DNA
<213> ORGANISM: Bovine

<400> SEQUENCE: 47
ggtaccgaaa ggcggccctg aacattctgc agtgagggag ccgcactgag aaagctgctt    60
catcgccggg agggagccag ccagctacga ttgtgagcac gctcacagtg cacacggcat   120
gtgcacggtc tcagcttaac caccttgaag gagtaactca ttaaagagcg tacgaatgca   180
ttgataaaat gcacctgaga caaattaatt tcttaaacat cgactttgaa aatgaatata   240
agtgagcagt tgataggctc tgaatgaaat accttccaac aggtgctgag aaccgccagg   300
agcagggaac ggactccccg tggagcccca aaggagccag ccctgatga tacctcggcc    360 ctgggccctc ctcacgctgg gagagagcca gctcctgttg ttcatgcctg gcctgtggtt   420
ctttgtcgtc atggccctca aacaagccca caggtcctgg cctgagtccc tcggcctgcg   480
tgcagccgcc ccctcccctg ctggaggcac cctgcctgcc gtggagcccc tcacccaacg   540
ttcccccgcc tgatgggttg ggccgcaaag acaccgttt aaccagaact gccttccagg    600
agcctactgc tgggaggcgg ccttctctgg gaccaggtcc actccactcc cttggatagt   660
cactgtcagg cccctggtgg ccccacaaga ggcgtcctgg gaagcccag tctccttcca    720 gcccctgaaa ttgcctccct ggagagccag atcaccctca cccagctccc tccctggcc    780 cccagggtct cctctcccat cccaccgccc accctaccct ggcgttgccg tcacagctaa   840
cctgacctcc ctgggttcga gcgtgccgcc gcccctgtcg gccccacct ggaccccgc     900 agcctatctc tgagggctaa tgcccctgtc cctgccccg ctgccagctg cccctctttt    960
ccaggccttt cctccgtgcc tctccagtcc tgcacctccc tgcagcttca cctgagactt   1020
cctttcaccc tccaggcacc gtcttctggc ctgcaggtga ggtctcgcgc tccctcaggg   1080
cacgatgtgg ctgcacacac accggccctc ctcccgagtc cctcctgcac acaccacgcg   1140
cacccgaggt tgacaagccc tgccgtggtt gggattccgg gaatggcggc agagaggggc   1200
ggggtgtcct tggggctggt ggcagggtcc tcatggatgc acacagcggc cccggctcag   1260
gccaccttgg gaaaccagtc ctgggatctg caactcggcc atgttcctgc atctggacca   1320
gccccaagac accaccccgg cgtggcgcca ctggcctggg aggagacaca tgtccctttc   1380
ccatcagcaa tgggttcagc actaggatat gcagcacaca ggagtgtggc ttgggggtaa   1440
aaaaaccttc acgaggaagc ggtttcacaa aataaagta                          1479

<210> SEQ ID NO 48
<211> LENGTH: 3120
<212> TYPE: DNA
<213> ORGANISM: Bovine
<220> FEATURE:
<221> NAME/KEY: misc_feature
<222> LOCATION: (1)...(3120)
<223> OTHER INFORMATION: n=a, t, c, g or no nucleotide

<400> SEQUENCE: 48
tctagaccca ccagcctcag ttgaggttaa atggacccaa agcatctcaa caatttgccc    60
aagtcaagcc agctcaatgg gttcccttct gttcacccag tctcagccca ccatggtaac   120
ccagcatacc ccggttaagc ccaggctagc ccagcccagc tgagcccagc tcagctcagt   180
```

-continued

| | | | | |
|---|---|---|---|---|
| tcagcccagt | tcaatccaga | tcagcccaat | ccaggccagc | tcatcgagct cagttcagct | 240 |
| cagctcaacc | ctctcagccc | agctcacctg | ctcagccaag | ctaagcccag ttcagcccag | 300 |
| ctcagcttaa | cccagctcac | ccactctgcc | cagctcagcc | cagccctgct caactcagcc | 360 |
| cagcacagcc | caacttggct | cagctcagct | tagcccagct | cagcccagct tacccactcc | 420 |
| gcccagctca | aacagcccag | gtcagcccaa | cctagctcag | ttcagcccag ctcagcccag | 480 |
| cccagctcag | cccagctcac | ccactctgcc | cagctcaaca | cagcccagct caacccagct | 540 |
| cagctcagtt | cagcccagct | cacccactct | gcccagctca | ggccagctca acccagccca | 600 |
| gcccagctca | ctcattctgc | caagctcagc | ccagctcaac | caggctcagc tcagctcagc | 660 |
| tcagccctgc | tgaccnnnnn | nnnnnnnnnn | nnnnnnnnnn | nnnnnnnnnn nnnnnnnnnn | 720 |
| nnnnnnnnnn | nnnnnnnnnn | nnnnnnnnnn | nnnnnnnnnn | nnnnnnnnnn nnnnnnnnnn | 780 |
| nnnnnnnnnn | nnnnnnnnnn | nnnnnnnnnn | nnnnnnnnnn | nnnnnnnnnn nnnnnnnnnn | 840 |
| nnnnnnnnnn | nnnnnnnnnn | nnnnnnnnnn | nnnnnnnnnn | nnnnnnnnnn nnnnnnnnnn | 900 |
| nnnnnnnnnn | nnnnnnnnnn | nnnnnnnnnn | nnnnnnnnnn | nnnnnnnnnn nnnnnnnnnn | 960 |
| nnnnnnnnnn | nnnnnnnnnn | nnnnnnnnnn | nnnnnnnnnn | nnnnnnnnnn nnnnnnnnnn | 1020 |
| nnnnnnnnnn | nnnnnnnnnn | nnnnnnnnnn | nnnnnnnnnn | nnnnnnnnnn nnnnnnnnnn | 1080 |
| nnnnnnnnnn | nnnnnnnnnn | nnnnnnnnnn | nnnnnnnnnn | nnnnnnnnnn nnnnnnnnnn | 1140 |
| nnnnnnnnnn | nnnnnnnnnn | nnnnnnnnnn | nnnnnnnnnn | nnnnnnnnnn nnnnnnnnnn | 1200 |
| nnnnnnnnnn | nnnnnnnnnn | nnnnnnnnnn | nnnnnnnnnn | nnnnnnnnnn nnnnnnnnnn | 1260 |
| nnnnnnnnnn | nnnnnnnnnn | nnnnnnnnnn | nnnnnnnnnn | nnnnnnnnnn nnnnnnnnnn | 1320 |
| nnnnnnnnnn | nnnnnnnnnn | nnnnnnnnnn | nnnnnnnnnn | nnnnnnnnnn nnnnnnnnnn | 1380 |
| nnnnnnnnnn | nnnnnnnnnn | nnnnnnnnnn | nnnnnnnnnn | nnnnnnnnnn nnnnnnnnnn | 1440 |
| nnnnnnnnnn | nnnnnnnnnn | nnnnnnnnnn | nnnnnnnnnn | nnnnnnnnnn nnnnnnnnnn | 1500 |
| nnnnnnnnnn | nnnnnnnnnn | nnnnnnnnnn | nnnnnnnnnn | nnnnnnnnnn nnnnnnnnnn | 1560 |
| nnnnnnnnnn | nnnnnnnnnn | nnnnnnnnnn | nnnnnnnnnn | nnnnnnnnnn nnnnnnnnnn | 1620 |
| nnnnngctca | gctcagccca | gctcagccca | gcccagccca | gctcacacac ttggcccacc | 1680 |
| tcagccactc | cattcagctc | agcccagctc | aacccagctc | agctcagctc aacctagctc | 1740 |
| agccaagcta | acccactcca | cccagctcag | cccagctcgc | ccactctgcc cagctcaacc | 1800 |
| cagctcagct | cagcccagcc | cagyccagcc | cagctcaccc | actccatcca gcccagccca | 1860 |
| gcccagctga | gcccagctca | actcagccta | acccagctca | gcccagccta acccagctca | 1920 |
| gcccagccca | accagctagc | tgagcccagc | tcagtgcagc | tcaacccagc tcagctcagc | 1980 |
| tagcccagcc | cagctcaacc | tggctcaacc | cggctcagcc | cagctcacct gctgtaggtg | 2040 |
| gcctgaaccg | cgaacacaga | catgaaagcc | cagtggttct | gacgagaaag ggtcagatcc | 2100 |
| tggaccatgg | ccacggctaa | aggccctggt | ctgtggacac | tgcccagctg ggctcatccc | 2160 |
| tcccagcctc | ttcccgcttc | tcctcctggg | agcccgctcg | cccctteecc tggtgcctga | 2220 |
| cacctccatc | ccgacaccag | gcccagctgg | cccttctccc | agctgtcagt caccactacc | 2280 |
| ctccactctg | ggtgaaaagc | ttgttggaga | ctttagcttc | cctagagcat ctcacaggct | 2340 |
| gagacacact | tgccaccctc | agagagaggc | cctgtctctg | ctgagcaggc agcgctgctt | 2400 |
| ctctgggaga | ggagagcctg | ggcacacgtc | cctgggtcct | ggcctcctgg gcacgtgcca | 2460 |
| tgggcctgag | atcccgcccc | gagtctaaaa | gagtcctggt | gactaactgc tctctggcaa | 2520 |
| atgtcctcat | taaaaaccac | aggaaatgca | tcttatctga | acctgctccc aattctgtct | 2580 |

```
ttatcacaaa gttctgctga gaaagaggat actctctagc acagagacca tctgaacccc    2640
aaagctgcat tgaacaccta agtgtggacg caggaagtgg tccctgtggg tgtgaagcac    2700
cccggcatcg caggcagtag gtaaagacag attcccttc aagtagaaac aaaaacaact    2760
catacaaaca tccctgggca gtgagtctgg ctgcaccggc tcctggtccc tggcatgtcc    2820
cctgggctct ctgacctggg cggattcctc cgaatccctt cgctgtgtta actcgtgacc    2880
tgcctactgg cctggggca gaggccaggc ccacacgtcc ccaggtgtgg gcagtcccag    2940 gagaccccc agccttggcg agcctgggga ctcagagcag agactgtccc tccagacggt    3000
cccaggcccc gctgactgcc gccccaccgg gcatcctctc aatccccag ctagtagtgt    3060 agcagagtaa ctcacgacga atgcccccgt ttcacccaag tctgtcctga gatgggtacc    3120
```

```
<210> SEQ ID NO 49
<211> LENGTH: 146
<212> TYPE: DNA
<213> ORGANISM: Bovine
<220> FEATURE:
<221> NAME/KEY: misc_feature
<222> LOCATION: (1)...(146)
<223> OTHER INFORMATION: n=a,t,c, or g

<400> SEQUENCE: 49
```

```
gggaaggaag tcctgtgcga ccanccaacg gccacgctgc tcgtatccga cggggaattc     60
tcacaggaga cgaggggaa aagggttggg gcggatgcac tccctgagga gacggtgacc    120
agggttccnt ggccccagnn gtcaaa                                         146
```

```
<210> SEQ ID NO 50
<211> LENGTH: 167
<212> TYPE: DNA
<213> ORGANISM: Bovine

<400> SEQUENCE: 50
```

```
tttgactact ggggccaggg aaccctggtc accgtctcct cagggagtgc atccgcccca     60 accttttcc ccctcgtctc ctgtgagaat tccccgtcgg atacgagcag cgtggccgtt    120
ggctgcctcg cacaggactt ccttcccgac tccatcactt tctcctg                 167
```

```
<210> SEQ ID NO 51
<211> LENGTH: 147
<212> TYPE: DNA
<213> ORGANISM: Bovine
<220> FEATURE:
<221> NAME/KEY: misc_feature
<222> LOCATION: (1)...(147)
<223> OTHER INFORMATION: n=a, t, c, or g

<400> SEQUENCE: 51
```

```
tttgacnnct ggggccangg aaccctggtc accgtctcct cagggagtgc atccgcccca     60
acccttttcc ccctcgtctc ctgtgagaat tccccgtcgg atacgagcag cgtggccgtt    120
ggntgcgtcg cacaggactt ccttccc                                        147
```

```
<210> SEQ ID NO 52
<211> LENGTH: 393
<212> TYPE: DNA
<213> ORGANISM: Bovine

<400> SEQUENCE: 52
```

```
ggaggcttgg tcaagcctgg agggtccctg agactctcct gtgcagcctc tggattcacc     60
```

```
ttcagtgact actacatgag ctggatccgc caggctccag ggaaggggct ggagtgggtt      120
tcatacatta gtagtagtgg tagtaccata tactacgcag actctgtgaa gggccgattc      180
accatctcca gggacaacgc caagaactca ctgtatctgc aaatgaacag cctgagagcc      240
gaggacacgg ctgtgtatta ctgtgcgaga ataactgggg atgcttttga tatctggggc      300
caagggacaa tggtcaccgt ctcttcaggg agtgcatccg ccccaaccct tttccccctc      360
gtctcctgtg agaattcccc gtcggatacg agc                                   393
```

<210> SEQ ID NO 53
<211> LENGTH: 131
<212> TYPE: PRT
<213> ORGANISM: Bovine

<400> SEQUENCE: 53

```
Gly Gly Leu Val Lys Pro Gly Gly Ser Leu Arg Leu Ser Cys Ala Ala
 1               5                  10                  15

Ser Gly Phe Thr Phe Ser Asp Tyr Tyr Met Ser Trp Ile Arg Gln Ala
            20                  25                  30

Pro Gly Lys Gly Leu Glu Trp Val Ser Tyr Ile Ser Ser Ser Gly Ser
        35                  40                  45

Thr Ile Tyr Tyr Ala Asp Ser Val Lys Gly Arg Phe Thr Ile Ser Arg
    50                  55                  60

Asp Asn Ala Lys Asn Ser Leu Tyr Leu Gln Met Asn Ser Leu Arg Ala
65                  70                  75                  80

Glu Asp Thr Ala Val Tyr Tyr Cys Ala Arg Ile Thr Gly Asp Ala Phe
                85                  90                  95

Asp Ile Trp Gly Gln Gly Thr Met Val Thr Val Ser Ser Gly Ser Ala
            100                 105                 110

Ser Ala Pro Thr Leu Phe Pro Leu Val Ser Cys Glu Asn Ser Pro Ser
        115                 120                 125

Asp Thr Ser
    130
```

<210> SEQ ID NO 54
<211> LENGTH: 411
<212> TYPE: DNA
<213> ORGANISM: Bovine

<400> SEQUENCE: 54

```
gtggagtctg ggggaggctt ggtacagcct gggaggtccc tgagactctc ctgtgcagcg      60
tcaggattca ccttcaggaa ctttggcatg cactgggtcc gccaggctcc aggcaagggg     120
ctggagtggg tgacagttat atggtatgac ggaagtaatc aatactatat agactccgtg     180
aagggccgat tcaccatctc cagagacaat tccaagaaca tgttgtatct gcaaatgaac     240
agcctgagag ccgaggatac ggctgtgtat tactgtgcga gatcgcaa tggcctgaag      300 tacttcgatc tctggggccg tggcaccctg gtcactgtct catcagggag tgcatccgcc     360
ccaacccttt tccccctcgt ctcctgtgag aattccccgt cggatacgag c              411
```

<210> SEQ ID NO 55
<211> LENGTH: 137
<212> TYPE: PRT
<213> ORGANISM: Bovine

<400> SEQUENCE: 55

```
Val Glu Ser Gly Gly Gly Leu Val Gln Pro Gly Arg Ser Leu Arg Leu
 1               5                  10                  15
```

```
Ser Cys Ala Ala Ser Gly Phe Thr Phe Arg Asn Phe Gly Met His Trp
            20                  25                  30

Val Arg Gln Ala Pro Gly Lys Gly Leu Glu Trp Val Thr Val Ile Trp
            35                  40                  45

Tyr Asp Gly Ser Asn Gln Tyr Tyr Ile Asp Ser Val Lys Gly Arg Phe
            50                  55                  60

Thr Ile Ser Arg Asp Asn Ser Lys Asn Met Leu Tyr Leu Gln Met Asn
 65                 70                  75                  80

Ser Leu Arg Ala Glu Asp Thr Ala Val Tyr Tyr Cys Ala Arg Asp Arg
                85                  90                  95

Asn Gly Leu Lys Tyr Phe Asp Leu Trp Gly Arg Gly Thr Leu Val Thr
            100                 105                 110

Val Ser Ser Gly Ser Ala Ser Ala Pro Thr Leu Phe Pro Leu Val Ser
            115                 120                 125

Cys Glu Asn Ser Pro Ser Asp Thr Ser
            130                 135
```

<210> SEQ ID NO 56
<211> LENGTH: 441
<212> TYPE: DNA
<213> ORGANISM: Bovine

<400> SEQUENCE: 56

```
accctcctca ctcactgtgc agggtcctgg gcccagtctg tgctgactca gccacccctca    60
gcgtctggga cccccgggca gagggtcacc atctcttgtt ctggaagcag ctccaacatc   120
ggaagtaatt atgtatactg gtaccagcag ctcccaggaa cggcccccaa actcctcatc   180
tataggaata atcagcggcc ctcaggggtc cctgaccgat tctctggctc caagtctggc   240
acctcagcct ccctggccat cagtgggctc cggtccgagg atgaggctga ttattactgt   300
gcagcatggg atgacagcct gagtggtctt ttcggcggag ggaccaagct gaccgtccta   360
ggtcagccca aggctgcccc ctcggtcact ctgttcccac cctcctctga ggagcttcaa   420
gccaacaagg ccacactggt g                                              441
```

<210> SEQ ID NO 57
<211> LENGTH: 147
<212> TYPE: PRT
<213> ORGANISM: Bovine

<400> SEQUENCE: 57

```
Thr Leu Leu Thr His Cys Ala Gly Ser Trp Ala Gln Ser Val Leu Thr
 1               5                  10                  15

Gln Pro Pro Ser Ala Ser Gly Thr Pro Gly Gln Arg Val Thr Ile Ser
            20                  25                  30

Cys Ser Gly Ser Ser Ser Asn Ile Gly Ser Asn Tyr Val Tyr Trp Tyr
            35                  40                  45

Gln Gln Leu Pro Gly Thr Ala Pro Lys Leu Leu Ile Tyr Arg Asn Asn
            50                  55                  60

Gln Arg Pro Ser Gly Val Pro Asp Arg Phe Ser Gly Ser Lys Ser Gly
 65                 70                  75                  80

Thr Ser Ala Ser Leu Ala Ile Ser Gly Leu Arg Ser Glu Asp Glu Ala
                85                  90                  95

Asp Tyr Tyr Cys Ala Ala Trp Asp Asp Ser Leu Ser Gly Leu Phe Gly
            100                 105                 110

Gly Gly Thr Lys Leu Thr Val Leu Gly Gln Pro Lys Ala Ala Pro Ser
```

```
                    115                 120                 125
Val Thr Leu Phe Pro Pro Ser Ser Glu Glu Leu Gln Ala Asn Lys Ala
        130                 135                 140

Thr Leu Val
145

<210> SEQ ID NO 58
<211> LENGTH: 459
<212> TYPE: DNA
<213> ORGANISM: Bovine

<400> SEQUENCE: 58
agttggaccc ctctctggct cactctcttc actctttgca taggttctgt ggtttcttct      60
gagctgactc aggaccctgc tgtgtctgtg gccttgggac agacagtcag gatcacatgc     120
caaggagaca gcctcagaag ctattatgca agctggtacc agcagaagcc aggacaagcc     180
cctgtacttg tcatctatgg taaaaacaac cggccctcag ggatcccaga ccgattctct     240
ggctccagct caggaaacac agcttccttg accatcactg gggctcaggc ggaggatgag     300
gctgactatt actgtaactc ccgggacagc agtggtaacc atgtggtatt cggcggaggg     360
accaagctga ccgtcctagg tcagcccaag gctgccccct cggtcactct gttcccaccc     420
tcctctgagg agcttcaagc caacaaggcc acactggtg                           459

<210> SEQ ID NO 59
<211> LENGTH: 153
<212> TYPE: PRT
<213> ORGANISM: Bovine

<400> SEQUENCE: 59

Ser Trp Thr Pro Leu Trp Leu Thr Leu Phe Thr Leu Cys Ile Gly Ser
 1               5                  10                  15

Val Val Ser Ser Glu Leu Thr Gln Asp Pro Ala Val Ser Val Ala Leu
            20                  25                  30

Gly Gln Thr Val Arg Ile Thr Cys Gln Gly Asp Ser Leu Arg Ser Tyr
        35                  40                  45

Tyr Ala Ser Trp Tyr Gln Gln Lys Pro Gly Gln Ala Pro Val Leu Val
    50                  55                  60

Ile Tyr Gly Lys Asn Asn Arg Pro Ser Gly Ile Pro Asp Arg Phe Ser
65                  70                  75                  80

Gly Ser Ser Ser Gly Asn Thr Ala Ser Leu Thr Ile Thr Gly Ala Gln
                85                  90                  95

Ala Glu Asp Glu Ala Asp Tyr Tyr Cys Asn Ser Arg Asp Ser Ser Gly
            100                 105                 110

Asn His Val Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val
145                 150

<210> SEQ ID NO 60
<211> LENGTH: 723
<212> TYPE: DNA
<213> ORGANISM: Bovine

<400> SEQUENCE: 60
atgagattcc ctgctcagct cctggggctc ctcctgctct gggtcccagg atccagtggg      60
```

```
gatgttgtgc tgacccagac tcccctctcc ctgtctatca tccctggaga gacggtctcc    120
atctcctgca agtctactca gagtctgaaa tatagtgatg gaaaaaccta tttgtactgg    180
cttcaacata aaccaggcca atcaccacag cttttgatct atgctgtttc cagccgttac    240
actggggtcc cagacaggtt cactggcagt gggtcagaaa cagatttcac acttacgatc    300
aacagtgtgc aggctgagga tgttggagtc tattactgtc ttcaaacaac atatgtccca    360
aatactttcg gccaaggaac caaggtagag atcaaaaggt ctgatgctga gccatccgtc    420
ttcctcttca aaccatctga tgagcagctg aagaccggaa ctgtctctgt cgtgtgcttg    480
gtgaatgatt tctaccccaa agatatcaat gtcaagtgga agtggatggg ggttactcag    540
agcagcagca acttccaaaa cagtttcaca gaccaggaca gcaagaaaag cacctacagc    600
ctcagcagca tcctgacact gcccagctca gagtaccaaa gccatgacgc ctatacgtgt    660
gaggtcagcc acaagagcct gactaccacc ctcgtcaaga gcttcagtaa gaacgagtgt    720
tag                                                                  723
```

```
<210> SEQ ID NO 61
<211> LENGTH: 20
<212> TYPE: DNA
<213> ORGANISM: Artificial Sequence
<220> FEATURE:
<223> OTHER INFORMATION: Synthetic Primer

<400> SEQUENCE: 61
gatgatgtct ccaggatgcc                                                 20

<210> SEQ ID NO 62
<211> LENGTH: 21
<212> TYPE: DNA
<213> ORGANISM: Artificial Sequence
<220> FEATURE:
<223> OTHER INFORMATION: Synthetic Primer

<400> SEQUENCE: 62
gacaagctta atatccgcag g                                               21

<210> SEQ ID NO 63
<211> LENGTH: 30
<212> TYPE: DNA
<213> ORGANISM: Artificial Sequence
<220> FEATURE:
<223> OTHER INFORMATION: Synthetic Primer

<400> SEQUENCE: 63
aagaagagaa aggtagaaga ccccaaggac                                      30

<210> SEQ ID NO 64
<211> LENGTH: 28
<212> TYPE: DNA
<213> ORGANISM: Artificial Sequence
<220> FEATURE:
<223> OTHER INFORMATION: Synthetic Primer

<400> SEQUENCE: 64
cctgggtata gacaggtggg tattgtgc                                        28

<210> SEQ ID NO 65
<211> LENGTH: 40
<212> TYPE: DNA
<213> ORGANISM: Artificial Sequence
<220> FEATURE:
```

```
<223> OTHER INFORMATION: Synthetic Primer

<400> SEQUENCE: 65
ggggtctaga gcagacacta cactgatggg cccttggtcc                    40

<210> SEQ ID NO 66
<211> LENGTH: 36
<212> TYPE: DNA
<213> ORGANISM: Artificial Sequence
<220> FEATURE:
<223> OTHER INFORMATION: Synthetic Primer

<400> SEQUENCE: 66
ggggaagctt cgtgtccctg gtcctgtctg acacag                        36

<210> SEQ ID NO 67
<211> LENGTH: 34
<212> TYPE: DNA
<213> ORGANISM: Artificial Sequence
<220> FEATURE:
<223> OTHER INFORMATION: Synthetic Primer

<400> SEQUENCE: 67
ggggctcgag gtcggcgaag gatgggggga ggtg                          34

<210> SEQ ID NO 68
<211> LENGTH: 35
<212> TYPE: DNA
<213> ORGANISM: Artificial Sequence
<220> FEATURE:
<223> OTHER INFORMATION: Synthetic Primer

<400> SEQUENCE: 68 gggggggtacc gctgggctga gctgggcaga gtggg                        35
```